(12) United States Patent
Chvatchko Missotten et al.

(10) Patent No.: US 10,364,296 B2
(45) Date of Patent: Jul. 30, 2019

(54) ANTIBODIES SPECIFIC FOR MMP9

(71) Applicants: CALYPSO BIOTECH SA, Plan-les-Ouates (CH); MERCK PATENT GMBH, Darmstadt (DE)

(72) Inventors: Yolande Chvatchko Missotten, Confignon (CH); Laurence Goffin, Ornex (FR); Olivier Leger, Saint Sixt (FR); Steven M. Dunn, Sergy (FR); Christine Power, Thoiry (FR); Kinsey Maundrell, Chêne Bougeries (CH)

(73) Assignees: CALYPSO BIOTECH SA, Plan-les-Ouates (CH); MERCK PATENT GMBH, Darmstadt (DE)

( * ) Notice: Subject to any disclaimer, the term of this patent is extended or adjusted under 35 U.S.C. 154(b) by 70 days.

(21) Appl. No.: 15/503,447

(22) PCT Filed: Aug. 13, 2015

(86) PCT No.: PCT/EP2015/068645
§ 371 (c)(1),
(2) Date: Feb. 13, 2017

(87) PCT Pub. No.: WO2016/023979
PCT Pub. Date: Feb. 18, 2016

(65) Prior Publication Data
US 2017/0233495 A1    Aug. 17, 2017

(30) Foreign Application Priority Data

Aug. 13, 2014 (EP) .................................. 14180765

(51) Int. Cl.
| | |
|---|---|
| *C07K 16/40* | (2006.01) |
| *G01N 33/53* | (2006.01) |
| *C12N 15/13* | (2006.01) |
| *G01N 33/573* | (2006.01) |
| *A61K 39/00* | (2006.01) |

(52) U.S. Cl.
CPC ...... *C07K 16/40* (2013.01); *C12Y 304/24035* (2013.01); *G01N 33/573* (2013.01); *A61K 2039/505* (2013.01); *C07K 2317/33* (2013.01); *C07K 2317/34* (2013.01); *C07K 2317/565* (2013.01); *C07K 2317/76* (2013.01); *C07K 2317/90* (2013.01); *C07K 2317/92* (2013.01); *G01N 2333/96494* (2013.01)

(58) Field of Classification Search
CPC ......... C07K 16/40; C12N 15/09; G01N 33/53
See application file for complete search history.

(56) References Cited

U.S. PATENT DOCUMENTS

| | | |
|---|---|---|
| 2009/0297499 A1 | 12/2009 | Devy |
| 2009/0311245 A1 | 12/2009 | Devy et al. |
| 2011/0135573 A1 | 6/2011 | Devy |

FOREIGN PATENT DOCUMENTS

| | | |
|---|---|---|
| WO | WO 02/066057 | 8/2002 |
| WO | WO 2009/111450 | 9/2009 |
| WO | WO 2010/045388 | 4/2010 |
| WO | WO 2011/028883 | 3/2011 |
| WO | WO 2012/027721 | 3/2012 |
| WO | WO 2013/130078 | 9/2013 |

OTHER PUBLICATIONS

Agrawal, S. et al. "Dystroglycan is selectively cleaved at the parenchymal basement membrane at sites of leukocyte extravasation in experimental autoimmune encephalomyelitis" *Journal of Experimental Medicine*, Apr. 17, 2006, pp. 1007-1019, vol. 203, No. 4.

Baugh, M. D. et al. "Matrix Metalloproteinase Levels Are Elevated in Inflammatory Bowel Disease" *Gastroenterology*, Oct. 1999, pp. 814-822, vol. 117.

Candelario-Jalil, E. et al. "Diverse Roles of Matrix Metalloproteinases and Tissue Inhibitors of Metalloproteinases in Neuroinflammation and Cerebral Ischemia" *Neuroscience*, Feb. 6, 2009, pp. 983-994, vol. 158, No. 3.

Chen, J. et al. "Prognostic and clinical significance of STAT3 and MMP9 in patients with gastric cancer: a meta-analysis of a Chinese cohort" *International Journal of Clinical and Experimental Medicine*, 2015, pp. 546-557, vol. 8, No. 1.

De Bruyn, M. et al. "Neutrophil gelatinase B-associated lipocalin-matrix metalloproteinase-9 (NGAL-MMP-9) complex as a surrogate serum marker for mucosal healing in ulcerative colitis" *Inflammatory Bowel Diseases*, 2014, pp. 1198-1207, vol. 20.

Dufour, A. et al. "Role of Matrix Metalloproteinase-9 Dimers in Cell Migration" *The Journal of Biological Chemistry*, Nov. 12, 2010, pp. 35944-35956, vol. 285, No. 46.

Efsen, E. et al. "Ramiprilate Inhibits Functional Matrix Metalloproteinase Activity in Crohn's Disease Fistulas" *Basic & Clinical Pharmacology & Toxicology*, 2011, pp. 208-216, vol. 109.

(Continued)

*Primary Examiner* — Prema M Mertz
(74) *Attorney, Agent, or Firm* — Saliwanchik, Lloyd & Eisenschenk

(57) ABSTRACT

The present invention relates to new proteins that bind to MMP9 and comprise at least one fragment of a heavy chain variable region and/or at least one fragment of a light chain variable region of an antibody. In particular, the MMP9 binding proteins according to the invention are able to neutralize MMP9 activity and are useful in the prevention and/or treatment of inflammatory and/or autoimmune diseases or cancers. In particular, the MMP9 binding proteins according to the invention are useful in diagnosis of MMP9-related disorders.

17 Claims, 20 Drawing Sheets

Specification includes a Sequence Listing.

(56) References Cited

OTHER PUBLICATIONS

Gao, C.-C. et al. "MMI-166, a selective matrix metalloproteinase inhibitor, promotes apoptosis in human pancreatic cancer" *Med Oncol*, 2015, pp. 1-9 (418), vol. 32, No. 1.

Goffin, L. et al, "Anti-MMP-9 Antibody: A Promising Therapeutic Strategy for Treatment of Inflammatory Bowel Disease Complications with Fibrosis" *Inflamm Bowel Dis*, Sep. 2016, pp. 2041-2057, vol. 22, No. 9.

Herszényi, L. et al. "The Behavior of Matrix Metalloproteinases and Their Inhibitors in Colorectal Cancer" *International Journal of Molecular Sciences*, 2012, pp. 13240-13263, vol. 13.

Hu, J. et al. "Matrix metalloproteinase inhibitors as therapy for inflammatory and vascular diseases" *Nature*, Jun. 2007, pp. 480-498, vol. 6.

Kim, G.-E. et al. "Expression of matrix metalloproteinases and their inhibitors in different immunohistochemical-based molecular subtypes of breast cancer" *BMC Cancer*, 2014, pp. 1-10 (959), vol. 14, No. 1.

Kowluru, R. A. et al. "Matrix metalloproteinases in diabetic retinopathy: potential role of MMP-9" *Expert Opinion on Investigative Drugs*, Jun. 2012, pp. 797-805, vol. 21, No. 6.

Martens, E. et al. "A monoclonal antibody inhibits gelatinase B/MMP-9 by selective binding to part of the catalytic domain and not to the fibronectin or zinc binding domains" *Biochimica et Biophysica Acta 1770*, 2007, pp. 178-186.

Mirshafiey, A. et al. "The Significance of Matrix Metalloproteinases in the Immunopathogenesis and Treatment of Multiple Sclerosis" *Sultan Qaboos University Med J*, pp. e13-e25, vol. 14, No. 1.

Morgunova, E. et al. "Structure of Human Pro-Matrix Metalloproteinase-2: Activation Mechanism Revealed" *Science*, Jun. 4, 1999, pp. 1667-1670, vol. 284.

Mroczko, B. et al. "The Role of Matrix Metalloproteinases and Tissue Inhibitors of Metalloproteinases in the Pathophysiology of Neurodegeneration: A Literature Study" *Journal of Alzheimer's Disease*, 2013, pp. 273-283, vol. 37.

Naito, Y. et al. "Role of Matrix metalloproteinases in inflammatory bowel disease" *Molecular Aspects of Medicine*, 2005, pp. 379-390, vol. 26.

Nathu, Z. et al. "Temporal Changes in MMP mRNA Expression in the Lens Epithelium during Anterior Subcapsular Cataract Formation" *Experimental Eye Research*, Feb. 2009, pp. 323-330, vol. 88, No. 2.

Naylor, M. S. et al. "Expression and Activity of MMPS and Their Regulators in Ovarian Cancer" *International Journal of Cancer*, 1994, pp. 50-56, vol. 58.

Nita, M. et al. "Age-related macular degeneration and changes in the extracellular matrix" *Medical Science Monitor*, Jun. 18, 2014, pp. 1003-1016, vol. 20.

Ogata, Y. et al. "Matrix Metalloproteinase 3 (Stromelysin) Activates the Precursor for the Human Matrix Metalloproteinase 9" *The Journal of Biological Chemistry*, Feb. 25, 1992, pp. 3581-3584, vol. 267, No. 6.

Piera-Velazquez, S. et al. "Role of Endothelial-Mesenchymal Transition (EndoMT) in the Pathogenesis of Fibrotic Disorders" *The American Journal of Pathology*, Sep. 2011, pp. 1074-1080, vol. 179, No. 3.

Roomi, M. W. et al. "Effect of a nutrient mixture on matrix metalloproteinase-9 dimers in various human cancer cell lines" *International Journal of Oncology*, 2014, pp. 986-992, vol. 44.

Roswell, S. et al. "Crystal Structure of Human MMP9 in Complex with a Reverse Hydroxamate Inhibitor" *Journal of Molecular Biology*, 2002, pp. 173-181, vol. 319.

Rudd, P. M. et al. "Glycosylation of Natural Human Neutrophil Gelatinase B and Neutrophil Gelatinase B-Associated Lipocalin" *Biochemistry*, 1999, pp. 13937-13950, vol. 38.

Ruiz-Morales, J. M. et al. "Neutrophil gelatinase-associated lipocalin (NGAL) and matrix metalloproteinase-9 (MMP-9) prognostic value in lung adenocarcinoma" *Tumor Biology*, 2015, pp. 3601-3610, vol. 36.

Sakimoto, T. et al. "Metalloproteinases in Corneal Disease: Degradation and Processing" *Cornea*, Nov. 2012, pp. S50-S56, vol. 31, No. 11, Suppl. 1.

Santos, J. M. et al. "Interrelationship between activation of matrix metalloproteinases and mitochondrial dysfunction in the development of diabetic retinopathy" *Biochem Biophys Res Commun.*, Sep. 6, 2013, pp. 1-12, vol. 438, No. 4.

Szarvas, T. et al. "Matrix metalloproteinases and their clinical relevance in urinary bladder cancer" *Nature Reviews Urology*, May 2011, pp. 241-254, vol. 8.

Yabluchanskiy, A. et al. "Matrix Metalloproteinase-9: Many Shades of Function in Cardiovascular Disease" *Physiology*, 2013, pp. 391-403, vol. 28.

Written Opinion in International Application No. PCT/EP2015/068645, dated Oct. 9, 2015, pp. 1-7.

| | |
|---|---|
| Human | ----------------------------------------------------------------MSLWQ |
| Cyno | MLGLPHTHTHTHTHTHTPCPLSQHLPVKEGWGHRSASLKPPQQLQSDTAALTMSLWQ |
| Rat | ----------------------------------------------------------------MSPWQ |
| Mouse | ----------------------------------------------------------------MSPWQ |
| | * *** |

| | |
|---|---|
| Human | PLVLVLIVLGCCFAAPRQRQSTLVLFPGDLRTN-LTDRQLAEEYLYRGYTRVAEMRGES |
| Cyno | PLVLALLVLGCCCAAPRQRQSTLVLFPGDLKTN-LTDRQLAEDYLYRGYTRVAEMHGDS |
| Rat | PLILVLIALGYSFAAPHQRQPTYVVFPRDLKTSNLTDTQLAEDYLYRGYTRAAQMGEK |
| Mouse | PLLLALLAFGCSSAAPYQRQPTFVVFPKDLKTSNLTDTQLAEAYLYRGYTRAAQMGEK |
| | *: * ***.:* * |

| | |
|---|---|
| Human | KSLGPALLLQKQLSLPETGELDSATLKAMRIPRCGVPDLGRFQTFEGDLKWHHHNITYW |
| Cyno | KSLGPALLLQKQLSLPQTGELDSATLKAMRIPRCGVPDLGRFQTFEGDLKWHHHNITYW |
| Rat | QSIRPALIMLQKQLSLPQTGELDSETLKAIRSPRCGVPDVGKFQTFDGDLKWHHHNITYW |
| Mouse | QSIRPALIMLQKQLSLPQTGELDSQTLKAIRTPRCGVPDVGRFQTFKG-LKWDHHNITYW |
| | .: *:*.*** : * |

| | |
|---|---|
| Human | IQNYSEDLPRAVIDDAFARAFALMSAVTPLTFTRVYSRDADIVIQFGVAEHGDYPFDGK |
| Cyno | IQNYSEDLPRAVIEDAFARAFALMSAVTPLTFTRVYSRDADIVIQFGVAEHGDYPFDGK |
| Rat | IQSYTEDLPRDVIDDSFARAFAVWSAVTPLTFTRVGLEADIVIQFGVAEHGDYPFDGK |
| Mouse | IQNYSEDLPRDMIDDAFARAFAVWGEVAPLTFTRVGPEADIVIQFGVAEHGDYPFDGK |
| | *. . . . |

| | |
|---|---|
| Human | DGLLAHAFPPGPGIQGDAHFDDELWSLGKGVVVPTRFGNADGAACHFPFIFEGRSYSAC |
| Cyno | DGLLAHAFPPGPGIQGDAHFDDELWSLGKGVVVPTKFGNADGAACHFPFTFEGRSYSAC |
| Rat | DGSYTEDLPRDVIDDSFARAFAVWSAVTPLTFTRVGLEADIVIQFGVAEHGDYPFDGK |
| Mouse | DGLLAHAFPPGAGVQGDAHFDDELWSLGKGVVIPTYYGNSNGAPCHFPFTFEGRSYSAC |
| | * |

Figure 2

```
Human  TTDGRSDGLPWCSTTANYDTDDRFGFCPSERLYTQDGNADGKPCQFPPIFQGQSYSACTT
Cyno   TTDGRSDGVPWCSTTANYDTDDRRFGFCPSERLYTQDGNADGKPCQFPPIFQGQSYSACTT
Rat    TTDGRNDGKPWCGTTADYDTDRKYGFCPSENLYTEHGNGDGKPCVFPPIFEGHSYSACTT
Mouse  TTDGRNDGTPWCSTTADYDKDGKFGFCPSERLYTEHGNGEGKPCVFPPIFEGRSYSACTT
        ****:**  *** ***.**.   ****.*** :* ****  ****.*****   ****

Human  DGRSDGYRWCATTANYDRDKLFGFCPTRADSTVMGGNSAGELCVFPFTFLGKEYSTCTSE
Cyno   DGRSDGYRWCATTANYDQDKLYGFCPTRADSTVIGGNSAGELCVFPFTFLGKEYSTCTSE
Rat    KGRSDGYRWCATTANYDQDKADGFCPTRADVTVGGNSAGEMCVFPFVFLGKQYSTCTSE
Mouse  KGRSDGYRWCATTANYDQDKLYGFCPTRVDAIVVGGNSAGELCVFPVFLGKQYSSCTSD
       .**********:*****:** ******.*: . ****** ****  .***:**:***:

Human  GRGDGRLWCATTSNFDSDKKWGFCPDQGYSLFLVAAHEFGHALGLDHSSVPEALMYPMYR
Cyno   GRGDGRLWCATTSNFDRDKKWGFCPDQGYSLFLVAAHEFGHALGLDHSSVPEALMYPMYR
Rat    GRSDGRLWCATTSNFDADKKWGFCPDQGYSLFLVAAHEFGHALGLDHSSVPEALMYPMYH
Mouse  GRRDGRLWCATTSNFDTDKKWGFCPDQGYSLFLVAAHEFGHALGLDHSSVPEALMYPLYS
       ** *************  *******************************:**: *

Human  FTEGPPLHKDDVNGIRHLYGPRPEPEPRPPTTTP--QPTAPPTVCPTGPPTVHPSERPT
Cyno   FTEEPPLHKDDVNGIQYLYGSRPEPEPRPPTTTP--QPTAPPTVCPTGPPTVRPSDRPI
Rat    YHEDSPLHEDDIKGIHHLYGRGSKPDPRPPATTAAEPQPTAPPTMCSTAPPMAYPTGGPI
Mouse  YLEGFPLNKDDIDGIQYLYGRGSKPDPRPPATTTEPQPTAPPTMCPTIPPTAYPTVGPI
         :  **::**: **:.*** .   : ***.**   ********  :  **  * .

Human  AGPTGPPSAGPTG----------PPTAGPSTATTVPLSPVDDACNVNIFDAIAE
Cyno   AGPTGPPSAGPTG----------PPTAGPSTTTVPLNPVDDACNVNIFDAITE
Rat    VAPTGAPSPGPTG----------PPTAGPSEAPTESSTPDDNPCNVDVFDAIAD
Mouse  VGPTGAPSPGPTSSPSPGPTGAPSPGPTAPPTAGSSEASTESLSPADNPCNVDVFDAIAE
       . ***.**.***            * . .        .  . : ***:::*****
```

Figure 2 (continued)

```
Human  IGNQLYLFKDGKYWRFSEGRGSRPQGPFLIADKWPALPRKLDSVFEERLSKKLFFFSGRQ
Cyno   IGNQLYLFKADGKYWRFSERRGSRLQGPFLIADTWPALPRKLDSAFEEPLSKKLFFFSGRQ
Rat    IQGALHFFKDGRYWKFSNHGGNQLQGPFLIARTWPAFPSKINSAFEDPQPKKIFFFLWAQ
Mouse  IQGALHFFKDGWYWKFLNHRGSPLQGPFLTARTWPALPATLDSAFEDPQTKRVFFFSGRQ
       *  * :**** *: * .  *****:* ** * :.*::. . : **:  .

Human  VWVYTGASVLGPRRLDKLGLGADVAQVTGALRSGRGKMLLFSGRRLWRFDVKAQMVDPRS
Cyno   VWVYTGSSVLGPRRLDKLGLGADVAQVTGALRGAGKMLLFSGRRFWRFDVKAQMVDPRS
Rat    MWVYTGQSVLGPRSLDKLGIGSEVTLVTGLLPRRGGKALLISRERIWKFDLKSQKVDPQS
Mouse  MWVYTGKTVLGPRSLDKLGIGPEVTHVSGLIPRRLGKALLFSKGRVWRFDLKSQKVDPQS
       :****   **** ****:*   *  *:*     *:*:*..:*.:** ..::***:*

Human  ASEVDRMFPGVPLDTHDVFQYREKAYFCQDRFYWRVSSRSEIN------QVDQVGYVTY
Cyno   ASEVDRMFPGVPLDTHDVFQYQEKAYFCQDRFYWRVSSQSGVN------QVDQVGYVTY
Rat    VTRLDNEFSGVPWNSHNVFQYQDKAYFCHDKYFWRVSFHNRVN------QVDHVAYVTY
Mouse  VIRVDKEFSGVPWNSHDIFQYQDKAYFCHGKFFWRVSFQNEVNKVDHEVNQVDDVGYVTY
       . .:* :*** :.*::***:.****: .::****.  .*    ***.* ****

Human  DILQCPED
Cyno   DILQCPED
Rat    DLLQCP--
Mouse  DLLQCP--
       *:****
```

Figure 2 (continued)

|  |  | CDR1 | | CDR2 |
|---|---|---|---|---|
| F20-VH | EVQLVESGGGLVQPGRSLRLSCAASGFTFNDYPMHWVRQAPGKGLEWVSGISSNSGSVGY |
| F20-VH-GL1 | EVQLVESGGGLVQPGRSLRLSCAASGFTFNDYPMHWVRQAPGKGLEWVSGISSNSGSVGY |
| F20-VH-GL1-V1 | EVQLVESGGGLVQPGRSLRLSCAASGFTFNDYPMHWVRQAPGKGLEWVSGISSNSGSVGY |
| F20-VH-GL1-V1-V9 | EVQLVESGGGLVQPGRSLRLSCAASGFTFNDYPMHWVRQAPGKGLEWVSGISSQSGSVGY |
| F20-VH-GL1-V1-V9-V14 | EVQLVESGGGLVQPGRSLRLSCAASGFTFNDYPMHWVRQAPGKGLEWVSGISSQSGSVGY |
| F20-VH-GL1-V4-V9 | EVQLVESGGGLVQPGRSLRLSCAASGFTFNDYPMHWVRQAPGKGLEWVSGISSRSGSVGY |
| F20-VH-GL1-V4-V9-V14 | EVQLVESGGGLVQPGRSLRLSCAASGFTFNDYPMHWVRQAPGKGLEWVSGISSRSGSVGY |
| | ************************************************************ |

CDR3

| F20-VH | ADSVKGRFTISRDNAKNSLYLQMNSLRDEDTAVYYCARDKIYYGSGSYDFYYYGMDVWG |
| F20-VH-GL1 | ADSVKGRFTISRDNAKNSLYLQMNSLRAEDTALYYCARDKIYYGSGSYDFYYYGMDVWG |
| F20-VH-GL1-V1 | AESVKGRFTISRDNAKNSLYLQMNSLRAEDTALYYCARDKIYYGSGSYDFYYYGMDVWG |
| F20-VH-GL1-V1-V9 | AESVKGRFTISRDNAKNSLYLQMNSLRAEDTALYYCARDKIYYGSGSYDFYYYGIDVWG |
| F20-VH-GL1-V1-V9-V14 | AESVKGRFTISRDNAKNSLYLQMNSLRAEDTALYYCARDKIYYGSGSYDFYYYGIDVWG |
| F20-VH-GL1-V4-V9 | AESVKGRFTISRDNAKNSLYLQMNSLRAEDTALYYCARDKIYYGSGSYDFYYYGMDVWG |
| F20-VH-GL1-V4-V9-V14 | AESVKGRFTISRDNAKNSLYLQMNSLRAEDTALYYCARDKIYYGSGSYDFYYYGIDVWG |
| | *:**********************:*:***************************: |

| F20-VH | QGTTVTVSSASTKGPSVFPLAPCSRSTSESTAALGCLVKDYFPEPVTVSWNSGALTSGVH |
| F20-VH-GL1 | QGTTVTVSSASTKGPSVFPLAPCSRSTSESTAALGCLVKDYFPEPVTVSWNSGALTSGVH |
| F20-VH-GL1-V1 | QGTTVTVSSASTKGPSVFPLAPCSRSTSESTAALGCLVKDYFPEPVTVSWNSGALTSGVH |
| F20-VH-GL1-V1-V9 | QGTTVTVSSASTKGPSVFPLAPCSRSTSESTAALGCLVKDYFPEPVTVSWNSGALTSGVH |
| F20-VH-GL1-V1-V9-V14 | QGTTVTVSSASTKGPSVFPLAPCSRSTSESTAALGCLVKDYFPEPVTVSWNSGALTSGVH |
| F20-VH-GL1-V4-V9 | QGTTVTVSSASTKGPSVFPLAPCSRSTSESTAALGCLVKDYFPEPVTVSWNSGALTSGVH |
| F20-VH-GL1-V4-V9-V14 | QGTTVTVSSASTKGPSVFPLAPCSRSTSESTAALGCLVKDYFPEPVTVSWNSGALTSGVH |
| | ************************************************************ |

Figure 3

```
*F20-VH               TFPAVLQSSGLYSLSSVVTVPSSSLGTKTYTCNVDHKPSNTKVDKRVESKYGPPCPPCPA
**F20-VH-GL1          TFPAVLQSSGLYSLSSVVTVPSSSLGTKTYTCNVDHKPSNTKVDKRVESKYGPPCPPCPA
***F20-VH-GL1-V1-V9   TFPAVLQSSGLYSLSSVVTVPSSSLGTKTYTCNVDHKPSNTKVDKRVESKYGPPCPPCPA
****F20-VH-GL1-V1-V9-V14  TFPAVLQSSGLYSLSSVVTVPSSSLGTKTYTCNVDHKPSNTKVDKRVESKYGPPCPPCPA
*****F20-VH-GL1-V4-V9 TFPAVLQSSGLYSLSSVVTVPSSSLGTKTYTCNVDHKPSNTKVDKRVESKYGPPCPPCPA
******F20-VH-GL1-V4-V9-V14 TFPAVLQSSGLYSLSSVVTVPSSSLGTKTYTCNVDHKPSNTKVDKRVESKYGPPCPPCPA
                      ************************************************************

*F20-VH               PEFLGGPSVFLFPPKPKDTLMISRTPEVTCVVVDVSQEDPEVQFNWYVDGVEVHNAKTKP
**F20-VH-GL1          PEFLGGPSVFLFPPKPKDTLMISRTPEVTCVVVDVSQEDPEVQFNWYVDGVEVHNAKTKP
***F20-VH-GL1-V1-V9   PEFLGGPSVFLFPPKPKDTLMISRTPEVTCVVVDVSQEDPEVQFNWYVDGVEVHNAKTKP
****F20-VH-GL1-V1-V9-V14  PEFLGGPSVFLFPPKPKDTLMISRTPEVTCVVVDVSQEDPEVQFNWYVDGVEVHNAKTKP
*****F20-VH-GL1-V4-V9 PEFLGGPSVFLFPPKPKDTLMISRTPEVTCVVVDVSQEDPEVQFNWYVDGVEVHNAKTKP
******F20-VH-GL1-V4-V9-V14 PEFLGGPSVFLFPPKPKDTLMISRTPEVTCVVVDVSQEDPEVQFNWYVDGVEVHNAKTKP
                      ************************************************************

*F20-VH               REEQFNSTYRVVSVLTVLHQDWLNGKEYKCKVSNKGLPSSIEKTISKAKGQPREPQVYTL
**F20-VH-GL1          REEQFNSTYRVVSVLTVLHQDWLNGKEYKCKVSNKGLPSSIEKTISKAKGQPREPQVYTL
***F20-VH-GL1-V1-V9   REEQFNSTYRVVSVLTVLHQDWLNGKEYKCKVSNKGLPSSIEKTISKAKGQPREPQVYTL
****F20-VH-GL1-V1-V9-V14  REEQFNSTYRVVSVLTVLHQDWLNGKEYKCKVSNKGLPSSIEKTISKAKGQPREPQVYTL
*****F20-VH-GL1-V4-V9 REEQFNSTYRVVSVLTVLHQDWLNGKEYKCKVSNKGLPSSIEKTISKAKGQPREPQVYTL
******F20-VH-GL1-V4-V9-V14 REEQFNSTYRVVSVLTVLHQDWLNGKEYKCKVSNKGLPSSIEKTISKAKGQPREPQVYTL
                      ************************************************************
```

Figure 3 (continued)

```
              F20-VH  PPSQEEMTKNQVSLTCLVKGFYPSDIAVEWESNGQPENNYKTTPPVLDSDGSFFLYSKLT
          F20-VH-GL1  PPSQEEMTKNQVSLTCLVKGFYPSDIAVEWESNGQPENNYKTTPPVLDSDGSFFLYSKLT
       F20-VH-GL1-V1  PPSQEEMTKNQVSLTCLVKGFYPSDIAVEWESNGQPENNYKTTPPVLDSDGSFFLYSKLT
    F20-VH-GL1-V1-V9  PPSQEEMTKNQVSLTCLVKGFYPSDIAVEWESNGQPENNYKTTPPVLDSDGSFFLYSKLT
       F20-VH-GL1-V4  PPSQEEMTKNQVSLTCLVKGFYPSDIAVEWESNGQPENNYKTTPPVLDSDGSFFLYSKLT
F20-VH-GL1-V4-V9-V14  PPSQEEMTKNQVSLTCLVKGFYPSDIAVEWESNGQPENNYKTTPPVLDSDGSFFLYSKLT
                     ************************************************************

F20-VH  VDKSRWQEGNVFSCSVMHEALHNHYTQKSLSLSLG
          F20-VH-GL1  VDKSRWQEGNVFSCSVMHEALHNHYTQKSLSLSLG
       F20-VH-GL1-V1  VDKSRWQEGNVFSCSVMHEALHNHYTQKSLSLSLG
    F20-VH-GL1-V1-V9  VDKSRWQEGNVFSCSVMHEALHNHYTQKSLSLSLG
       F20-VH-GL1-V4  VDKSRWQEGNVFSCSVMHEALHNHYTQKSLSLSLG
F20-VH-GL1-V4-V9-V14  VDKSRWQEGNVFSCSVMHEALHNHYTQKSLSLSLG
                     ***********************************
```

Figure 3 (continued)

```
                              CDR1                                          CDR2
*B03-VL    SSELTQDPAVSVALGQTVRITCQGDSLRSYYASWYQQKPGQAPVVVIYGKNNRPSGIPDR
*B03-VL-GL1 SSELTQDPAVSVALGQTVRITCQGDSLRSYYASWYQQKPGQAPVVVIYGKNNRPSGIPDR
                                                                CDR3
*B03-VL    FSGSSSGNTVSLTITGAQAEDEADYCQSRDNIGNHRVVLFGGGTKVTVLGQPKAAPSVT
*B03-VL-GL1 FSGSSSGNTVSLTITGAQAEDEADYCQSRDNIGNHRVVLFGGGTKLTVLGQPKAAPSVT

*B03-VL    LFPPSSEELQANKATLVCLISDFYPGAVTVAWKADSSPVKAGVETTTPSKQSNNKYAASS
*B03-VL-GL1 LFPPSSEELQANKATLVCLISDFYPGAVTVAWKADSSPVKAGVETTTPSKQSNNKYAASS

*B03-VL    YLSLTPEQWKSHRSYSCQVTHEGSTVEKTVAPTECS
*B03-VL-GL1 YLSLTPEQWKSHRSYSCQVTHEGSTVEKTVAPTECS
```

Figure 4

```
                                    CDR2
                       CDR1
*B08-VL     QSALTQPRSVSGSPGQSVTISCTGTSNDVGAYNRVSWYQQHPGKAPKLLIYGVSNRPSGV
*B08-VL-GL6 QSALTQPASVSGSPGQSITISCTGTSNDVGAYNRVSWYQQHPGKAPKLMIYGVSNRPSGV
            *****.******** **:*************************** :************

CDR3
*B08-VL     STRFSGSKSGNTASLTISGLLAADEADFYCTSYSSSTTSYVFGGGTKVTVLGQPKAAPS
*B08-VL-GL6 SNRFSGSKSGNTASLTISGLQAEDEADFYCTSYSSSTTSYVFGGGTKVTVLGQPKAAPS
            *.******************  *:********************************

*B08-VL     VTLFPPSSEELQANKATLVCLISDFYPGAVTVAWKADSSPVKAGVETTTPSKQSNNKYAA
*B08-VL-GL6 VTLFPPSSEELQANKATLVCLISDFYPGAVTVAWKADSSPVKAGVETTTPSKQSNNKYAA
            ************************************************************

*B08-VL     SSYLSLTPEQWKSHRSYSCQVTHEGSTVEKTVAPTECS
*B08-VL-GL6 SSYLSLTPEQWKSHRSYSCQVTHEGSTVEKTVAPTECS
            **************************************
```

Figure 5

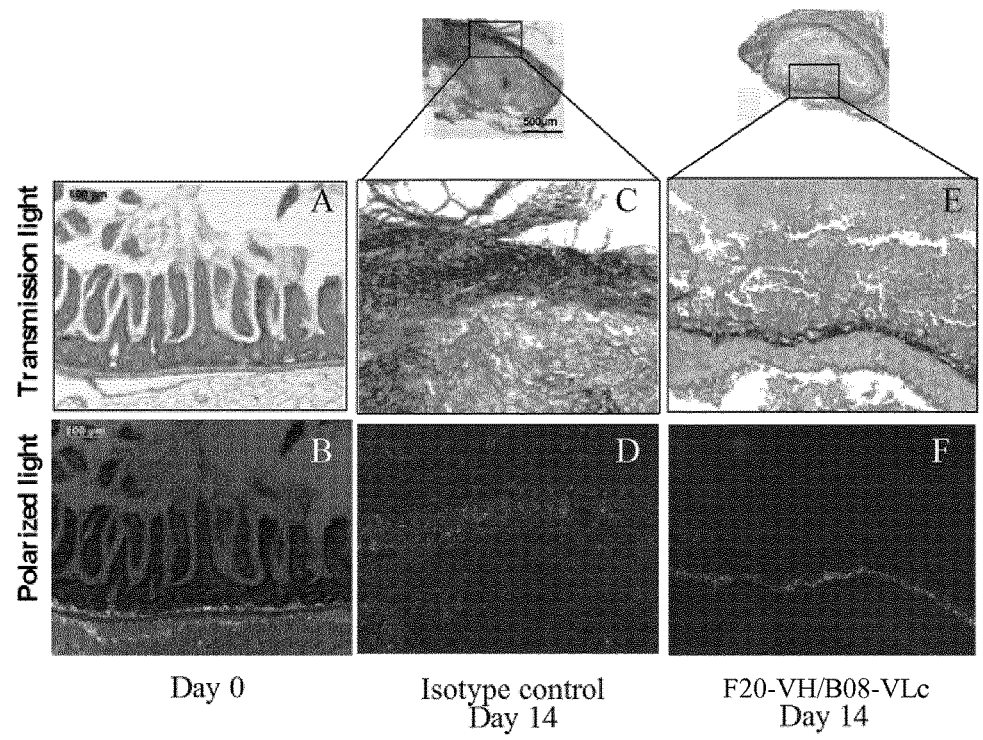
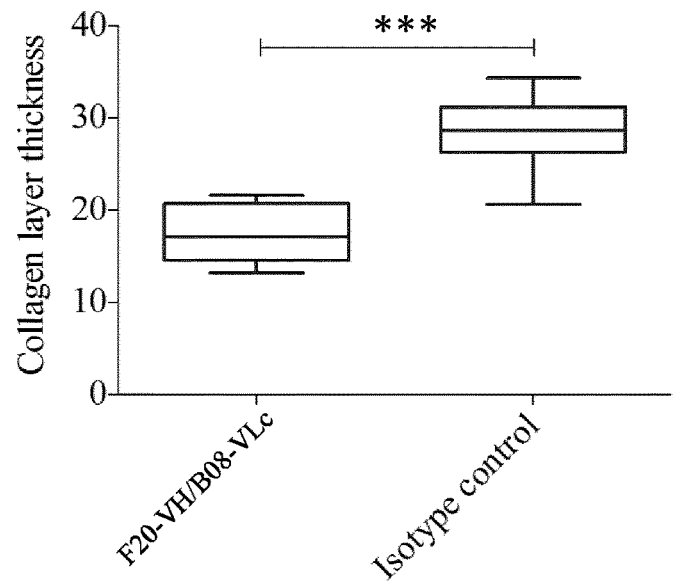
Figure 16

ANTIBODIES SPECIFIC FOR MMP9

CROSS-REFERENCE TO RELATED APPLICATION

This application is the U.S. national stage application of International Patent Application No. PCT/EP2015/068645, filed Aug. 13, 2015.

The Sequence Listing for this application is labeled "Seq-List-replace.txt" which was created on May 4, 2017 and is 120 KB. The entire content of the sequence listing is incorporated herein by reference in its entirety.

FIELD OF THE INVENTION

The present invention relates to antibodies and fragments thereof those specifically binds and neutralize the activity of said protein, as well as to uses thereof as therapeutics or diagnostics.

BACKGROUND OF THE INVENTION

The matrix metalloproteinase (MMP) family consists of at least 23 structurally related, soluble or membrane bound zinc-dependent endopeptidases that are broadly involved in the remodelling of the extracellular matrix (ECM) and in the functional regulation of various bioactive molecules.

All MMPs possess a prototype structure that includes a pro-domain that maintains the MMP in an inactive form and a catalytic domain that acts on a broad spectrum of extracellular matrix components.

Matrix metallopeptidase 9 (MMP9), also known as 92 kDa type IV collagenase or gelatinase B (GELB), is a member of the MMP family enzymes responsible for the degradation of denatured and basement membrane collagens (Agrawal et al., 2006 *J. Exp. Med.* 203, 1007-1019) and for promoting inflammation by processing of soluble proteins, including protease inhibitors (Liu et al., 2000, *J. Exp. Med.* 188, 475-482.), chemokines (Van den Steen et al., 2000, *Lancet Neurol.* 2, 747-756), and cytokines (Nelissen et al., 2003, *Brain* 126, 1371-1381). MMP9 also controls migration, invasion and metastasis of tumor cells by proteolysis of membrane-bound molecules, like growth factor precursors and receptors, tyrosine kinase receptors (TKRs), cell adhesion molecules (Bauvois, 2012, *Biochim Biophys Acta.* 1825(1):29-36.). In disease MMP9 is secreted by many cell types including leukocytes e.g. neutrophils, monocytes/macrophages, and lymphocytes, as well as fibroblasts, myofibroblasts, epithelial cells, smooth muscle cells, endothelial cells, osteoclasts and tumor cells (Vandooren et al., 2013, *Crit. Rev. Biochem. Mol. Biol.* 48(3):222-72).

The general domain structure of MMP9 comprises a secretory leader sequence, an inhibitory pro-domain required for catalytic latency, a 'split' catalytic domain containing three fibronectin type II-like repeat loops that together form a collagen binding domain (CBD), a hyperglycosylated proline-rich linker (also referred to as the OG domain), and a hemopexin-like C-terminal domain (PEX).

Matrix metallopeptidase 2 (MMP2), also known as 72 kDa type IV collagenase or gelatinase A (GELA), is an enzyme that belongs to the same family as MMP9. MMP2 and MMP9 exhibit high amino acid sequence identity (45.9% on full length protein and 63.2% on catalytic domain) and share a highly similar 3D-structure, especially in their catalytic domain. It is therefore very difficult to identify inhibitory anti-human MMP9 antibodies selective versus human MMP2 due to this high structural and amino acid sequence homology (Morgunova et al., 1999, *Science,* 284: 1667-1670).

Many acute inflammatory and autoimmune disease states, fibrotic conditions and invasive cancer, are associated with the presence of excessive MMP9 (Hu et al, 2007, *Nature Reviews Drug Discovery,* 6, 480-498; Ram et al, 2006, *J. Clin. Immunol.,* (26)4: 299-307; Ai Zheng, 2003, *Chinese journal of cancer,* 22(2):178-84; Baugh et al, 1999, *Gastroenterology,* 117:814-822; Santos et al, 2013, *Biochem Biophys Res Commun.,* 438(4): 760-4); Herszényi et al, 2012, *Int. J. Mol. Sci.,* 13, 13240-13263; Lijnen, 2001, *Thromb Haemost,* 86: 324-33; Rosell et al., 2005, *Stroke* 36: 1415-20; Whatling et al., 2004, *Arterioscler Thromb Vasc Biol.,* 24: 10-11; Yasmin et al., 2005, *Arterioscler Thromb Vasc Biol.,* 25:372-8; Vassiliadis et al., 2011, *BMC Dermatol.,* 11: 6) and, thus, this enzyme has received considerable attention as a prospective target for therapeutic intervention.

Strong clinical and experimental evidence demonstrates association of elevated levels of MMP9 with cancer progression, metastasis and shortened patient survival, as it plays a key role in tumor cell invasion and metastasis by digesting the basement membrane and extra cellular matrix components. Neutrophil gelatinase-associated lipocalin (NGAL), which is covalently linked to MMP9 in human neutrophils (Triebel et al., 1992, *FEBS Lett.,* 314, 386-388), protects MMP9 from proteolytic degradation and increases the enzymatic activity of MMP9 and subsequently enhances tumoral invasiveness and diffusion (Yan et al., 2001, *J. Biol. Chem.,* 276, 37258-37265). High concentrations of MMP9/NGAL complex in serum have been associated with a shorter progression-free survival and poor overall survival in clear cell renal cell carcinoma (Perrin et al., 2011, *Prog. En Urol. J. Assoc. Fr. Urol. Société Fr. Urol.,* 21, 851-858).

Specifically the role of MMP-9 has been associated with colorectal cancer (Herszényi et al., 2012, *Int J Mol Sci.,* 13(10):13240-63), pancreatic cancer (Gao et al., 2015, *Med Oncol.* 32(1): 418), breast cancer (Kim et al., 2014, *BMC Cancer.* 14(1):959), lung cancer (Ruiz-Morales et al., *Tumour Biol.* 36(5):3601-10),), ovarian cancer (Naylor et al., 1994, *Int J Cancer,* 58: 50-6), urinary bladder cancer (Szarvas et al., 2011, *Nat Rev Urol.,* 8(5):241-54) and gastric cancer (Chen et al., 2015, *Int J Clin Exp Med.* 8(1):546-57).

The role of MMP9 has been shown in immune pathologies and particularly in inflammatory bowel disease (IBD) where MMP9, is reported as the most abundantly expressed MMP in actively inflamed bowel mucosa, and its expression correlates well with disease activity (Naito and Yoshikawa, 2005, 26:379-390). In IBD, MMP9 is thought to play a key role in inadequate tissue remodeling and activation of proinflammatory cytokines and chemokines thereby enabling the recruitment of activated leukocytes (Nuala et al., 2014, *Inflamm. Bowel* 0:1-15). More specifically, enhanced MMP9 expression along fistula tracts of perianal fistulae and increased MMP9 activity in fistula biopsies was reported in Crohn's disease (CD) patients, supporting the hypothesis that MMP9 may contribute to the formation of fistula that represent a severe complication of CD (Efsen, et al., 2011, *Basic Clin Pharmacol Toxicol.* 109(3):208-16). Furthermore, decreased NGAL/MMP9 serum levels also correlated with mucosal healing in ulcerative colitis patients treated with infliximab (de Bruyn et al., 2014, *Inflamm. Bowel Dis.,* 20, 1198-1207).

The role of MMP9 has been associated with various neurological disorders, for example Alzheimer's disease (Mroczko et al., 2013, *J. Alzheimers Dis.,* 37(2): 273-278), multiple sclerosis (Mirshafiey et al., 2014, *Sultan Qaboos*

Univ Med J, 14(1), 13-25), neuroinflammation or cerebral ischemia (Candelario-Jalil et al., 2009, *Neuroscience* 158 (3):983-94). In Alzheimer's disease the proaggregatory influence on tau oligomer formation in strategic brain regions may be a potential neurotoxic side effect of MMP9 (Wang et al., 2014 *Bio Med Res. Int.*, 2014, ID 908636: 1-8). It has been suggested that a reduction in mature nerve growth factor (mNGF) as a consequence of elevated MMP9-mediated degradation, which degrades mNGF in the extracellular space, may in part underlie the pathogenesis of cognitive deficits in mild cognitive impairment and Alzheimer's disease (Bruno et al., 2009, *J Neuropathol. Exp. Neurol.*, 68(12): 1309-1318).

The role of MMP9 has been associated with fibrotic diseases for example systemic sclerosis, multifocal fibrosclerosis, sclerodermatous graft versus host disease in bone marrow transplant recipients, nephrogenic systemic fibrosis, as well as organ-specific disorders such as pulmonary, liver, and kidney fibrosis (Piera-Velazquez et al., 2011, *Am J Pathol.*, 179(3):1074-80, Peng et al., 2012, *J. Clin. Immunol.*, 32(6):1409-14). For example recent studies have shown that MMPs, in particular MMP9, are implicated in initiation and progression of kidney fibrosis through tubular cell epithelial-mesenchymal transition and activation of resident fibroblasts, endothelial-mesenchymal transition and pericyte-myofibroblast transdifferentiation (Zhao et al., 2013, *World J Nephrol.*, 2(3):84-9).

The pathophysiology of various eye diseases has been associated with MMP9 activity. Some examples include: fibrotic pathologies of the lens (Nathu et al., 2009, *Ex. Eye Res.*, 88(2): 323-330), corneal diseases that is associated with up-regulation of MMP9 (Sakimoto et al., 2012, *Cornea* 31, Suppl 1:S50-6), diabetic retinopathy that presents increased MMP9 levels in patients retina and vitreous (Kowluru et al., 2012, *Expert Opin Investig Drugs*, 21(6): 797-805) and age-related macular degeneration where MMP9 was shown to play a role in its pathogenesis (Nita et al., 2014, *Med Sci Monit*, 20:1003-16).

Cardiovascular diseases involve inflammation and altered tissue remodeling associated with the reorganization of extracellular matrix and the activation of MMP9. Therefore, MMP9 is thought to be associated with pathophysiology of cardiac diseases such as hypertension, atherosclerosis, myocardial infarction, heart failure and coronary artery disease (Yabluchanskiy et al., 2013, *Physiology*, 28(6):391-403).

Furthermore, the role of MMP9 has been associated with various groups of disorders such as skin diseases (Mezentsev et al., 2014, *Gene*, 540(1):1-10), sepsis and acute inflammatory shock syndrome (Lorento et al., 2014, *PLoS One* 9(4):e94318; Qui et al. 2012, *Comb Chem High Throughput Screen.*, 15(7):555-70), osteoarthritis (Bian et al., 2012, *Front Biosci (Elite Ed)*. 4:74-100), chemotherapy-induced mucositis (Al-Dasooqi et al., 2009, *Cancer Chemother Pharmacol.*, 64: 1-9), oral diseases (Al-Azri et al., 2013, *Oral Diseases*, 19: 347-359), osteosclerosis (Teti et al., 1999, *J Bone Miner Res.* 14(12):2107-17), endometriosis (Pitsos et al., 2009, *Reprod Sci.*, 16(8):717-26) or Chagas disease (Geurts et al., 2012, *Pharmacol Ther.*, 133(3):257-79).

Both monomeric and dimeric forms of MMP9 have been identified in a variety of normal and tumor cells (Goldberg et al., 1992, *J. Biol. Chem.*, 267, 4583-4591) and in biological fluids and tissues, indicating that both forms are physiologically relevant. In addition to proteolysis, dimerization of MMP9 through the hemopexin domain appears necessary for MMP9 enhanced cell migration (Dufour et al., 2010, *J. Biol. Chem.*, 285, 35944-35956) and study of the secretion patterns of MMP9 monomer and dimer in a variety of carcinoma, sarcoma, adenosarcoma and leukemia cell lines revealed that high MMP9 and especially dimer secretion levels correlated with the most aggressive cancer cell lines (Roomi et al., 2014, *Int. J. Oncol.* 44, 986-992). All together, these observations highlight the importance for an effective MMP9 neutralizing agent to efficiently inhibits all natural forms of MMP9 and more particularly MMP9 dimer and NGAL/MMP9 complex to treat very aggressive metastatic cancers.

Historically, strategies for MMP blockade have focused on the design of small molecule inhibitors that interact intimately with the catalytic site of the activated enzyme. To date, this approach has failed to translate into the expected clinical benefit partly due to dose-limiting toxicity and severe side effects such as musculoskeletal syndrome. As the architecture of the MMP9 catalytic site is highly conserved across the MMP family, this contra-indication may be attributable to a lack of MMP target selectivity at therapeutic doses.

Antibodies or antibody fragments are likely to interact with, and occlude a far larger portion of the MMP9 structure than active-site directed small molecules providing higher target inhibitory selectivity.

Some antibodies specific for MMP9 have been described in the prior art such as mouse AB0041 and humanized AB0045 (WO 2013/130078) as well as human 539A-M0240-B03 (US 2009/0311245), M0166-F10 (US 2009/0311245 US 2011/0135573), 539A-M0237-D02 (US 2009/0297449 and US 2011/0135573), mouse REGA-3G12 (Martens et al., 2007, *Biochim. Biophys. Acta* 1770, 178-186). Some of the antibodies of the prior art have been described as binding to both MMP9 and MMP2.

Therefore, there remains a need for the development of novel therapeutic agents which show a high affinity and specificity for MMP9 and exhibit a weak or limited affinity and/or specificity to other MMPs such as MMP2, show improved cross-reactivity to non-human MMP9 orthologs, and possess other additional properties such as reduced immunogenicity in humans and/or higher stability, which rend them particularly suitable for therapeutic applications in humans.

SUMMARY OF THE INVENTION

The present invention is directed towards proteins that bind to MMP9, in particular human MMP9, and comprise at least one fragment of a heavy chain variable region and/or at least one fragment of a light chain variable region of an antibody as described herewith.

A first aspect of the invention relates to an isolated antibody specific for MMP9 or antigen-binding fragment thereof, wherein said antibody or fragment binds to MMP9 by interacting with an epitope comprising at least one amino acid within a region consisting of SEQ ID NO: 41, at least one amino acid within a region consisting of SEQ ID NO: 42, and at least one amino acid within a region consisting of SEQ ID NO: 43, wherein said regions are within the catalytic domain of human MMP9.

A second aspect of the invention provides an isolated antibody specific for MMP9 or antigen-binding fragment thereof comprising a heavy chain variable region comprising:
 (i) a heavy chain CDR1 of SEQ ID NO: 2 or a variant thereof wherein 1, 2, or 3 amino acids of said heavy chain CDR1 is substituted by a different amino acid;

(ii) a heavy chain CDR2 of SEQ ID NO: 3 or a variant thereof wherein 1, 2, or 3 amino acids of said heavy chain CDR2 is substituted by a different amino acid;
(iii) a heavy chain CDR3 of SEQ ID NO: 4 or a variant thereof wherein 1, 2, or 3 amino acids of said heavy chain CDR3 is substituted by a different amino acid.

A more particular aspect of the invention provides an isolated antibody as described above, further comprising a light chain variable region selected from:
a) a light chain variable region comprising:
  (i) a light chain CDR1 of SEQ ID NO: 21 or a variant thereof wherein 1, 2, or 3 amino acids of said light chain CDR1 is substituted by a different amino acid;
  (ii) a light chain CDR2 of SEQ ID NO: 22 or a variant thereof wherein 1, 2, or 3 amino acids of said light chain CDR2 is substituted by a different amino acid;
  (iii) a light chain CDR3 of SEQ ID NO: 23 or a variant thereof wherein 1, 2, or 3 amino acids of said light chain CDR3 is substituted by a different amino acid, or
b) a light chain variable region comprising:
  (i) a light chain CDR1 of SEQ ID NO: 26 or a variant thereof wherein 1, 2, or 3 amino acids of said light chain CDR1 is substituted by a different amino acid;
  (ii) a light chain CDR2 of SEQ ID NO: 27 or a variant thereof wherein 1, 2, or 3 amino acids of said light chain CDR2 is substituted by a different amino acid;
  (iii) a light chain CDR3 of SEQ ID NO: 28 or a variant thereof wherein 1, 2, or 3 amino acids of said light chain CDR3 is substituted by a different amino acid.

A third aspect of the invention relates to an isolated nucleic acid molecule encoding an antibody or antigen-binding fragment thereof as described herewith.

A fourth and fifth aspects of the invention relate to a recombinant expression vector comprising said nucleic acid molecule, and to a host cell comprising said recombinant vector, respectively.

A sixth aspect of the invention relates to a process for producing antibodies or fragments thereof as described herewith comprising culturing a host cell transformed with an expression vector comprising a nucleic acid sequence that encodes said antibodies or fragments thereof under conditions sufficient to promote expression of said antibodies or fragments thereof.

A seventh aspect of the invention provides a pharmaceutical composition comprising one or more of (i) an antibody specific for MMP9 or antigen-binding fragment thereof, (ii) a nucleic acid sequence, (iii) a vector, and/or (iv) a host cell, as described herewith, and at least one pharmaceutically acceptable carrier.

An eighth aspect of the invention relates to an imaging composition or a diagnosis composition comprising one or more anti-MMP9 antibody or antigen-binding fragment thereof as described herewith.

A ninth aspect of the invention is a kit comprising one or more anti-MMP9 antibody or antigen-binding fragment thereof as described herewith.

A tenth aspect of the invention relates to an antibody or formulation thereof according to the invention for use in the prevention and/or treatment of a MMP9 related disorder, such as an inflammatory and/or autoimmune disease or a cancer or tumor or a fibrotic disease.

An eleventh aspect relates to a method of preventing and/or treating a MMP9 related disorder, such as an inflammatory and/or autoimmune disease or a cancer or a fibrotic disease comprising administering in a subject in need thereof a therapeutically effective amount of said antibody or fragment thereof or said pharmaceutical composition.

A further aspect of the invention relates to an anti-MMP-9 antibody of the invention or a formulation thereof for use as a medicament.

Other features and advantages of the invention will be apparent from the following detailed description.

DESCRIPTION OF THE FIGURES

FIG. 2 shows alignment of amino acid sequences of human (SEQ ID NO: 1), Cynomologus monkey (SEQ ID NO: 75), rat (SEQ ID NO: 76) and mouse (SEQ ID NO: 77) MMP9. (*) indicates positions which have a single, fully conserved residue, (:) indicates conservation between groups of strongly similar properties—scoring >0.5 in the Gonnet PAM 250 matrix, (.) indicates conservation between groups of weakly similar properties—scoring ≤0.5 in the Gonnet PAM 250 matrix.

FIG. 3 shows sequence alignment of exemplary human heavy chain antibody fragments comprising the human heavy chain constant region and the human heavy chain variable region of anti-MMP9 antibodies according to the invention. Heavy chain antibody fragment sequences are labelled with the sequence name of the variable heavy chain region included with * before name: *F20-VH (SEQ ID NO: 78), *F20-VH-GL1 (SEQ ID NO: 79), *F20-VH-GL1-V1-V9 (SEQ ID NO: 71). *F20-VII-GL1-V1-V9-V14 (SEQ ID NO: 72), *F20-VH-GL1-V4-V9 (SEQ ID NO: 73), *F20-VH-GL1-V4-V9-V14 (SEQ ID NO: 74). CDRs are underlined. Annotations are identical to the ones described in FIG. 2.

FIG. 4 shows sequence alignment of exemplary human light chain antibody fragments comprising the human light chain constant region and the human light chain variable region of anti-MMP9 antibodies according to the invention. Light chain antibody fragment sequences are labelled with the sequence name of the variable light chain region included with * before name: *B03-VL (SEQ ID NO: 80), *B03-VL-GL1 (SEQ ID NO: 81). CDRs are underlined. Annotations are identical to the ones described in FIG. 2.

FIG. 5 shows sequence alignment of exemplary human light chain antibody fragments comprising the human light chain constant region and the human light chain variable region of anti-MMP9 antibodies according to the invention. Light chain antibody fragment sequences are labelled with the sequence name of the variable light chain region included with * before name: *B08-VL (SEQ ID NO: 82), *B08-VL-GL6 (SEQ ID NO: 83). CDRs are underlined. Annotations are identical to the ones described in FIG. 2.

FIG. 16 shows representative cross-sections of mouse intestinal explanted grafts stained with Sirius red and quantification of collagen layer thickness. Freshly isolated small bowel resection (A and B). Day 14 after transplantation in isotype control-treated mice (C and D). Day 14 after transplantation in anti-MMP9 antibody-treated mice (F20-VH/B08-VLc variant) (E and F). Transmission light (A, C and E), polarized light (B, D and F). (G) Quantification of collagen layer thickness in heterotopic intestinal grafts from anti-MMP9- or isotype control-treated mice. Means and SD of collagen layer thickness from sections of transplants are reported for both groups of treated mice (72 sections for F20-VH/B08-VLc; 64 sections for isotype control). Statistical comparisons of group data (F20-VH/B08-VLc versus isotype control) were performed using two-way, unpaired T test, using Graph Pad Prism. ***p<0.0001.

DETAILED DESCRIPTION OF THE INVENTION

Definitions

Figure 1:
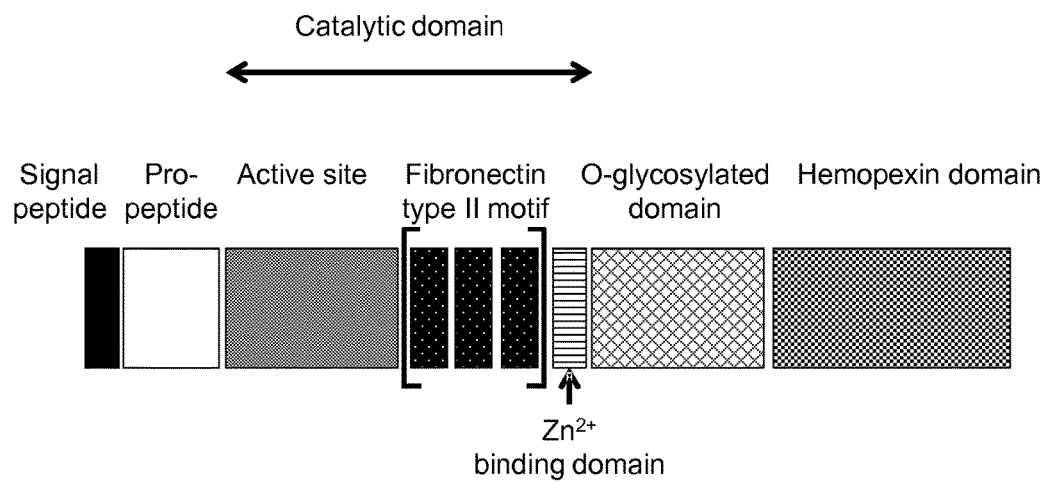
FIG. 1 shows a schematic diagram of the molecular domain structure of the human MMP9 protein. Numbers indicate amino acid positions on the immature MMP9 protein amino acid sequence.

The term "Matrix metalloproteinase 9", abbreviated "MMP9", also known as 92 kDa type IV collagenase, 92 kDa gelatinase or gelatinase B (GELB), is an enzyme that, in humans, is encoded by the MMP9 gene whose sequence is disclosed under NCBI accession number ENSG00000100985. The form of human MMP9 comprises a sequence of 707 amino acids in total, available under NCBI accession number NP_004985.2 (SEQ ID NO: 1). The general domain structure of MMP9 comprises a secretory leader sequence (residues 1-19 on SEQ ID NO: 1), an inhibitory pro-domain required for catalytic latency (residues 20-106 on SEQ ID NO: 1), a 'split' catalytic domain (residues 107-441 on SEQ ID NO: 1) containing three fibronectin type II-like repeat loops that together form a collagen binding domain (CBD), a hyperglycosylated proline-rich linker (also referred to as the OG domain) (residues 442-520 on SEQ ID NO: 1), and a hemopexin-like repeat C-terminal domain (PEX) (residues 521-707 on SEQ ID NO: 1) (Rowsell et al., 2002, *J Mol Biol* 319:173-81) (FIG. 1). MMP9 is secreted and maintained as an inactive, latent form by a pro-domain. Proteolytic removal of the pro-domain activates the enzymatic activity of MMP9, and then MMP9 can be referred to as "active MMP9". Its catalytic domain contains a gelatin-binding region, which provides specific affinity for gelatin. In addition to gelatin, MMP9 has various substrates including collagens (e.g. collagen IV, and collagen V), elastin, galectin3, entactin and ICAM-1 (Ram et al, 2006, *J. Clin. Immunol.* 26, 299-307), and cytokines and chemokines (Opdenakker et al, *Trends Immunol.* 2001: 22:527-81).

The term "antibody" as referred to herein designates a polypeptide that binds to an antigen. This includes whole antibodies and any antigen binding fragments. The term "antibody" is used in its broadest sense and includes monoclonal antibodies, polyclonal antibodies, human antibodies, humanized antibodies, chimeric antibodies, and further engineered antibodies as long as the characteristic properties of the invention are retained, in particular the ability of binding to the target antigen, more specifically to the same epitope of MMP9 as the one recognized by the antibodies of the invention. Examples of antibodies and fragments thereof include a variable domain fragment ("Fv", consisting of the VH and VL domains of a single arm of an antibody), Fab fragment (monovalent fragment consisting of the VH, VL, CH1 and CL domains), $Fab_2$ fragment (bivalent), $Fab_3$ fragment (trivalent), Fab' fragment (Fab with hinge region), $F(ab')_2$ fragment (bivalent fragment including two Fab fragments linked by a disulfide bridge at the hinge region), Fd fragment (consisting of the VH and CH1 domains), rIgG (reduced IgG or half-IgG), diabodies, triabodies, tetrabodies, minibodies, monovalent antibodies, divalent or multivalent antibodies comprising a fragment of more than one antibody, single chain variable fragment (ScFv), bis-scFv (bispecific), and derivatives of antibodies such as disulfide stabilized Fv fragments, CDR-comprising peptides, as well as epitope-binding fragments of any of the above (Holliger and Hudson, 2005, *Nature Biotechnology*, 23(9): 1126-1136). An antibody refers to a glycoprotein comprising at least two heavy (H) chains and two light (L) chains interconnected by disulfide bonds, or an antigen-binding fragment thereof. Each heavy chain comprises a heavy chain variable region (VH) and a heavy chain constant region (CH). Each light chain comprises a light chain variable region (VL) and a light chain constant region (CL). In mammalians, the heavy chain can either be alpha ($\alpha$), delta ($\delta$), epsilon ($\epsilon$), gamma ($\gamma$) or mu ($\mu$), which defines the class of antibody IgA, IgD, IgE, IgG and IgM, respectively. In mammalians, the light chain can either be lambda ($\lambda$) or kappa ($\kappa$). In mammalians, depending on the class of antibody, the heavy chain constant region comprises three immunoglobulin domains, CH1, CH2, and CH3 (for IgA, IgD, IgG) or four immunoglobulin domains, CH1, CH2, CH3, and CH4 (for IgE and IgM). The light chain constant region comprises one immunoglobulin domain, CL. An antibody can have the structure of an IgA, IgG, IgE, IgD and IgM as well as any subtype thereof. Antibodies may be from any source including in particular primate (human and non-human primate) and primatized sources.

The term "variable domain" or "variable region" (variable domain of a light chain (VL), variable domain of a heavy chain (VH) as used herein refers to each of the pair of light and heavy chain domains which are involved directly in binding the antibody to the antigen. The variable light and heavy chain domains have the same general structure and each domain comprises four framework ("FR") regions whose sequences are widely conserved, connected by three "hypervariable regions" called "complementary determining regions" or "CDRs". The framework regions adopt a β-sheet conformation and the CDRs may form loops connecting the β-sheet structure. The CDRs in each chain are held in their three-dimensional structure by the framework regions and form together with the CDRs from the other chain the antigen binding site. The term "antigen-binding portion of an antibody" when used herein refers to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus: the domains FR1, CDR1, FR2, CDR2, FR3, CDR3, and FR4. The residues of the CDR and FR regions are conventionally numbered according to the standard definition of Kabat et al (*Sequences of Proteins of Immunological Interest, 5th ed.*, Public Health Service, National Institutes of Health, Bethesda, Md. (1991), Publication No. 91-3242). This numbering system is used in the present specification except where otherwise indicated. The Kabat residue designations do not always correspond directly to the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35 (CDR-H1), residues 50-65 (CDR-H2) and residues 95-102 (CDR-H3) according to the Kabat numbering system. The CDRs of the light chain variable domain are located at residues 24-34 (CDR-L1), residues 50-56 (CDR-L2) and residues 89-97 (CDR-L3) according to the Kabat numbering system.

In the present application, unless specified otherwise, for all human immunoglobulin heavy and light chain variable domains, numbering is according to the "Kabat numbering system" (*Sequences of Proteins of Immunological Interest, 5th ed.*, Public Health Service, National Institutes of Health, Bethesda, Md. (1991), Publication No. 91-3242).

In the present application, unless specified otherwise, for all human immunoglobulin heavy chain constant domains, numbering is according to the "EU numbering system" (Edelman et al, 1969, *Proc Natl Acad Sci*, 63(1): 78-85).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

The term "chimeric antibody" generally refers to an antibody comprising a variable region from one source or species and at least a portion of a constant region derived from a different source or species, usually prepared by recombinant DNA techniques. A typical example of chimeric antibodies includes those comprising a murine variable region and a human constant region. As defined herewith this term also includes an antibody comprising at least one of the CDRs of a first human antibody and at least a portion of a constant region of a second human antibody. It also includes an antibody comprising heavy chain CDR1, CDR2, and CDR3 of a first human antibody and light chain CDR1, CDR2, and CDR3 of a second human antibody.

The term "humanized antibody" designates antibodies from a non-human species having one or more complementarity determining regions (CDRs) from said non-human species and a framework region from a human immunoglobulin molecule. Humanized antibodies may optionally further comprise one or more framework residues derived from the non-human species from which the CDRs were derived.

The term "human antibody" or "fully human antibody" refers to antibodies in which the variable regions and the constant regions of both the heavy and the light chains are all of human origin, or substantially identical to sequences of human origin, but not necessarily from the same antibody.

The term "isolated antibody" refers to an antibody that has been separated from a component of its natural environment. For instance, an isolated antibody has been purified to greater than 95% or 99% purity as determined by methods in the art (see e.g. Flatman et al, 2007, *J Chromatogr B Analyt Technol Biomed Life Sci*, 848: 79-87) including electrophoretic (e.g. SDS-PAGE, isoelectric focusing, capillary electrophoresis) or chromatographic (e.g. ion exchange or reverse phase HPLC (high performance liquid chromatography) methods.

The terms "polynucleotide" or "nucleic acid molecule" refers to a polymer comprising nucleotides. Examples of nucleic acid molecules include DNA, RNA, locked nucleic acid (LNA), complementary DNA (cDNA).

"Polypeptide" is understood as a peptide, an oligopeptide, an oligomer or a protein comprising at least two amino acids joined to each other by a normal or modified peptide bond, such as in the cases of the isosteric peptides, for example. A polypeptide can be composed of amino acids other than the 20 amino acids defined by the genetic code. A polypeptide can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the lateral chain or even at the carboxy- or amino-terminal ends. For example, polypeptide modifications is understood to include acetylation, acylation, ADP-ribosylation, amidation, covalent fixation of flavine, covalent fixation of heme, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, cysteine formation, pyroglutamate formation, formylation, gamma-carboxylation, glycosylation including pegylation, GPI anchor formation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature (*Proteins Structure and Molecular Properties* (1993) 2$^{nd}$ Ed., T. E. Creighton, New York; *Post-translational Covalent Modifications of Proteins* (1983) B. C. Johnson, Ed., Academic Press, New York; Seifter et al. (1990) *Analysis for protein modifications and nonprotein cofactors, Meth. Enzymol.* 182: 626-646 and Rattan et al., (1992) *Protein Synthesis: Post-translational Modifications and Aging, Ann NY Acad Sci*, 663: 48-62).

"Isolated polynucleotide" or "isolated polypeptide" is understood as a polynucleotide or a polypeptide such as previously defined which is isolated from the human body or otherwise produced by a technical process.

The term "variant" can apply to a polynucleotide and/or a polypeptide. For instance, a variant of a peptide or polypeptide, as referred to herein means a peptide or polypeptide substantially homologous to the referenced peptide sequence, but which has an amino acid sequence different from that of the referenced sequence because of one or more amino acid deletions, insertions and/or substitutions. Substantially homologous means a variant amino acid sequence which is identical to the referenced peptide sequence except for the deletion, insertion and/or substitution of a few amino acids, e.g. 1, 2, 3, 4, 5, or 6 amino acids. Substantially homologous means a variant amino acid sequence that is at least 80%, at least 85%, at least 90%, at least 95%, at least 96%, at least 97%, at least 98% or at least 99% identical to the referenced amino acid sequence. A variant nucleic acid sequence can be at least 80%, at least 85%, at least 90%, at least 95%, at least 96%, at least 97%, at least 98% or at least 99% identical to the referenced nucleic acid sequence. The identity of two amino acid sequences or of two nucleic acid sequences can be determined by visual inspection and/or mathematical calculation, or more easily by comparing sequence information using known computer program used for sequence comparison such as Clustal package version 1.83. A variant may comprise a sequence having at least one conservatively substituted amino acid, meaning that a given amino acid residue is replaced by a residue having similar physiochemical characteristics. Generally, substitutions for one or more amino acids present in the original polypeptide should be made conservatively. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known (Kyte, et al, 1982, *J. Mol. Biol.*, 157: 105-131). For example, a "conservative amino acid substitution" may involve a substitution of a native amino acid residue with a non-native residue such that there is little or no effect on the polarity or charge of the amino acid residue at that position. Desired amino acid substitutions (whether conservative or non-conservative) can be determined by those skilled in the art at the time such substitutions are desired. Exemplary amino acid substitutions are presented in Table 1 below. The term "variant" also includes a peptide or polypeptide substantially homologous to the referenced peptide sequence, but which has an amino acid sequence different from that of the referenced sequence because one or more amino acids have been chemically modified or substituted by amino acids analogs. This term also includes glycosylated polypeptides.

TABLE 1

| Original residues | Examples of substitutions |
|---|---|
| Ala (A) | Val, Leu, Ile |
| Arg (R) | Lys, Gln, Asn |
| Asn (N) | Gln |
| Asp (D) | Glu |
| Cys (C) | Ser, Ala |
| Gln (Q) | Asn |
| Glu (E) | Asp |
| Gly (G) | Pro, Ala |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Ile, Phe |
| Phe (F) | Leu, Val, Ile, Ala, Tyr |
| Pro (P) | Ala, Gly |
| Ser (S) | Thr, Ala, Cys |
| Trp (W) | Phe, Tyr |
| Thr (T) | Ser |

TABLE 1-continued

| Original residues | Examples of substitutions |
| --- | --- |
| Tyr (Y) | Trp, Phe, Thr, Ser |
| Val (V) | Ile, Met, Leu, Phe, Ala |

The term "epitope" includes any antigenic determinant capable of specific binding to an antibody or antigen binding fragment thereof. In certain embodiments, epitope determinant includes chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody. Some epitopes comprise discontinuous sections of the antigen's amino acid sequence, where non-contiguous amino acids are positioned close to each other's by the spatial configuration of the antigen ("conformational epitopes") or comprise a section of contiguous amino acids on the antigen's amino acid sequence ("linear epitopes").

As used herewith the term "bind" or "binding" of an antibody to a target antigen means an at least temporary interaction or association of said antibody with, or to, said target antigen (such as MMP9) or with, or to, fragments of said target antigen comprising an epitope recognized by said antibody.

The terms "selectively binds", "specifically binds", "specific for", when applied to an antibody, indicate that the antibody preferentially recognizes and/or binds the target polypeptide or epitope, i.e. with a higher affinity than to any other antigen or epitope, i.e. the binding to the target polypeptide can be discriminated from non-specific binding to other antigens. The binding affinity of an antibody can be readily determined by one of ordinary skill in the art, for example, by Scatchard analysis (Scatchard et al., 1949, *Ann. N.Y. Acad.* 1949. 51, 660-672).

As used herein, "binding affinity" generally refers to the apparent association constant or "Ka". The Ka is the reciprocal of the dissociation constant "Kd". Binding affinity may be determined by a variety of methods including equilibrium dialysis, equilibrium binding, gel filtration, ELISA, surface plasmon resonance or spectroscopy (e.g. using a fluorescence assay). Exemplary conditions for evaluating binding affinity are in TRIS-buffer (50 mM Tris-HCl, 150 mM NaCl, 5 mM $CaCl_2$ at pH 7.5). These techniques can be used to measure the concentrations of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation: [Bound]=N×([Free])/((1/Ka)+[Free]). Comparison of affinity between two antibodies can be established without actually determining the Ka value for each antibody, but based on a quantitative measurement of affinity (e.g. by ELISA or FACS analysis) that is proportional to Ka or a qualitative measurement of affinity or an inference of affinity (e.g. in functional assay or in vitro or in vivo assay).

The term "blocking" or "neutralizing" activity of an antibody refers to its ability to inhibit its target's activity. Applied to an antibody binding to MMP9, this term refers to the antibody's ability to generally neutralize MMP9 activity, by inhibiting activation of proMMP9 and/or by inhibiting the catalytic activity of activated MMP9 on one of its substrate such as gelatin, for instance as described in the example section. The neutralizing activity of an anti-MMP9 antibody may be determined by cell-free in vitro assays, or in vivo assays or in vitro functional assays such as a human cancer cell line invasion assay. In a human cancer cell line invasion transwell assay, cancer cells degrade and migrate through a basal membrane matrix (Matrigel®), thus mimicking the in vivo process of tumor cell intravasation at nearby blood vessels and extravasation and invasion into a distant tissue.

The "potency" of an antibody may be expressed as the concentration of antibody/antigen-binding fragment which produces the half-maximal effect at a given antigen concentration. For example, the "effect" of an antibody may be inhibition or neutralization of its target's activity. In this case, the antibody concentration producing the half-maximal inhibition is referred to as $IC_{50}$, which is given in mol/l or M. Potency is usually influenced by affinity until, at a given antigen concentration, an affinity is reached beyond which further improvements in affinity will not enhance binding of the antigen anymore (so-called potency ceiling). Applied to an antibody against MMP9, potency may, for example, be determined by measuring the $IC_{50}$ value of MMP9 dependent digestion of gelatin substrate in presence of the antibody.

The term "efficacy of inhibition" or "efficacy of neutralization", applied to a neutralizing antibody, is a measure of effectiveness of said antibody in inhibiting a specific biological or biochemical function expressed as a percentage of potential total inhibition of the biological or biochemical activity which is normalized to 100%. Applied to an antibody binding to MMP9, 100% efficacy may, for example, be antibody-mediated total inhibition of MMP9-dependent digestion of a gelatin substrate. The term antibody "effector function" as used herein includes a biochemical event that results from the interaction of an antibody Fc region with an Fc receptor or ligand. Effector functions include FcγR-mediated effector functions such as ADCC (antibody dependent cell-mediated cytotoxicity) and ADCP (antibody dependent cell-mediated phagocytosis), and complement-mediated effector functions such as CDC (complement dependent cytotoxicity). An effector function of an antibody may be altered by altering, i.e. enhancing or reducing, preferably enhancing, the affinity of the antibody for an effector molecule such as an Fc receptor or a complement component. Binding affinity of an antibody Fc region with an Fc receptor or ligand can be altered by modifying the effector molecule binding site. It is also possible that an alteration in the binding site on the antibody for the effector molecule alters the geometry of the interaction without significantly altering the overall binding affinity, rendering the effector mechanism ineffective as in non-productive binding. It is also possible to alter an effector function by modifying a site not directly involved in effector molecule binding, but otherwise involved in performance of the effector function. By altering an effector function of an antibody it may be possible to control various aspects of the immune response, e.g. enhancing or suppressing various reactions of the immune system, with possible beneficial effects in diagnosis and therapy.

The term "pharmaceutically acceptable" refers to a carrier comprised of a material that is not biologically or otherwise undesirable.

The term "carrier" refers to any components present in a pharmaceutical formulation other than the active agent and thus includes diluents, binders, lubricants, disintegrants, fillers, coloring agents, wetting or emulsifying agents, pH buffering agents, preservatives and the like.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it for example based on familial history; (b) inhibiting the disease, i.e., arresting its development; or (c) relieving the disease, i.e., causing regression of the disease and/or its symptoms or conditions such as improvement or remediation of damage. For instance, treatment of inflammatory bowel disease comprises preventing, decreasing or even eradicating the symptoms of the diseases or disorders, for instance partial or total alleviation of diarrhea, abdominal pain and cramping, blood in the stool, abscess, ulcers and fistulas.

"MMP9-related diseases", as defined herewith, designate diseases mediated or influenced, at least in part, by the expression and/or activity of MMP9. Examples of MMP9-related diseases include inflammatory and autoimmune diseases, cancers or tumors, lung diseases, fibrotic diseases such as fibrotic lung diseases, septicemia, muscular dystrophy, allergy, renal fibrosis, scleroderma, dilated cardiomyopathy, Chagas disease, cardiovascular diseases, neuropsychiatric disorders, diabetes, and eye diseases.

The terms "inflammatory and autoimmune diseases" are generally defined herewith as inflammatory abnormalities which may or may not involve the immune system and diseases or disorders arising from an abnormal immune response of the subject's body against substances and tissues normally present in the body, respectively. Non-limitative examples of inflammatory and autoimmune diseases include mostly inflammatory bowel diseases (IBD) including Crohn's disease (CD) (in particular penetrating and stricturing Crohn's disease), ulcerative colitis (UC), indeterminate colitis, collagenous colitis, rheumatoid arthritis (RA), multiple sclerosis (MS), systemic lupus erythematosus (SLE), Sjogren's syndrome, systemic sclerosis, polymyositis, atherosclerosis.

The term "inflammatory bowel disease" (IBD) is defined herewith as disease involving chronic inflammation of all or part of digestive tract. Non-limitative examples of IBD include Crohn's disease, in particular non-penetrating and stricturing Crohn's disease, penetrating and stricturing Crohn's disease, and fistulizing Crohn's disease, ulcerative colitis (UC), indeterminate colitis, collagenous colitis, lymphocytic colitis and intestinal fibrosis. Crohn's disease (CD) is defined as a disease of transmural inflammation with skip lesions that may involve any part of the GI tract from mouth to anus. Ulcerative colitis is a disease of mucosal inflammation limited to the colon.

The terms "cancers" or "tumors" as defined herewith, are diseases involving abnormal cell growth with the potential to invade or spread to other parts of the body. Term "cancers" designate diseases exemplified by, but not limited to, haematopoetic cancer, brain cancer, breast cancer, colorectal cancer, head and neck cancer, pancreatic cancer, ovarian cancer, urinary bladder cancer, lung cancer, liver cancer, melanoma, prostate cancer, muscle cancer, mesenchymal cancer, esophagogastric adenocarcinoma, non-small lung cancer, lung squamous cell carcinoma, lung adenocarcinoma, gastric adenocarcinoma, pancreatic adenocarcinoma, hepatocellular carcinomacolorectal cancer. hepatocellular carcinoma, and colorectal cancer.

The term "lung disease" designates diseases exemplified by, but not limited to, asthma, fibrotic lung diseases such as idiopathic pulmonary, chronic obstructive pulmonary disease (COPD) and rhinitis.

The term "fibrotic diseases" is defined herewith as a disease wherein affected tissues present with an excessive accumulation of fibrous connective tissue (components of the extracellular matrix such as collagen and fibronectin) in and around inflamed or damaged tissue, which can lead to permanent scarring, organ malfunction and, ultimately, death, as seen in end-stage liver disease, kidney disease, idiopathic pulmonary fibrosis (IPF) and heart failure. Non-limitative examples of fibrotic diseases include systemic sclerosis, multifocal fibrosclerosis, sclerodermatous graft versus host disease in bone marrow transplant recipients, nephrogenic systemic fibrosis, pulmonary fibrosis, liver fibrosis, kidney fibrosis, rheumatoid arthritis, Crohn's disease, ulcerative colitis, myelofibrosis and systemic lupus erythematosus.

The terms "ocular conditions" or "eye diseases" are defined herewith as diseases of the eyes associated with progressive degeneration of the retinal pigment epithelium and photoreceptors leading to visual loss or/and diseases of the eyes associated with damage to the blood vessels of the retina. Non-limitative examples of ocular conditions include fibrotic pathologies of the lens, corneal diseases, diabetic retinopathy, "dry" or "wet" age-related macular degeneration, proliferative vitreoretinopathy, cataract formation, pterygia, keratoconus, age-related macular degeneration and diabetic retinopathy.

The term "cardiovascular diseases" is defined herewith as diseases of cardiovascular system that involve inflammation, altered tissue remodelling with increase in collagen and accumulation of fibrotic scar in myocardial infarction. Non-limitative examples of cardiovascular diseases include hypertension, pulmonary hypertension, pulmonary or tricuspid valve disease, aortic and mitral valve disease, aortic coarctation, atherosclerosis, myocardial infarction, heart failure, ischemic cardiomyopathy, dilated cardiomyopathy, chronic arrhythmia, cardiac fibrosis and coronary artery disease.

The terms "neurological disorders" or "neuropsychiatric disorders" are defined herewith as diseases characterized by neuronal dysfunction and neuronal cell death, which lead to incurable and often fatal functional deficits. Non-limitative examples of neurological disorders include amyotrophic lateral sclerosis, Alzheimer's disease, multiple sclerosis, neuroinflammation, cerebral ischemia and neuropathic pain.

The term "subject" as used herein refers to mammals. For example, mammals contemplated by the present invention include human, primates, domesticated animals such as cattle, sheep, pigs, horses, laboratory rodents and the like.

The term "efficacy" of a treatment or method according to the invention can be measured based on changes in the course of disease or condition in response to a use or a method according to the invention. For example, the efficacy of a treatment or method according to the invention can be measured by its impact on signs or symptoms of illness. A response is achieved when the patient experiences partial or total alleviation, or reduction of unwanted symptoms of illness.

The term "effective amount" as used herein refers to an amount of at least one antibody according to the invention, or a pharmaceutical formulation thereof, that elicits a detectable reduction of the symptoms of the disease in a subject that is being administered said antibody, these symptoms can include, for instance: a) diarrhea, abdominal pain and cramping, blood in the stool, abscess, ulcers and fistulas, in the case of inflammatory bowel disease or b) constipation or diarrhea, bright red or dark red blood in stools, weight loss, fatigue, nausea and anemia, in the case of colorectal cancer.

MMP9 Binding Proteins

General Characteristics of the MMP9 Binding Proteins

In a first aspect, the present invention provides proteins that bind to MMP9, in particular human MMP9, or a fragment thereof, and comprise at least one fragment of a heavy chain variable region and/or at least one fragment of a light chain variable region of an antibody as described herewith.

In one embodiment of the invention are provided isolated antibodies specific for MMP9, in particular human MMP9, or antigen-binding fragments thereof, comprising at least one fragment of a heavy chain variable region and at least one fragment of a light chain variable region, and optionally at least one fragment of a constant region, as described herewith.

In an alternative embodiment of the invention are provided isolated antibodies specific for MMP9, in particular human MMP9, or antigen-binding fragments thereof, characterized by their binding to an epitope on MMP9, as described herewith.

The protein to which the antibodies according to the invention, or fragments thereof, bind can be the MMP9 protein of any species.

The antibodies according to the present invention generally exhibit a high specificity for human MMP9. However, depending on the degree of sequence identity between MMP9 homologs of different species (see FIG. 2), a given antibody or antigen-binding fragment may show cross-reactivity with MMP9 from at least one other species, e.g. mouse, rat, marmoset, monkey (e.g. Cynomologus monkey), dog, and/or rabbit. For antibodies directed towards human MMP9, some level of cross-reactivity with other mammalian forms of MMP9 may be desirable in certain circumstances, for example when testing antibodies in animal models of a particular disease or for conducting toxicology, safety and dosage studies.

In a specific embodiment, the antibodies according to the invention or fragments thereof bind preferentially to human MMP9.

In another embodiment, the antibodies according to the invention or fragments thereof show cross-reactivity with human MMP9, Cynomologus monkey MMP9, rat MMP9 and, optionally, mouse MMP9.

In some embodiments, the binding affinity (e.g. inversely correlated to the Kd value) of antibodies, and fragments thereof, according to the invention for human MMP9 is at least 2 times, at least 5 times, at least 10 times, at least 50 times, at least 100 times, at least 500 times, or at least 1000 times higher than their binding affinity for a non-human MMP9.

In one embodiment, the antibodies according to the invention or fragments thereof bind preferentially to MMP9 and, optionally, additionally exhibit a weak binding, or virtually no binding (i.e. negligible or not detectable binding) to other matrix metalloproteinases (MMPs) such as MMP1, MMP2, MMP3, MMP7, MMP8, MMP9, MMP10, MMP12, MMP13, MMP14, MMP16, MMP17, MMP19.

In a particular embodiment, the antibodies according to the invention, or fragments thereof, bind preferentially to MMP9 and exhibit a weak, or virtually no (i.e. negligible or not detectable), binding to MMP2.

For therapeutic uses, it may be advantageous that the antibodies according to the invention, or fragments thereof, do not bind, and thus do not neutralize, MMP2 so as not to substantially affect MMP2 activity. Indeed, MMP2 is required for normal tissue homeostasis and may also have a protective role against disease as suggested by observations according to which MMP2 knockout mice show a worsen phenotype than wild-type mice, in several disease models (Grag et al., 2006, *J. Immunol.*, 177(6):4103-12).

In some embodiments, the binding affinity of antibodies (e.g. inversely correlated to the equilibrium dissociation constant Kd value), and fragments thereof, according to the invention for MMP9 is at least 2 times, at least 5 times, at least 10 times, at least 50 times, at least 100 times, at least 500 times, or at least 1000 times higher than their binding affinity for MMP2.

Binding affinity can be measured by any method known in the art including equilibrium dialysis, equilibrium binding, gel filtration, ELISA, surface plasmon resonance or spectroscopy (e.g. using a fluorescence assay) (Jiang et al. *BMC Pharmacology* 2010, 10:10) and can be expressed as, for instance, on-rate, off-rate, dissociation constant (Kd), equilibrium constant (Keq) or any other term used in the art.

In some embodiments, the antibodies, and fragments thereof, according to the invention specifically bind to human MMP9 with a dissociation constant (Kd) equal to or lower than 100 nM, in particular lower than 10 nM, more particularly lower 1 nM, or lower than 0.5 nM, or lower than 0.1 nM, or lower than 0.01 nM, or lower than 0.005 nM.

The protein to which the antibodies according to the invention, or fragments thereof, bind to is any form of MMP9: the immature protein comprising the secretory leader sequence ("preproenzyme") (corresponding to residues 1-707 of SEQ ID NO: 1 in the case of human MMP9), the mature latent MMP9 lacking the secretory leader sequence ("proenzyme") (corresponding to residues 20-707 of SEQ ID NO: 1 in the case of human MMP9), the "activated enzyme" (corresponding to residues 107-707 of SEQ ID NO: 1 in the case of human MMP9), or any fragment of MMP9.

The antibodies according to the invention, or fragments thereof, can bind to MMP9 by interacting with an epitope comprising amino acids located anywhere in the protein, e.g. in the prodomain, the catalytic domain, in particular in the Fn-repeats or the OG domain linker, the recognized amino acids being located at one or more sites within the protein.

In a particular embodiment, the antibodies according to the invention, or antigen-binding fragments thereof, bind to MMP9 by interacting with an epitope comprising amino acids located in the catalytic domain of MMP9, in particular human MMP9.

In a more particular embodiment, the antibodies according to the invention, or antigen-binding fragments thereof, bind to MMP9 by interacting with an epitope comprising at least one amino acid within a region consisting of SEQ ID NO: 41, at least one amino acid within a region consisting of SEQ ID NO: 42, and at least one amino acid within a region consisting of SEQ ID NO: 43, located in the catalytic domain of human MMP9.

In a still more particular embodiment, the antibodies according to the invention, or antigen-binding fragments thereof, bind to MMP9 by interacting with an epitope comprising the amino acids of a region consisting of SEQ ID NO: 41, the amino acids of a region consisting of SEQ ID NO: 42, and the amino acids of a region consisting of SEQ ID NO: 43, located in the catalytic domain of human MMP9.

In a further particular embodiment, the antibodies according to the invention, or antigen-binding fragments thereof, bind to MMP9 by interacting with an epitope comprising at least one, at least two, at least three, at least four, or at least five amino acids of a region consisting of SEQ ID NO: 41, at least one, at least two, at least three, at least four, or at least five amino acids of a region consisting of SEQ ID NO: 42, and at least one, at least two, at least three, at least four, or at least five amino acids of a region consisting of SEQ ID NO: 43, located in the catalytic domain of human MMP9. Therefore, in one embodiment, the antibodies according to the invention, or fragments thereof, not only bind to MMP9 but also neutralize or inhibit MMP9 activity (e.g. MMP9 catalytic activity) by inhibiting processing of the preproenzyme and/or proenzyme to the catalytically active enzyme and/or by inhibiting the proteolytic activity of the activated enzyme.

In a particular embodiment, the antibodies according to the invention, or fragments thereof, not only bind to MMP9 but also neutralize or inhibit MMP9 activity (e.g. MMP9 catalytic activity) by inhibiting the proteolytic activity of the activated MMP9 enzyme.

In a particular embodiment, the antibodies according to the present invention exhibit a high specificity and inhibitory activity for human MMP9 and may show cross-reactivity with Cynomologus monkey (*Macaca fascicularis*) MMP9, rat MMP9, and/or mouse MMP9.

In a particular embodiment, the antibodies according to the invention or fragments thereof inhibit MMP9 activity and, optionally, additionally exhibit a weak inhibitory activity, or virtually no inhibitory activity (i.e. negligible or not detectable activity) towards other matrix metalloproteinases (MMPs) such as MMP1, MMP2, MMP3, MMP7, MMP8, MMP9, MMP10, MMP12, MMP13, MMP14, MMP16, MMP17, MMP19.

In a particular embodiment, the antibodies according to the invention, or fragments thereof, exhibit a neutralizing activity towards MMP9 and a weak, or virtually no (i.e. negligible or not detectable), neutralizing activity towards MMP2.

The ability of an antibody to block or neutralize the activity of its target protein can be evaluated by its potency as defined herewith, which is itself reflected, for instance, by the $IC_{50}$ value. Typically, the neutralizing activity of an anti-MMP9 antibody may be determined by cell-free in vitro assays, or in vivo assays or in vitro functional assays such as a human cancer cell line invasion assay. In a human cancer cell line invasion transwell assay, cancer cells degrade and migrate through a basal membrane matrix (Matrigel®), thus mimicking the in vivo process of tumor cell intravasation at nearby blood vessels and extravasation and invasion into a distant tissue.

In some embodiments, the inhibitory or neutralizing potency (e.g. inversely correlated to the $IC_{50}$ value) of antibodies, and fragments thereof, according to the invention for human MMP9 is at least 2 times, at least 5 times, at least 10 times, at least 50 times, at least 100 times, at least 500 times, or at least 1000 times higher than their neutralizing potency for non-human MMP9.

In some embodiments, the inhibitory or neutralizing potency e.g. inversely correlated to the $IC_{50}$ value, of antibodies, and fragments thereof, according to the invention on MMP9 is at least 10 times, at least 50 times, at least 100 times, at least 500 times, at least 1000 times higher than their inhibitory or neutralizing potency on MMP2.

In some embodiments, the antibodies, and fragments thereof, according to the invention have a $IC_{50}$ equal to or lower than 100 nM, in particular lower than 50 nM, more particularly lower than 20 nM, lower than 10 nM, lower than 8 nM, lower than 7 nM, lower than 6 nM, lower than 5 nM, lower than 4 nM, lower than 3 nM, lower than 2 nM, lower than 1 nM, lower than 0.5 nM, lower than 0.3 nM, lower than 0.2 nM, or lower than 0.1 nM; for inhibiting MMP9 catalytic activity on gelatin.

The ability of an antibody to block or neutralize the activity of its target protein can also be evaluated by its efficacy of inhibition as defined herewith, which is itself reflected, for instance, by the percentage (%) of inhibition value.

In some embodiments, the antibodies, and fragments thereof, according to the invention have an efficacy equal to or superior than 50%, in particular equal to or superior than 60%, in particular equal to or superior than 70%, in particular equal to or superior than 80%, in particular equal to or superior than 90%, in particular equal to or superior than 95%, in particular equal to 100%, for inhibiting processing of the preproenzyme and/or proenzyme and/or by inhibiting the proteolytic activity of the activated MMP9, as determined for instance in an assay measuring the catalytic activity of MMP9 towards gelatin as described in the example section.

In a particular embodiment, the antibodies, and fragments thereof, according to the invention have an efficacy equal to or superior than 50%, in particular equal to or superior than 60%, in particular equal to or superior than 70%, in particular equal to or superior than 80%, in particular equal to or superior than 90%, in particular equal to or superior than 95%, in particular equal to 100%, for inhibiting the proteolytic activity of the activated MMP9, as determined for instance in an assay measuring the catalytic activity of MMP9 towards gelatin as described in the example section.

It is understood that any variant of an antibody according to the invention, or fragment thereof, that is described herewith is able to bind MMP9 and optionally neutralize MMP9 activity. In a particular embodiment, such variant can show the same or even higher binding affinity for MMP9 and/or the same or even higher potency and/or the same or greater species-selectivity and/or the same or greater selectivity for MMP9, and/or the same or greater neutralizing efficacy, in comparison to the parental antibody or fragment from which said variant derives.

The antibodies according to the invention can be monoclonal antibodies, polyclonal antibodies, human antibodies, humanized antibodies, chimeric antibodies, and further engineered antibodies as long as the characteristic properties of the invention are retained, in particular the ability of binding to the target antigen, more specifically to the same epitope of MMP9 as the one recognized by the antibodies of the invention, and optionally the ability of neutralizing MMP9 activity.

In a particular embodiment of the invention, the antibodies specific for MMP9 according to the invention, or fragments thereof which specifically bind to MMP9, are monoclonal antibodies.

In a further particular embodiment of the invention, the antibodies specific for MMP9 according to the invention, or fragments thereof, which specifically bind to MMP9, are human antibodies.

The antibodies specific for MMP9 according to the invention, or fragments thereof which specifically bind to MMP9, can be characterized by their portion interacting with the target's protein, in particular by their variable region, which typically comprises a heavy chain variable region and a light chain variable region.

Characteristics of the MMP9 Binding Proteins in Relation to their Heavy Chain Variable Region In one embodiment, the invention relates to isolated antibodies specific for MMP9 or antigen-binding fragments thereof comprising a heavy chain variable region comprising:
(i) a heavy chain CDR1 of SEQ ID NO: 2 or a variant thereof wherein 1, 2, or 3 amino acids of said heavy chain CDR1 is substituted by a different amino acid;
(ii) a heavy chain CDR2 of SEQ ID NO: 3 or a variant thereof wherein 1, 2, or 3 amino acids of said heavy chain CDR2 is substituted by a different amino acid;
(iii) a heavy chain CDR3 of SEQ ID NO: 4 or a variant thereof wherein 1, 2, or 3 amino acids of said heavy chain CDR3 is substituted by a different amino acid.

In a particular embodiment of the invention, at least one amino acid at positions 53 and 61 of said heavy chain CDR2, and/or one amino acid at position 100J of said heavy chain CDR3, is substituted by a different amino acid, in particular with at least one of the following substitutions: N53Q or N53R, D61E, M100JI.

In a particular embodiment of the invention, at least one amino acid at positions 53, 61 and 62 of said heavy chain CDR2, and/or one amino acid at position 100 L of said heavy chain CDR3, is substituted by a different amino acid, in particular with at least one of the following substitutions: N53Q, N53R, N53K, N53H, D61E, S62T, M100LI or M100LL.

In another particular embodiment of the invention, said heavy chain CDR2 variant has an amino acid sequence selected among: SEQ ID NO: 5, SEQ ID NO: 6, SEQ ID NO: 7, SEQ ID NO: 8, and SEQ ID NO: 9.

In another particular embodiment of the invention, said heavy chain CDR2 variant has an amino acid sequence selected among: SEQ ID NO: 49, SEQ ID NO: 50, and SEQ ID NO: 51.

In another particular embodiment of the invention, said heavy chain CDR3 variant has an amino acid sequence SEQ ID NO: 10.

In another particular embodiment of the invention, said heavy chain CDR3 variant has an amino acid sequence SEQ ID NO: 52.

In another particular embodiment of the invention, the antibodies specific for MMP9, or antigen-binding fragments thereof, comprise a heavy chain variable region of SEQ ID NO: 11 or SEQ ID NO: 12, or a variant thereof wherein 1, 2, 3, 4, 5, 6, 7, 8, 9, 10, 15, 20 and up to 25 amino acids of SEQ ID NO: 11 or SEQ ID NO: 12 is substituted by a different amino acid, or a variant thereof having at least 80%, at least 85%, at least 90%, at least 95%, at least 98%, at least 99% identity with SEQ ID NO: 11 or SEQ ID NO: 12, respectively.

In another particular embodiment of the invention, the antibodies specific for MMP9, or antigen-binding fragments thereof, comprise a heavy chain variable region of SEQ ID NO: 11 or a variant thereof wherein 1, 2, 3, 4, 5, 6, 7, 8, 9, 10, 15, 20 and up to 25 amino acids are substituted by a different amino acid, wherein said amino acids are comprised within framework regions of said heavy chain variable region.

In another particular embodiment of the invention, the antibodies specific for MMP9, or antigen-binding fragments thereof, comprise a heavy chain variable region of SEQ ID NO: 11 or a variant thereof wherein 1, 2, 3, 4 amino acids are substituted by a different amino acid, wherein said amino acids are comprised within framework regions of said heavy chain variable region.

In another particular embodiment of the invention, the antibodies specific for MMP9, or antigen-binding fragments thereof, comprise a heavy chain variable region of SEQ ID NO: 11 or a variant thereof wherein 2 amino acids are substituted by different amino acids, wherein said amino acids are comprised within framework regions of said heavy chain variable region.

In another particular embodiment of the invention, the antibodies specific for MMP9, or antigen-binding fragments thereof, comprise a heavy chain variable region of SEQ ID NO: 11 wherein 2 amino acids are substituted by different amino acids, wherein said heavy chain variable region is of SEQ ID NO: 12.

In another particular embodiment of the invention, the antibodies specific for MMP9, or antigen-binding fragments thereof, comprise a heavy chain variable region of SEQ ID NO: 11 or a variant thereof wherein 3 amino acids are substituted by different amino acids, wherein said amino acids are comprised within framework regions of said heavy chain variable region.

In another particular embodiment of the invention, the antibodies specific for MMP9, or antigen-binding fragments thereof, comprise a heavy chain variable region of SEQ ID NO: 11 wherein 3 amino acids are substituted by different amino acids, wherein said heavy chain variable region is of SEQ ID NO: 48.

In a further embodiment, the antibodies specific for MMP9, or antigen-binding fragments thereof, comprise a variant of SEQ ID NO: 11 or SEQ ID NO: 12, wherein 1, 2, or 3 amino acids of at least one of the heavy chain CDR1, CDR2, and/or CDR3, and/or 1, 2, 3, 4, 5, 6, 7, 8, 9, or 10 amino acids of the heavy chain variable framework region is substituted by a different amino acid.

In a further embodiment, the antibodies specific for MMP9, or antigen-binding fragments thereof, comprise a variant of SEQ ID NO: 11 or SEQ ID NO: 12, wherein 1, 2, or 3 amino acids of at least one of the heavy chain CDR1, CDR2, and/or CDR3, and/or 11, 12, 13, 14 or 15 amino acids of the heavy chain variable framework region is substituted by a different amino acid.

In particular, the antibodies specific for MMP9 or fragment thereof according to the invention comprise a variant of SEQ ID NO: 11, wherein at least one amino acid at positions 53 and 61 of the heavy chain CDR2, wherein at least one amino acid at position 100J of the heavy chain CDR3, and at positions 84 and 89 of the heavy chain variable framework region is substituted by a different amino acid, in particular with at least one of the following substitutions: N53Q, N53R, D61E, M100JI, D84A and V89L.

In particular, the antibodies specific for MMP9 or fragment thereof according to the invention comprise a variant of SEQ ID NO: 11, wherein at least one amino acid at positions 53, 61 and 62 of the heavy chain CDR2, wherein at least one amino acid at position 100 L of the heavy chain CDR3, and at positions 84 and 89 of the heavy chain variable framework region is substituted by a different amino acid, in particular with at least one of the following substitutions: N53Q, N53R, N53K, N53H, D61E, S62T, D84A, V89L, M100LL and M100LI.

More particularly, the antibodies specific for MMP9 or fragment thereof according to the invention comprise a variant of SEQ ID NO: 11, wherein amino acids at positions 84 and 89 of the heavy chain variable framework region and at least one amino acid at positions 53 and 61 of the heavy chain CDR2, and at position 100J of the heavy chain CDR3 is substituted by a different amino acid, in particular with D84A and V89L substitutions and at least one of the following substitutions: N53Q, N53R, D61E, and M100JI.

In particular, the antibodies specific for MMP9 or fragment thereof according to the invention comprise a variant of SEQ ID NO: 11, wherein at least one amino acid at positions 53, 61 and 62 of the heavy chain CDR2, wherein at least one amino acid at position 100 L of the heavy chain CDR3, and at positions 30, 84 and 89 of the heavy chain variable framework region is substituted by a different amino acid, in particular with at least one of the following substitutions: N53Q, N53R, N53K, N53H, D61E, S62T, M100LL, M100LI, N30D, D84A and V89L.

Specific examples of the heavy chain variable region comprised in the antibodies or fragments thereof according to the invention include:
  (i) the amino acid sequence SEQ ID NO: 11,
  (ii) the amino acid sequence SEQ ID NO: 12
  (iii) the amino acid sequence SEQ ID NO: 13
  (iv) the amino acid sequence SEQ ID NO: 14
  (v) the amino acid sequence SEQ ID NO: 15
  (vi) the amino acid sequence SEQ ID NO: 16.

Alternative specific examples of the heavy chain variable region comprised in the antibodies or fragments thereof according to the invention include:
  (i) the amino acid sequence SEQ ID NO: 17
  (ii) the amino acid sequence SEQ ID NO: 18
  (iii) the amino acid sequence SEQ ID NO: 19
  (iv) the amino acid sequence SEQ ID NO: 20.

Alternative specific examples of the heavy chain variable region comprised in the antibodies or fragments thereof according to the invention include:
  (i) the amino acid sequence SEQ ID NO: 48
  (ii) the amino acid sequence SEQ ID NO: 53
  (iii) the amino acid sequence SEQ ID NO: 54
  (iv) the amino acid sequence SEQ ID NO: 55
  (v) the amino acid sequence SEQ ID NO: 56.

Characteristics of the MMP9 Binding Proteins in Relation to their Light Chain Variable Region In one embodiment, the invention relates to isolated antibodies specific for MMP9 or antigen-binding fragments thereof comprising a heavy chain variable region as described above and further comprising a light chain variable region comprising:
  (i) a light chain CDR1 of SEQ ID NO: 21 or a variant thereof wherein 1, 2, or 3 amino acids of said light chain CDR1 is substituted by a different amino acid;
  (ii) a light chain CDR2 of SEQ ID NO: 22 or a variant thereof wherein 1, 2, or 3 amino acids of said light chain CDR2 is substituted by a different amino acid;
  (iii) a light chain CDR3 of SEQ ID NO: 23 or a variant thereof wherein 1, 2, or 3 amino acids of said light chain CDR3 is substituted by a different amino acid.

In a particular embodiment of the invention, the antibodies specific for MMP9, or antigen-binding fragments thereof, comprise a light chain variable region of SEQ ID NO: 24 or SEQ ID NO: 25, or a variant thereof wherein 1, 2, 3, 4, 5, 6, 7, 8, 9, 10, 15, up to 22 or up to 25 amino acids of SEQ ID NO: 24 or SEQ ID NO: 25 is substituted by a different amino acid, or a variant thereof having at least 80%, at least 85%, at least 90%, at least 95%, at least 98%, at least 99% identity with SEQ ID NO: 24 or SEQ ID NO: 25, respectively.

In a particular embodiment of the invention, the antibodies specific for MMP9, or antigen-binding fragments thereof, comprise a light chain variable region of SEQ ID NO: 67, or a variant thereof wherein 1, 2, 3, 4, 5, 6, 7, 8, 9, 10, 15, up to 22 or up to 25 amino acids of SEQ ID NO: 67 is substituted by a different amino acid, or a variant thereof having at least 80%, at least 85%, at least 90%, at least 95%, at least 98%, at least 99% identity with SEQ ID NO: 67.

In a further embodiment, the antibodies specific for MMP9, or antigen-binding fragments thereof, comprise a variant of SEQ ID NO: 24 or SEQ ID NO: 25, wherein 1, 2, or 3 amino acids of at least one of the light chain CDR1, CDR2, and/or CDR3, and/or 1, 2, 3, 4, 5, 6, 7, 8, 9, or 10 amino acids of the light chain variable framework region is substituted by a different amino acid.

In a further embodiment, the antibodies specific for MMP9, or antigen-binding fragments thereof, comprise a variant of SEQ ID NO: 67, wherein 1, 2, or 3 amino acids of at least one of the light chain CDR1, CDR2, and/or CDR3, and/or 1, 2, 3, 4, 5, 6, 7, 8, 9, or 10 amino acids of the light chain variable framework region is substituted by a different amino acid.

In another particular embodiment of the invention, the antibodies specific for MMP9, or antigen-binding fragments thereof, comprise a light chain variable region of SEQ ID NO: 67 or a variant thereof wherein 1, 2, 3, 4, 5, 6, 7, 8, 9, 10, 15, 20 and up to 25 amino acids are substituted by a different amino acid, wherein said amino acids are comprised within framework regions of said light chain variable region.

In another particular embodiment of the invention, the antibodies specific for MMP9, or antigen-binding fragments thereof, comprise a light chain variable region of SEQ ID NO: 67 or a variant thereof wherein 1, 2, 3, 4 amino acids are substituted by a different amino acid, wherein said amino acids are comprised within framework regions of said light chain variable region.

In another particular embodiment of the invention, the antibodies specific for MMP9, or antigen-binding fragments thereof, comprise a light chain variable region of SEQ ID NO: 67 or a variant thereof wherein 1 amino acid is substituted by different amino acid, wherein said amino acid is comprised within framework region of said light chain variable region.

In another particular embodiment of the invention, the antibodies specific for MMP9, or antigen-binding fragments thereof, comprise a light chain variable region of SEQ ID NO: 67 wherein 1 amino acid is substituted by different amino acid, wherein said light chain variable region is of SEQ ID NO: 68.

In another particular embodiment of the invention, the antibodies specific for MMP9, or antigen-binding fragments thereof, comprise a light chain variable region of SEQ ID NO: 67 or a variant thereof wherein 3 amino acids are substituted by different amino acids, wherein said amino acids are comprised within framework region of said light chain variable region.

In another particular embodiment of the invention, the antibodies specific for MMP9, or antigen-binding fragments thereof, comprise a light chain variable region of SEQ ID NO: 67 wherein 3 amino acids are substituted by different amino acids, wherein said light chain variable region is of SEQ ID NO: 57.

In a further embodiment, the antibodies specific for MMP9, or antigen-binding fragments thereof, comprise a variant of SEQ ID NO: 24 or SEQ ID NO: 25, wherein 1, 2, or 3 amino acids of at least one of the light chain CDR1, CDR2, and/or CDR3, and/or 11, 12, 13, 14 or 15 amino acids of the light chain variable framework region is substituted by a different amino acid.

In particular, the antibodies specific for MMP9 or fragment thereof according to the invention comprise a variant of SEQ ID NO: 24, wherein at least amino acid at position 104 of the light chain variable framework region is substituted by a different amino acid, in particular with at least the following substitution: V104L.

One specific example of the variable region comprised in the antibodies or fragments thereof according to the invention includes the amino acid sequence SEQ ID NO: 25.

In particular, the antibodies specific for MMP9 or fragment thereof according to the invention comprise a variant of SEQ ID NO: 67, wherein at amino acid at positions 104, of the light chain framework region is substituted by a different amino acid, in particular with at least the following substitution V104L.

One specific example of the variable region comprised in the antibodies or fragments thereof according to the invention includes the amino acid sequence SEQ ID NO: 68.

In particular, the antibodies specific for MMP9 or fragment thereof according to the invention comprise a variant of SEQ ID NO: 67, wherein at least three amino acid at positions 46, 71 and 104 of the light chain framework region is substituted by a different amino acid, in particular with at least the following substitution: V46L, V71A and V104L.

One specific example of the variable region comprised in the antibodies or fragments thereof according to the invention includes the amino acid sequence SEQ ID NO: 57.

In an alternative embodiment, the invention relates to isolated antibodies specific for MMP9 or antigen-binding fragments thereof comprising a heavy chain variable region as described above and further comprising a light chain variable region comprising:
  (i) a light chain CDR1 of SEQ ID NO: 26 or a variant thereof wherein 1, 2, or 3 amino acids of said light chain CDR1 is substituted by a different amino acid;
  (ii) a light chain CDR2 of SEQ ID NO: 27 or a variant thereof wherein 1, 2, or 3 amino acids of said light chain CDR2 is substituted by a different amino acid;
  (iii) a light chain CDR3 of SEQ ID NO: 28 or a variant thereof wherein 1, 2, or 3 amino acids of said light chain CDR3 is substituted by a different amino acid.

In a particular embodiment of the invention, the antibodies specific for MMP9, or antigen-binding fragments thereof, comprise a light chain variable region of SEQ ID NO: 29 or SEQ ID NO: 30, or a variant thereof wherein 1, 2, 3, 4, 5, 6, 7, 8, 9, 10, 15, up to 22 or up to 25 amino acids of SEQ ID NO: 29 or SEQ ID NO: 30 is substituted by a different amino acid, or a variant thereof having at least 80%, at least 85%, at least 90%, at least 95%, at least 98%, at least 99% identity with SEQ ID NO: 29 or SEQ ID NO: 30, respectively.

In a particular embodiment of the invention, the antibodies specific for MMP9, or antigen-binding fragments thereof, comprise a light chain variable region of SEQ ID NO: 69, or a variant thereof wherein 1, 2, 3, 4, 5, 6, 7, 8, 9, 10, 15, up to 22 or up to 25 amino acids of SEQ ID NO: 69 is substituted by a different amino acid, or a variant thereof having at least 80%, at least 85%, at least 90%, at least 95%, at least 98%, at least 99% identity with SEQ ID NO: 69.

In a further embodiment, the antibodies specific for MMP9, or antigen-binding fragments thereof, comprise a variant of SEQ ID NO: 29 or SEQ ID NO: 30, wherein 1, 2, or 3 amino acids of at least one of the light chain CDR1, CDR2, and/or CDR3, and/or 1, 2, 3, 4, 5, 6, 7, 8, 9, or 10 amino acids of the light chain variable framework region is substituted by a different amino acid.

In a further embodiment, the antibodies specific for MMP9, or antigen-binding fragments thereof, comprise a variant of SEQ ID NO: 29 or SEQ ID NO: 30, wherein 1, 2, or 3 amino acids of at least one of the light chain CDR1, CDR2, and/or CDR3, and/or 11, 12, 13, 14, or 15 amino acids of the light chain variable framework region is substituted by a different amino acid.

In another particular embodiment of the invention, the antibodies specific for MMP9, or antigen-binding fragments thereof, comprise a light chain variable region of SEQ ID NO: 69 or a variant thereof wherein 1, 2, 3, 4, 5, 6, 7, 8, 9, 10, 15, 20 and up to 25 amino acids are substituted by a different amino acid, wherein said amino acids are comprised within framework regions of said light chain variable region.

In another particular embodiment of the invention, the antibodies specific for MMP9, or antigen-binding fragments thereof, comprise a light chain variable region of SEQ ID NO: 69 or a variant thereof wherein 3, 4, 5, 6, 7, 8 amino acids are substituted by a different amino acid, wherein said amino acids are comprised within framework regions of said light chain variable region.

In another particular embodiment of the invention, the antibodies specific for MMP9, or antigen-binding fragments thereof, comprise a light chain variable region of SEQ ID NO: 69 or a variant thereof wherein 4 amino acids are substituted by different amino acids, wherein said amino acids are comprised within framework region of said light chain variable region.

In another particular embodiment of the invention, the antibodies specific for MMP9, or antigen-binding fragments thereof, comprise a light chain variable region of SEQ ID NO: 69 wherein 4 amino acids are substituted by different amino acids, wherein said light chain variable region is of SEQ ID NO: 58.

In another particular embodiment of the invention, the antibodies specific for MMP9, or antigen-binding fragments thereof, comprise a light chain variable region of SEQ ID NO: 69 or a variant thereof wherein 5 amino acids are substituted by different amino acids, wherein said amino acids are comprised within framework region of said light chain variable region.

In another particular embodiment of the invention, the antibodies specific for MMP9, or antigen-binding fragments thereof, comprise a light chain variable region of SEQ ID NO: 69 wherein 5 amino acids are substituted by different amino acids, wherein said light chain variable region is selected from SEQ ID NO: 59, SEQ ID NO: 60 and SEQ ID NO: 61.

In another particular embodiment of the invention, the antibodies specific for MMP9, or antigen-binding fragments thereof, comprise a light chain variable region of SEQ ID NO: 29 or a variant thereof wherein 6 amino acids are substituted by different amino acids, wherein said amino acids are comprised within framework region of said light chain variable region.

In another particular embodiment of the invention, the antibodies specific for MMP9, or antigen-binding fragments thereof, comprise a light chain variable region of SEQ ID NO: 29 wherein 6 amino acids are substituted by different amino acids, wherein said light chain variable region is of SEQ ID NO: 30.

In another particular embodiment of the invention, the antibodies specific for MMP9, or antigen-binding fragments thereof, comprise a light chain variable region of SEQ ID NO: 69 or a variant thereof wherein 6 amino acids are substituted by different amino acids, wherein said amino acids are comprised within framework region of said light chain variable region.30

In another particular embodiment of the invention, the antibodies specific for MMP9, or antigen-binding fragments thereof, comprise a light chain variable region of SEQ ID NO: 69 wherein 6 amino acids are substituted by different amino acids, wherein said light chain variable region is selected from SEQ ID NO: 62 and SEQ ID NO: 70.

In another particular embodiment of the invention, the antibodies specific for MMP9, or antigen-binding fragments thereof, comprise a light chain variable region of SEQ ID NO: 69 or a variant thereof wherein 7 amino acids are substituted by different amino acids, wherein said amino acids are comprised within framework region of said light chain variable region.

In another particular embodiment of the invention, the antibodies specific for MMP9, or antigen-binding fragments thereof, comprise a light chain variable region of SEQ ID NO: 69 wherein 7 amino acids are substituted by different amino acids, wherein said light chain variable region is of SEQ ID NO: 63.

In particular, the antibodies specific for MMP9 or fragments thereof according to the invention comprise a variant of SEQ ID NO: 29, wherein at least one amino acid at positions 8, 19, 47, 60, 79, and 81 of the light chain variable framework region is substituted by a different amino acid, in particular with at least one of the following substitutions: R8A, V19I, L47M, T60N, L79Q, and A81E.

One specific example of the variable region comprised in the antibodies or fragments thereof according to the invention includes the amino acid sequence SEQ ID NO: 30.

In particular, the antibodies specific for MMP9 or fragments thereof according to the invention comprise a variant of SEQ ID NO: 69, wherein at least one amino acid at positions 8, 19, 47, 60, 79, 81, 86 of the light chain variable framework region is substituted by a different amino acid, in particular with at least one of the following substitutions: R8A, V19I, L47M, T60N, L79Q, A81E and F86Y.

One specific example of the variable region comprised in the antibodies or fragments thereof according to the invention includes the amino acid sequence SEQ ID NO: 70.

Specific examples of the light chain variable region comprised in the antibodies or fragments thereof according to the invention include:
 (i) the amino acid sequence SEQ ID NO: 24,
 (ii) the amino acid sequence SEQ ID NO: 25,
 (iii) the amino acid sequence SEQ ID NO: 29,
 (iv) the amino acid sequence SEQ ID NO: 30,
 (v) the amino acid sequence SEQ ID NO: 57,
 (vi) the amino acid sequence SEQ ID NO: 58,
 (vii) the amino acid sequence SEQ ID NO: 59,
 (viii) the amino acid sequence SEQ ID NO: 60,
 (ix) the amino acid sequence SEQ ID NO: 61,
 (x) the amino acid sequence SEQ ID NO: 62,
 (xi) the amino acid sequence SEQ ID NO: 63,
 (xii) the amino acid sequence SEQ ID NO: 67,
 (xiii) the amino acid sequence SEQ ID NO: 68,
 (xiv) the amino acid sequence SEQ ID NO: 69,
 (xv) the amino acid sequence SEQ ID NO: 70.

Characteristics of the MMP9 Binding Proteins in Relation to their Constant Region A portion corresponding to a constant region of an antibody is optionally comprised in the isolated antibodies specific for MMP9, or antigen-binding fragments thereof, according to the invention.

Depending on the proposed function of the antibodies and, in particular the effector functions which may be required, a constant region of an antibody may or may not be present within the antibodies according to the invention.

Typically, when present within the antibodies or antigen-binding fragments thereof according to the invention, the heavy chain constant region or portion thereof can be from any antibody isotype. For instance, the heavy chain constant region or portion thereof can be that of an antibody selected from IgG (e.g. IgG1, IgG2, IgG3, IgG4), IgA (e.g. IgA1, IgA2), IgD, IgE, IgM (e.g. IgM1, IgM2). It can be, in particular, the constant region or portion thereof of an IgG, more particularly IgG4.

In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking MMP9 activity.

It will be appreciated that sequence variants of these constant region domains may also be used. For instance, the heavy chain constant region or portion thereof can be that of an engineered variant of IgG4 such as an IgG4 variant comprising S228P, R409K and a deletion of the terminal lysine, corresponding to amino acid sequence SEQ ID NO: 40.

When present within the antibodies or antigen-binding fragments thereof according to the invention, the light chain constant region or portion thereof can be from any light chain's constant region. For instance, the light chain constant region or portion thereof can be from the kappa or lambda light chain.

In a particular aspect of the invention, the antibodies specific for MMP9, or antigen-binding fragments thereof, comprise (i) at least one heavy chain comprising a variable region as described herewith and a constant region or portion thereof from an IgG antibody, and (ii) at least one light chain comprising a variable region as described herewith and a constant region or portion thereof from a lambda (in particular lambda 2) light chain.

In a particular embodiment, the constant region or portion thereof of the heavy chain and/or of the light chain, which is comprised in the antibodies according to the invention, has an amino acid sequence which has been modified compared to its original amino acid sequence, according to methods known in the art, to increase the chemical stability of the antibodies, decrease their aggregation, increase their production in particular in antibody-producing cells (e.g. HEK293 cells, CHO cells), and/or eliminate their ability to exchange half-molecules which would effectively result in monovalent antibodies.

Examples of amino acids within the amino acid sequence of the constant region of an antibody which affect the antibody's stability include S228P amino acid mutation (EU numbering) in the human IgG4 heavy chain that stabilizes the hinge domain of the antibody (Angal et al, 1993, *Molec. Immunol.* 30: 105-108) and avoids Fc-Fc interactions (Rispens et al., 2013, *Mol. Immunol.* 53: 35-42), a Lys (K) rather than an Arg (R) at allotypic position 409 (EU numbering) that increases the CH3-CH3 interaction strength in IgG4 (Allberse et al, 2002, *Immunology* 105: 9-19), those examples are incorporated herewith by reference. In addition, in order to simplify the monitoring of monoclonal antibody charge heterogeneity, the C-terminal lysine of the human IgG4 heavy chain can be removed.

In a further embodiment, the antibodies specific for MMP9, or antigen-binding fragments thereof, according to the invention comprise at least one heavy chain comprising a variable region as described herewith and a constant region or portion thereof from an IgG4 antibody, wherein the amino acid sequence of the IgG4 constant region comprises the following amino acids modifications: S228P (EU numbering), R409K (EU numbering), deletion of the terminal Lys (K), wherein said modified constant region is represented by SEQ ID NO: 40.

In a further embodiment, the antibodies specific for MMP9, or antigen-binding fragments thereof, according to the invention comprise at least one light chain comprising a variable region as described herewith and a constant region or portion thereof from an IgG4 antibody wherein said constant region is represented by SEQ ID NO: 66.

It derives from the above that the present invention provides, in particular, isolated antibodies specific for MMP9 or antigen-binding fragment thereof comprising:
(1) a heavy chain variable region comprising:
  (i) a heavy chain CDR1 of SEQ ID NO: 2 or a variant thereof wherein 1, 2, or 3 amino acids of said heavy chain CDR1 is substituted by a different amino acid;
  (ii) a heavy chain CDR2 of SEQ ID NO: 3 or a variant thereof wherein 1, 2, or 3 amino acids of said heavy chain CDR2 is substituted by a different amino acid;
  (iii) a heavy chain CDR3 of SEQ ID NO: 4 or a variant thereof wherein 1, 2, or 3 amino acids of said heavy chain CDR3 is substituted by a different amino acid; and
(2) a light chain variable region comprising:
  (i) a light chain CDR1 of SEQ ID NO: 21 or a variant thereof wherein 1, 2, or 3 amino acids of said light chain CDR1 is substituted by a different amino acid;
  (ii) a light chain CDR2 of SEQ ID NO: 22 or a variant thereof wherein 1, 2, or 3 amino acids of said light chain CDR2 is substituted by a different amino acid;
  (iii) a light chain CDR3 of SEQ ID NO: 23 or a variant thereof wherein 1, 2, or 3 amino acids of said light chain CDR3 is substituted by a different amino acid.

In another embodiment, the present invention provides isolated antibodies specific for MMP9 or antigen-binding fragment thereof comprising:
(1) a heavy chain variable region comprising:
  (i) a heavy chain CDR1 of SEQ ID NO: 2 or a variant thereof wherein 1, 2, or 3 amino acids of said heavy chain CDR1 is substituted by a different amino acid;
  (ii) a heavy chain CDR2 of SEQ ID NO: 3 or a variant thereof wherein 1, 2, or 3 amino acids of said heavy chain CDR2 is substituted by a different amino acid;
  (iii) a heavy chain CDR3 of SEQ ID NO: 4 or a variant thereof wherein 1, 2, or 3 amino acids of said heavy chain CDR3 is substituted by a different amino acid; and
(2) a light chain variable region comprising:
  (i) a light chain CDR1 of SEQ ID NO: 26 or a variant thereof wherein 1, 2, or 3 amino acids of said light chain CDR1 is substituted by a different amino acid;
  (ii) a light chain CDR2 of SEQ ID NO: 27 or a variant thereof wherein 1, 2, or 3 amino acids of said light chain CDR2 is substituted by a different amino acid;
  (iii) a light chain CDR3 of SEQ ID NO: 28 or a variant thereof wherein 1, 2, or 3 amino acids of said light chain CDR3 is substituted by a different amino acid.

In another particular embodiment of the invention, said heavy chain CDR2 variant has an amino acid sequence selected among: SEQ ID NO: 5, SEQ ID NO: 6, SEQ ID NO: 7, SEQ ID NO: 8, and SEQ ID NO: 9.

In another particular embodiment of the invention, said heavy chain CDR2 variant has an amino acid sequence selected among: SEQ ID NO: 49, SEQ ID NO: 50, and SEQ ID NO: 51.

In another particular embodiment of the invention, said heavy chain CDR3 variant has an amino acid sequence SEQ ID NO: 10.

In another particular embodiment of the invention, said heavy chain CDR3 variant has an amino acid sequence SEQ ID NO: 52.

The antibodies of the invention have at least one antigen binding site, e.g. one or two antigen binding sites. In certain embodiments, for instance for CDR-comprising peptides, a variable domain may contain only CDRs linked via short linker peptides instead of complete framework regions.

In some embodiments, the isolated antibodies and antigen-binding fragments thereof according to the invention are glycosylated. Typically, monosaccharides such as N-acetylglucosamine, mannose, glucose, galactose, fucose, sialic acid, etc, are assembled to oligosaccharides at individual glycosylation sites on the antibody.

As will be understood by the skilled person, one aspect of the present invention relates to isolated antibodies specific for MMP9 or antigen-binding fragments thereof, which are characterized by some of the herewith described features without necessarily comprising all of said features.

For instance, in one aspect, are provided isolated antibodies specific for MMP9 or antigen-binding fragments thereof which are characterized by any of the herewith-described features regarding the sequences of their variable regions and/or constant regions.

In a particular embodiment of said aspect, said antibodies or fragments thereof are further characterized by their binding to MMP9 by interacting with an epitope on MMP9 as described herewith, in particular an epitope comprising at least one amino acid within a region consisting of SEQ ID NO: 41, at least one amino acid within a region consisting of SEQ ID NO: 42, and at least one amino acid within a region consisting of SEQ ID NO: 43, located in the catalytic domain of human MMP9.

In an alternative aspect, are provided isolated antibodies specific for MMP9 or antigen-binding fragments thereof which are characterized by their binding to MMP9 by interacting with an epitope on MMP9 as described herewith, in particular an epitope comprising at least one amino acid within a region consisting of SEQ ID NO: 41, at least one amino acid within a region consisting of SEQ ID NO: 42, and at least one amino acid within a region consisting of SEQ ID NO: 43, located in the catalytic domain of human MMP9.

In a particular embodiment of said alternative aspect, said antibodies or fragments thereof are further characterized by any of the herewith-described features regarding the sequences of their variable regions and/or constant regions.

Examples of Antibodies Specific for MMP9 or Antigen-Binding Fragment Thereof

Examples of antibodies and fragments thereof according to the invention include those comprising the variable domains indicated in Table 2 (see also FIGS. 3, 4, 5).

TABLE 2

| Name | Sequence of Heavy chain variable region | Sequence of Light chain variable region |
|---|---|---|
| F20-VH/B03-VL | SEQ ID NO: 11 | SEQ ID NO: 24 |
| F20-VH-GL1/B03-VL | SEQ ID NO: 12 | SEQ ID NO: 24 |
| F20-VH-GL1-V1/B03-VL | SEQ ID NO: 13 | SEQ ID NO: 24 |
| F20-VH-GL1-V4/B03-VL | SEQ ID NO: 14 | SEQ ID NO: 24 |
| F20-VH-GL1-V9/B03-VL | SEQ ID NO: 15 | SEQ ID NO: 24 |
| F20-VH-GL1-V14/B03-VL | SEQ ID NO: 16 | SEQ ID NO: 24 |
| F20-VH-GL1-V1-V9/B03-VL | SEQ ID NO: 17 | SEQ ID NO: 24 |
| F20-VH-GL1-V1-V9-V14/B03-VL | SEQ ID NO: 18 | SEQ ID NO: 24 |
| F20-VH-GL1-V4-V9/B03-VL | SEQ ID NO: 19 | SEQ ID NO: 24 |
| F20-VH-GL1-V4-V9-V14/B03-VL | SEQ ID NO: 20 | SEQ ID NO: 24 |
| F20-VH/B03-VL-GL1 | SEQ ID NO: 11 | SEQ ID NO: 25 |
| F20-VH-GL1/B03-VL-GL1 | SEQ ID NO: 12 | SEQ ID NO: 25 |
| F20-VH-GL1-V1/B03-VL-GL1 | SEQ ID NO: 13 | SEQ ID NO: 25 |
| F20-VH-GL1-V4/B03-VL-GL1 | SEQ ID NO: 14 | SEQ ID NO: 25 |
| F20-VH-GL1-V9/B03-VL-GL1 | SEQ ID NO: 15 | SEQ ID NO: 25 |
| F20-VH-GL1-V14/B03-VL-GL1 | SEQ ID NO: 16 | SEQ ID NO: 25 |
| F20-VH-GL1-V1-V9/B03-VL-GL1 | SEQ ID NO: 17 | SEQ ID NO: 25 |
| F20-VH-GL1-V1-V9-V14/B03-VL-GL1 | SEQ ID NO: 18 | SEQ ID NO: 25 |
| F20-VH-GL1-V4-V9/B03-VL-GL1 | SEQ ID NO: 19 | SEQ ID NO: 25 |
| F20-VH-GL1-V4-V9-V14/B03-VL-GL1 | SEQ ID NO: 20 | SEQ ID NO: 25 |
| F20-VH/B08-VL | SEQ ID NO: 11 | SEQ ID NO: 29 |
| F20-VH-GL1/B08-VL | SEQ ID NO: 12 | SEQ ID NO: 29 |
| F20-VH-GL1-V1/B08-VL | SEQ ID NO: 13 | SEQ ID NO: 29 |
| F20-VH-GL1-V4/B08-VL | SEQ ID NO: 14 | SEQ ID NO: 29 |
| F20-VH-GL1-V9/B08-VL | SEQ ID NO: 15 | SEQ ID NO: 29 |
| F20-VH-GL1-V14/B08-VL | SEQ ID NO: 16 | SEQ ID NO: 29 |
| F20-VH-GL1-V1-V9/B08-VL | SEQ ID NO: 17 | SEQ ID NO: 29 |
| F20-VH-GL1-V1-V9-V14/B08-VL | SEQ ID NO: 18 | SEQ ID NO: 29 |
| F20-VH-GL1-V4-V9/B08-VL | SEQ ID NO: 19 | SEQ ID NO: 29 |
| F20-VH-GL1-V4-V9-V14/B08-VL | SEQ ID NO: 20 | SEQ ID NO: 29 |
| F20-VH/B08-VL-GL6 | SEQ ID NO: 11 | SEQ ID NO: 30 |
| F20-VH-GL1/B08-VL-GL6 | SEQ ID NO: 12 | SEQ ID NO: 30 |
| F20-VH-GL1-V1/B08-VL-GL6 | SEQ ID NO: 13 | SEQ ID NO: 30 |
| F20-VH-GL1-V4/B08-VL-GL6 | SEQ ID NO: 14 | SEQ ID NO: 30 |
| F20-VH-GL1-V9/B08-VL-GL6 | SEQ ID NO: 15 | SEQ ID NO: 30 |
| F20-VH-GL1-V14/B08-VL-GL6 | SEQ ID NO: 16 | SEQ ID NO: 30 |
| F20-VH-GL1-V1-V9/B08-VL-GL6 | SEQ ID NO: 17 | SEQ ID NO: 30 |
| F20-VH-GL1-V1-V9-V14/B08-VL-GL6 | SEQ ID NO: 18 | SEQ ID NO: 30 |
| F20-VH-GL1-V4-V9/B08-VL-GL6 | SEQ ID NO: 19 | SEQ ID NO: 30 |
| F20-VH-GL1-V4-V9-V14/B08-VL-GL6 | SEQ ID NO: 20 | SEQ ID NO: 30 |
| F20-VH-GL2/B03-VL | SEQ ID NO: 48 | SEQ ID NO: 24 |
| F20-VH-GL1-V2/B03-VL | SEQ ID NO: 53 | SEQ ID NO: 24 |
| F20-VH-GL1-V3/B03-VL | SEQ ID NO: 54 | SEQ ID NO: 24 |
| F20-VH-GL1-V11/B03-VL | SEQ ID NO: 55 | SEQ ID NO: 24 |
| F20-VH-GL1-V13/B03-VL | SEQ ID NO: 56 | SEQ ID NO: 24 |
| F20-VH-GL2/B03-VL-GL1 | SEQ ID NO: 48 | SEQ ID NO: 25 |
| F20-VH-GL1-V2/B03-VL-GL1 | SEQ ID NO: 53 | SEQ ID NO: 25 |
| F20-VH-GL1-V3/B03-VL-GL1 | SEQ ID NO: 54 | SEQ ID NO: 25 |
| F20-VH-GL1-V11/B03-VL-GL1 | SEQ ID NO: 55 | SEQ ID NO: 25 |
| F20-VH-GL1-V13/B03-VL-GL1 | SEQ ID NO: 56 | SEQ ID NO: 25 |
| F20-VH-GL2/B08-VL | SEQ ID NO: 48 | SEQ ID NO: 29 |
| F20-VH-GL1-V2/B08-VL | SEQ ID NO: 53 | SEQ ID NO: 29 |
| F20-VH-GL1-V3/B08-VL | SEQ ID NO: 54 | SEQ ID NO: 29 |
| F20-VH-GL1-V11/B08-VL | SEQ ID NO: 55 | SEQ ID NO: 29 |
| F20-VH-GL1-V13/B08-VL | SEQ ID NO: 56 | SEQ ID NO: 29 |
| F20-VH-GL2/B08-VL-GL6 | SEQ ID NO: 48 | SEQ ID NO: 30 |
| F20-VH-GL1-V2/B08-VL-GL6 | SEQ ID NO: 53 | SEQ ID NO: 30 |
| F20-VH-GL1-V3/B08-VL-GL6 | SEQ ID NO: 54 | SEQ ID NO: 30 |
| F20-VH-GL1-V11/B08-VL-GL6 | SEQ ID NO: 55 | SEQ ID NO: 30 |
| F20-VH-GL1-V13/B08-VL-GL6 | SEQ ID NO: 56 | SEQ ID NO: 30 |
| F20-VH/B03-VL-GL2 | SEQ ID NO: 11 | SEQ ID NO: 57 |
| F20-VH-GL1/B03-VL-GL2 | SEQ ID NO: 12 | SEQ ID NO: 57 |
| F20-VH-GL1-V1/B03-VL-GL2 | SEQ ID NO: 13 | SEQ ID NO: 57 |
| F20-VH-GL1-V4/B03-VL-GL2 | SEQ ID NO: 14 | SEQ ID NO: 57 |
| F20-VH-GL1-V9/B03-VL-GL2 | SEQ ID NO: 15 | SEQ ID NO: 57 |
| F20-VH-GL1-V14/B03-VL-GL2 | SEQ ID NO: 16 | SEQ ID NO: 57 |
| F20-VH-GL1-V1-V9/B03-VL-GL2 | SEQ ID NO: 17 | SEQ ID NO: 57 |
| F20-VH-GL1-V1-V9-V14/B03-VL-GL2 | SEQ ID NO: 18 | SEQ ID NO: 57 |
| F20-VH-GL1-V4-V9/B03-VL-GL2 | SEQ ID NO: 19 | SEQ ID NO: 57 |
| F20-VH-GL1-V4-V9-V14/B03-VL-GL2 | SEQ ID NO: 20 | SEQ ID NO: 57 |
| F20-VH-GL2/B03-VL-GL2 | SEQ ID NO: 48 | SEQ ID NO: 57 |
| F20-VH-GL1-V2/B03-VL-GL2 | SEQ ID NO: 53 | SEQ ID NO: 57 |
| F20-VH-GL1-V3/B03-VL-GL2 | SEQ ID NO: 54 | SEQ ID NO: 57 |
| F20-VH-GL1-V11/B03-VL-GL2 | SEQ ID NO: 55 | SEQ ID NO: 57 |
| F20-VH-GL1-V13/B03-VL-GL2 | SEQ ID NO: 56 | SEQ ID NO: 57 |
| F20-VH/B08-VL-GL1 | SEQ ID NO: 11 | SEQ ID NO: 58 |

TABLE 2-continued

| Name | Sequence of Heavy chain variable region | Sequence of Light chain variable region |
|---|---|---|
| F20-VH-GL1/B08-VL-GL1 | SEQ ID NO: 12 | SEQ ID NO: 58 |
| F20-VH-GL1-V1/B08-VL-GL1 | SEQ ID NO: 13 | SEQ ID NO: 58 |
| F20-VH-GL1-V4/B08-VL-GL1 | SEQ ID NO: 14 | SEQ ID NO: 58 |
| F20-VH-GL1-V9/B08-VL-GL1 | SEQ ID NO: 15 | SEQ ID NO: 58 |
| F20-VH-GL1-V14/B08-VL-GL1 | SEQ ID NO: 16 | SEQ ID NO: 58 |
| F20-VH-GL1-V1-V9/B08-VL-GL1 | SEQ ID NO: 17 | SEQ ID NO: 58 |
| F20-VH-GL1-V1-V9-V14/B08-VL-GL1 | SEQ ID NO: 18 | SEQ ID NO: 58 |
| F20-VH-GL1-V4-V9/B08-VL-GL1 | SEQ ID NO: 19 | SEQ ID NO: 58 |
| F20-VH-GL1-V4-V9-V14/B08-VL-GL1 | SEQ ID NO: 20 | SEQ ID NO: 58 |
| F20-VH-GL2/B08-VL-GL1 | SEQ ID NO: 48 | SEQ ID NO: 58 |
| F20-VH-GL1-V2/B08-VL-GL1 | SEQ ID NO: 53 | SEQ ID NO: 58 |
| F20-VH-GL1-V3/B08-VL-GL1 | SEQ ID NO: 54 | SEQ ID NO: 58 |
| F20-VH-GL1-V11/B08-VL-GL1 | SEQ ID NO: 55 | SEQ ID NO: 58 |
| F20-VH-GL1-V13/B08-VL-GL1 | SEQ ID NO: 56 | SEQ ID NO: 58 |
| F20-VH/B08-VL-GL2 | SEQ ID NO: 11 | SEQ ID NO: 59 |
| F20-VH-GL1/B08-VL-GL2 | SEQ ID NO: 12 | SEQ ID NO: 59 |
| F20-VH-GL1-V1/B08-VL-GL2 | SEQ ID NO: 13 | SEQ ID NO: 59 |
| F20-VH-GL1-V4/B08-VL-GL2 | SEQ ID NO: 14 | SEQ ID NO: 59 |
| F20-VH-GL1-V9/B08-VL-GL2 | SEQ ID NO: 15 | SEQ ID NO: 59 |
| F20-VH-GL1-V14/B08-VL-GL2 | SEQ ID NO: 16 | SEQ ID NO: 59 |
| F20-VH-GL1-V1-V9/B08-VL-GL2 | SEQ ID NO: 17 | SEQ ID NO: 59 |
| F20-VH-GL1-V1-V9-V14/B08-VL-GL2 | SEQ ID NO: 18 | SEQ ID NO: 59 |
| F20-VH-GL1-V4-V9/B08-VL-GL2 | SEQ ID NO: 19 | SEQ ID NO: 59 |
| F20-VH-GL1-V4-V9-V14/B08-VL-GL2 | SEQ ID NO: 20 | SEQ ID NO: 59 |
| F20-VH-GL2/B08-VL-GL2 | SEQ ID NO: 48 | SEQ ID NO: 59 |
| F20-VH-GL1-V2/B08-VL-GL2 | SEQ ID NO: 53 | SEQ ID NO: 59 |
| F20-VH-GL1-V3/B08-VL-GL2 | SEQ ID NO: 54 | SEQ ID NO: 59 |
| F20-VH-GL1-V11/B08-VL-GL2 | SEQ ID NO: 55 | SEQ ID NO: 59 |
| F20-VH-GL1-V13/B08-VL-GL2 | SEQ ID NO: 56 | SEQ ID NO: 59 |
| F20-VH/B08-VL-GL3 | SEQ ID NO: 11 | SEQ ID NO: 60 |
| F20-VH-GL1/B08-VL-GL3 | SEQ ID NO: 12 | SEQ ID NO: 60 |
| F20-VH-GL1-V1/B08-VL-GL3 | SEQ ID NO: 13 | SEQ ID NO: 60 |
| F20-VH-GL1-V4/B08-VL-GL3 | SEQ ID NO: 14 | SEQ ID NO: 60 |
| F20-VH-GL1-V9/B08-VL-GL3 | SEQ ID NO: 15 | SEQ ID NO: 60 |
| F20-VH-GL1-V14/B08-VL-GL3 | SEQ ID NO: 16 | SEQ ID NO: 60 |
| F20-VH-GL1-V1-V9/B08-VL-GL3 | SEQ ID NO: 17 | SEQ ID NO: 60 |
| F20-VH-GL1-V1-V9-V14/B08-VL-GL3 | SEQ ID NO: 18 | SEQ ID NO: 60 |
| F20-VH-GL1-V4-V9/B08-VL-GL3 | SEQ ID NO: 19 | SEQ ID NO: 60 |
| F20-VH-GL1-V4-V9-V14/B08-VL-GL3 | SEQ ID NO: 20 | SEQ ID NO: 60 |
| F20-VH-GL2/B08-VL-GL3 | SEQ ID NO: 48 | SEQ ID NO: 60 |
| F20-VH-GL1-V2/B08-VL-GL3 | SEQ ID NO: 53 | SEQ ID NO: 60 |
| F20-VH-GL1-V3/B08-VL-GL3 | SEQ ID NO: 54 | SEQ ID NO: 60 |
| F20-VH-GL1-V11/B08-VL-GL3 | SEQ ID NO: 55 | SEQ ID NO: 60 |
| F20-VH-GL1-V13/B08-VL-GL3 | SEQ ID NO: 56 | SEQ ID NO: 60 |
| F20-VH/B08-VL-GL4 | SEQ ID NO: 11 | SEQ ID NO: 61 |
| F20-VH-GL1/B08-VL-GL4 | SEQ ID NO: 12 | SEQ ID NO: 61 |
| F20-VH-GL1-V1/B08-VL-GL4 | SEQ ID NO: 13 | SEQ ID NO: 61 |
| F20-VH-GL1-V4/B08-VL-GL4 | SEQ ID NO: 14 | SEQ ID NO: 61 |
| F20-VH-GL1-V9/B08-VL-GL4 | SEQ ID NO: 15 | SEQ ID NO: 61 |
| F20-VH-GL1-V14/B08-VL-GL4 | SEQ ID NO: 16 | SEQ ID NO: 61 |
| F20-VH-GL1-V1-V9/B08-VL-GL4 | SEQ ID NO: 17 | SEQ ID NO: 61 |
| F20-VH-GL1-V1-V9-V14/B08-VL-GL4 | SEQ ID NO: 18 | SEQ ID NO: 61 |
| F20-VH-GL1-V4-V9/B08-VL-GL4 | SEQ ID NO: 19 | SEQ ID NO: 61 |
| F20-VH-GL1-V4-V9-V14/B08-VL-GL4 | SEQ ID NO: 20 | SEQ ID NO: 61 |
| F20-VH-GL2/B08-VL-GL4 | SEQ ID NO: 48 | SEQ ID NO: 61 |
| F20-VH-GL1-V2/B08-VL-GL4 | SEQ ID NO: 53 | SEQ ID NO: 61 |
| F20-VH-GL1-V3/B08-VL-GL4 | SEQ ID NO: 54 | SEQ ID NO: 61 |
| F20-VH-GL1-V11/B08-VL-GL4 | SEQ ID NO: 55 | SEQ ID NO: 61 |
| F20-VH-GL1-V13/B08-VL-GL4 | SEQ ID NO: 56 | SEQ ID NO: 61 |
| F20-VH/B08-VL-GL5 | SEQ ID NO: 11 | SEQ ID NO: 62 |
| F20-VH-GL1/B08-VL-GL5 | SEQ ID NO: 12 | SEQ ID NO: 62 |
| F20-VH-GL1-V1/B08-VL-GL5 | SEQ ID NO: 13 | SEQ ID NO: 62 |
| F20-VH-GL1-V4/B08-VL-GL5 | SEQ ID NO: 14 | SEQ ID NO: 62 |
| F20-VH-GL1-V9/B08-VL-GL5 | SEQ ID NO: 15 | SEQ ID NO: 62 |
| F20-VH-GL1-V14/B08-VL-GL5 | SEQ ID NO: 16 | SEQ ID NO: 62 |
| F20-VH-GL1-V1-V9/B08-VL-GL5 | SEQ ID NO: 17 | SEQ ID NO: 62 |
| F20-VH-GL1-V1-V9-V14/B08-VL-GL5 | SEQ ID NO: 18 | SEQ ID NO: 62 |
| F20-VH-GL1-V4-V9/B08-VL-GL5 | SEQ ID NO: 19 | SEQ ID NO: 62 |
| F20-VH-GL1-V4-V9-V14/B08-VL-GL5 | SEQ ID NO: 20 | SEQ ID NO: 62 |
| F20-VH-GL2/B08-VL-GL5 | SEQ ID NO: 48 | SEQ ID NO: 62 |
| F20-VH-GL1-V2/B08-VL-GL5 | SEQ ID NO: 53 | SEQ ID NO: 62 |
| F20-VH-GL1-V3/B08-VL-GL4 | SEQ ID NO: 54 | SEQ ID NO: 62 |
| F20-VH-GL1-V11/B08-VL-GL5 | SEQ ID NO: 55 | SEQ ID NO: 62 |
| F20-VH-GL1-V13/B08-VL-GL5 | SEQ ID NO: 56 | SEQ ID NO: 62 |
| F20-VH/B08-VL-GL7 | SEQ ID NO: 11 | SEQ ID NO: 63 |
| F20-VH-GL1/B08-VL-GL7 | SEQ ID NO: 12 | SEQ ID NO: 63 |

TABLE 2-continued

| Name | Sequence of Heavy chain variable region | Sequence of Light chain variable region |
|---|---|---|
| F20-VH-GL1-V1/B08-VL-GL7 | SEQ ID NO: 13 | SEQ ID NO: 63 |
| F20-VH-GL1-V4/B08-VL-GL7 | SEQ ID NO: 14 | SEQ ID NO: 63 |
| F20-VH-GL1-V9/B08-VL-GL7 | SEQ ID NO: 15 | SEQ ID NO: 63 |
| F20-VH-GL1-V14/B08-VL-GL7 | SEQ ID NO: 16 | SEQ ID NO: 63 |
| F20-VH-GL1-V1-V9/B08-VL-GL7 | SEQ ID NO: 17 | SEQ ID NO: 63 |
| F20-VH-GL1-V1-V9-V14/B08-VL-GL7 | SEQ ID NO: 18 | SEQ ID NO: 63 |
| F20-VH-GL1-V4-V9/B08-VL-GL7 | SEQ ID NO: 19 | SEQ ID NO: 63 |
| F20-VH-GL1-V4-V9-V14/B08-VL-GL7 | SEQ ID NO: 20 | SEQ ID NO: 63 |
| F20-VH-GL2/B08-VL-GL7 | SEQ ID NO: 48 | SEQ ID NO: 63 |
| F20-VH-GL1-V2/B08-VL-GL7 | SEQ ID NO: 53 | SEQ ID NO: 63 |
| F20-VH-GL1-V3/B08-VL-GL7 | SEQ ID NO: 54 | SEQ ID NO: 63 |
| F20-VH-GL1-V11/B08-VL-GL7 | SEQ ID NO: 55 | SEQ ID NO: 63 |
| F20-VH-GL1-V13/B08-VL-GL7 | SEQ ID NO: 56 | SEQ ID NO: 63 |
| F20-VH/B03-VLc | SEQ ID NO: 11 | SEQ ID NO: 67 |
| F20-VH-GL1/B03-VLc | SEQ ID NO: 12 | SEQ ID NO: 67 |
| F20-VH-GL1-V1/B03-VLc | SEQ ID NO: 13 | SEQ ID NO: 67 |
| F20-VH-GL1-V4/B03-VLc | SEQ ID NO: 14 | SEQ ID NO: 67 |
| F20-VH-GL1-V9/B03-VLc | SEQ ID NO: 15 | SEQ ID NO: 67 |
| F20-VH-GL1-V14/B03-VLc | SEQ ID NO: 16 | SEQ ID NO: 67 |
| F20-VH-GL1-V1-V9/B03-VLc | SEQ ID NO: 17 | SEQ ID NO: 67 |
| F20-VH-GL1-V1-V9-V14/B03-VLc | SEQ ID NO: 18 | SEQ ID NO: 67 |
| F20-VH-GL1-V4-V9/B03-VLc | SEQ ID NO: 19 | SEQ ID NO: 67 |
| F20-VH-GL1-V4-V9-V14/B03-VLc | SEQ ID NO: 20 | SEQ ID NO: 67 |
| F20-VH/B03-VL-GL1c | SEQ ID NO: 11 | SEQ ID NO: 68 |
| F20-VH-GL1/B03-VL-GL1c | SEQ ID NO: 12 | SEQ ID NO: 68 |
| F20-VH-GL1-V1/B03-VL-GL1c | SEQ ID NO: 13 | SEQ ID NO: 68 |
| F20-VH-GL1-V4/B03-VL-GL1c | SEQ ID NO: 14 | SEQ ID NO: 68 |
| F20-VH-GL1-V9/B03-VL-GL1c | SEQ ID NO: 15 | SEQ ID NO: 68 |
| F20-VH-GL1-V14/B03-VL-GL1c | SEQ ID NO: 16 | SEQ ID NO: 68 |
| F20-VH-GL1-V1-V9/B03-VL-GL1c | SEQ ID NO: 17 | SEQ ID NO: 68 |
| F20-VH-GL1-V1-V9-V14/B03-VL-GL1c | SEQ ID NO: 18 | SEQ ID NO: 68 |
| F20-VH-GL1-V4-V9/B03-VL-GL1c | SEQ ID NO: 19 | SEQ ID NO: 68 |
| F20-VH-GL1-V4-V9-V14/B03-VL-GL1c | SEQ ID NO: 20 | SEQ ID NO: 68 |
| F20-VH/B08-VLc | SEQ ID NO: 11 | SEQ ID NO: 69 |
| F20-VH-GL1/B08-VLc | SEQ ID NO: 12 | SEQ ID NO: 69 |
| F20-VH-GL1-V1/B08-VLc | SEQ ID NO: 13 | SEQ ID NO: 69 |
| F20-VH-GL1-V4/B08-VLc | SEQ ID NO: 14 | SEQ ID NO: 69 |
| F20-VH-GL1-V9/B08-VLc | SEQ ID NO: 15 | SEQ ID NO: 69 |
| F20-VH-GL1-V14/B08-VLc | SEQ ID NO: 16 | SEQ ID NO: 69 |
| F20-VH-GL1-V1-V9/B08-VLc | SEQ ID NO: 17 | SEQ ID NO: 69 |
| F20-VH-GL1-V1-V9-V14/B08-VLc | SEQ ID NO: 18 | SEQ ID NO: 69 |
| F20-VH-GL1-V4-V9/B08-VLc | SEQ ID NO: 19 | SEQ ID NO: 69 |
| F20-VH-GL1-V4-V9-V14/B08-VLc | SEQ ID NO: 20 | SEQ ID NO: 69 |
| F20-VH/B08-VL-GL6c | SEQ ID NO: 11 | SEQ ID NO: 70 |
| F20-VH-GL1/B08-VL-GL6c | SEQ ID NO: 12 | SEQ ID NO: 70 |
| F20-VH-GL1-V1/B08-VL-GL6c | SEQ ID NO: 13 | SEQ ID NO: 70 |
| F20-VH-GL1-V4/B08-VL-GL6c | SEQ ID NO: 14 | SEQ ID NO: 70 |
| F20-VH-GL1-V9/B08-VL-GL6c | SEQ ID NO: 15 | SEQ ID NO: 70 |
| F20-VH-GL1-V14/B08-VL-GL6c | SEQ ID NO: 16 | SEQ ID NO: 70 |
| F20-VH-GL1-V1-V9/B08-VL-GL6c | SEQ ID NO: 17 | SEQ ID NO: 70 |
| F20-VH-GL1-V1-V9-V14/B08-VL-GL6c | SEQ ID NO: 18 | SEQ ID NO: 70 |
| F20-VH-GL1-V4-V9/B08-VL-GL6c | SEQ ID NO: 19 | SEQ ID NO: 70 |
| F20-VH-GL1-V4-V9-V14/B08-VL-GL6c | SEQ ID NO: 20 | SEQ ID NO: 70 |
| F20-VH-GL2/B03-VLc | SEQ ID NO: 48 | SEQ ID NO: 67 |
| F20-VH-GL1-V2/B03-VLc | SEQ ID NO: 53 | SEQ ID NO: 67 |
| F20-VH-GL1-V3/B03-VLc | SEQ ID NO: 54 | SEQ ID NO: 67 |
| F20-VH-GL1-V11/B03-VLc | SEQ ID NO: 55 | SEQ ID NO: 67 |
| F20-VH-GL1-V13/B03-VLc | SEQ ID NO: 56 | SEQ ID NO: 67 |
| F20-VH-GL2/B03-VL-GL1c | SEQ ID NO: 48 | SEQ ID NO: 68 |
| F20-VH-GL1-V2/B03-VL-GL1c | SEQ ID NO: 53 | SEQ ID NO: 68 |
| F20-VH-GL1-V3/B03-VL-GL1c | SEQ ID NO: 54 | SEQ ID NO: 68 |
| F20-VH-GL1-V11/B03-VL-GL1c | SEQ ID NO: 55 | SEQ ID NO: 68 |
| F20-VH-GL1-V13/B03-VL-GL1c | SEQ ID NO: 56 | SEQ ID NO: 68 |
| F20-VH-GL2/B08-VLc | SEQ ID NO: 48 | SEQ ID NO: 69 |
| F20-VH-GL1-V2/B08-VLc | SEQ ID NO: 53 | SEQ ID NO: 69 |
| F20-VH-GL1-V3/B08-VLc | SEQ ID NO: 54 | SEQ ID NO: 69 |
| F20-VH-GL1-V11/B08-VLc | SEQ ID NO: 55 | SEQ ID NO: 69 |
| F20-VH-GL1-V13/B08-VLc | SEQ ID NO: 56 | SEQ ID NO: 69 |
| F20-VH-GL2/B08-VL-GL6c | SEQ ID NO: 48 | SEQ ID NO: 70 |
| F20-VH-GL1-V2/B08-VL-GL6c | SEQ ID NO: 53 | SEQ ID NO: 70 |
| F20-VH-GL1-V3/B08-VL-GL6c | SEQ ID NO: 54 | SEQ ID NO: 70 |
| F20-VH-GL1-V11/B08-VL-GL6c | SEQ ID NO: 55 | SEQ ID NO: 70 |
| F20-VH-GL1-V13/B08-VL-GL6c | SEQ ID NO: 56 | SEQ ID NO: 70 |

Thus, in a specific embodiment, MMP9 binding proteins according to the invention include isolated antibodies specific for MMP9 or antigen-binding fragments thereof, comprising:

(1) a heavy chain variable region selected among:
  (i) the amino acid sequence of SEQ ID NO: 11
  (ii) the amino acid sequence of SEQ ID NO: 12
  (iii) the amino acid sequence of SEQ ID NO: 13
  (iv) the amino acid sequence of SEQ ID NO: 14
  (v) the amino acid sequence of SEQ ID NO: 15
  (vi) the amino acid sequence of SEQ ID NO: 16
  (vii) the amino acid sequence of SEQ ID NO: 17
  (viii) the amino acid sequence of SEQ ID NO: 18
  (ix) the amino acid sequence of SEQ ID NO: 19
  (x) the amino acid sequence of SEQ ID NO: 20
  (xi) the amino acid sequence of SEQ ID NO: 48
  (xii) the amino acid sequence of SEQ ID NO: 53
  (xiii) the amino acid sequence of SEQ ID NO: 54
  (xiv) the amino acid sequence of SEQ ID NO: 55
  (xv) the amino acid sequence of SEQ ID NO: 56, and
(2) a light chain variable region selected among:
  (i) the amino acid sequence of SEQ ID NO: 24
  (ii) the amino acid sequence of SEQ ID NO: 25
  (iii) the amino acid sequence of SEQ ID NO: 29
  (iv) the amino acid sequence of SEQ ID NO: 30
  (v) the amino acid sequence of SEQ ID NO: 57
  (vi) the amino acid sequence of SEQ ID NO: 58
  (vii) the amino acid sequence of SEQ ID NO: 59
  (viii) the amino acid sequence of SEQ ID NO: 60
  (ix) the amino acid sequence of SEQ ID NO: 61
  (x) the amino acid sequence of SEQ ID NO: 62
  (xi) the amino acid sequence of SEQ ID NO: 63
  (xii) the amino acid sequence of SEQ ID NO: 67
  (xiii) the amino acid sequence of SEQ ID NO: 68
  (xiv) the amino acid sequence of SEQ ID NO: 69
  (xv) the amino acid sequence of SEQ ID NO: 70.

Thus, in a specific embodiment, MMP9 binding proteins according to the invention include isolated antibodies specific for MMP9 or antigen-binding fragments thereof, comprising:
(1) a heavy chain variable region selected among:
  (i) the amino acid sequence of SEQ ID NO: 11
  (ii) the amino acid sequence of SEQ ID NO: 12
  (iii) the amino acid sequence of SEQ ID NO: 13
  (iv) the amino acid sequence of SEQ ID NO: 14
  (v) the amino acid sequence of SEQ ID NO: 15
  (vi) the amino acid sequence of SEQ ID NO: 16
  (vii) the amino acid sequence of SEQ ID NO: 17
  (viii) the amino acid sequence of SEQ ID NO: 18
  (ix) the amino acid sequence of SEQ ID NO: 19
  (x) the amino acid sequence of SEQ ID NO: 20
  (xi) the amino acid sequence of SEQ ID NO: 48
  (xii) the amino acid sequence of SEQ ID NO: 53
  (xiii) the amino acid sequence of SEQ ID NO: 54
  (xiv) the amino acid sequence of SEQ ID NO: 55
  (xv) the amino acid sequence of SEQ ID NO: 56, and
(2) a light chain variable region selected among:
  (i) the amino acid sequence of SEQ ID NO: 57
  (ii) the amino acid sequence of SEQ ID NO: 58
  (iii) the amino acid sequence of SEQ ID NO: 59
  (iv) the amino acid sequence of SEQ ID NO: 60
  (v) the amino acid sequence of SEQ ID NO: 61
  (vi) the amino acid sequence of SEQ ID NO: 62
  (vii) the amino acid sequence of SEQ ID NO: 63
  (viii) the amino acid sequence of SEQ ID NO: 67
  (ix) the amino acid sequence of SEQ ID NO: 68
  (x) the amino acid sequence of SEQ ID NO: 69
  (xi) the amino acid sequence of SEQ ID NO: 70.

Thus, in a specific embodiment, MMP9 binding proteins according to the invention include isolated antibodies specific for MMP9 or antigen-binding fragments thereof, comprising:
(1) a heavy chain variable region selected among:
  (i) the amino acid sequence of SEQ ID NO: 12
  (ii) the amino acid sequence of SEQ ID NO: 17
  (iii) the amino acid sequence of SEQ ID NO: 18
  (iv) the amino acid sequence of SEQ ID NO: 19
  (v) the amino acid sequence of SEQ ID NO: 20, and
(2) a light chain variable region selected among:
  (i) the amino acid sequence of SEQ ID NO: 68
  (ii) the amino acid sequence of SEQ ID NO: 70.

Thus, in a specific embodiment, MMP9 binding proteins according to the invention include isolated antibodies specific for MMP9 or antigen-binding fragments thereof, comprising:
(1) a heavy chain variable region selected among:
  (i) the amino acid sequence of SEQ ID NO: 12
  (ii) the amino acid sequence of SEQ ID NO: 18
  (iii) the amino acid sequence of SEQ ID NO: 20, and
(2) a light chain variable region amino acid sequence of SEQ ID NO: 68.

Thus, in a specific embodiment, MMP9 binding proteins according to the invention include isolated antibodies specific for MMP9 or antigen-binding fragments thereof, comprising:
(1) a heavy chain variable region selected among:
  (i) the amino acid sequence of SEQ ID NO: 12
  (ii) the amino acid sequence of SEQ ID NO: 17
  (iii) the amino acid sequence of SEQ ID NO: 18
  (iv) the amino acid sequence of SEQ ID NO: 19
  (v) the amino acid sequence of SEQ ID NO: 20, and
(2) a light chain variable region amino acid sequence of SEQ ID NO: 70.

Thus, in a specific embodiment, MMP9 binding proteins according to the invention include isolated antibodies specific for MMP9 or antigen-binding fragments thereof, comprising:
(1) a heavy chain variable region selected among:
  (i) the amino acid sequence of SEQ ID NO: 11
  (ii) the amino acid sequence of SEQ ID NO: 12
  (iii) the amino acid sequence of SEQ ID NO: 13
  (iv) the amino acid sequence of SEQ ID NO: 14
  (v) the amino acid sequence of SEQ ID NO: 15
  (vi) the amino acid sequence of SEQ ID NO: 16
(2) a light chain variable region selected among:
  (i) the amino acid sequence of SEQ ID NO: 24
  (ii) the amino acid sequence of SEQ ID NO: 25.

In another specific embodiment, MMP9 binding proteins according to the invention include isolated antibodies specific for MMP9 or antigen-binding fragments thereof, comprising:
(1) a heavy chain variable region selected among:
  (i) the amino acid sequence of SEQ ID NO: 12
  (ii) the amino acid sequence of SEQ ID NO: 17
  (iii) the amino acid sequence of SEQ ID NO: 18
  (iv) the amino acid sequence of SEQ ID NO: 19
  (v) the amino acid sequence of SEQ ID NO: 20, and
(2) a light chain variable region selected among:
  (i) the amino acid sequence of SEQ ID NO: 24
  (ii) the amino acid sequence of SEQ ID NO: 25.

More particularly, isolated antibodies specific for MMP9 or antigen-binding fragments thereof according to the invention can comprise:
- (1) a heavy chain variable region selected among:
  - (i) the amino acid sequence of SEQ ID NO: 18
  - (ii) the amino acid sequence of SEQ ID NO: 20, and
- (2) a light chain variable region of amino acid sequence SEQ ID NO: 25.

In another particular embodiment, MMP9 binding proteins according to the invention include isolated antibodies specific for MMP9 or antigen-binding fragments thereof, comprising:
- (1) a heavy chain variable region selected among:
  - (i) the amino acid sequence of SEQ ID NO: 11
  - (ii) the amino acid sequence of SEQ ID NO: 12
  - (iii) the amino acid sequence of SEQ ID NO: 13
  - (iv) the amino acid sequence of SEQ ID NO: 14
  - (v) the amino acid sequence of SEQ ID NO: 15
  - (vi) the amino acid sequence of SEQ ID NO: 16, and
- (2) a light chain variable region selected among:
  - (i) the amino acid sequence of SEQ ID NO: 29
  - (ii) the amino acid sequence of SEQ ID NO: 30

In another specific embodiment, MMP9 binding proteins according to the invention include isolated antibodies specific for MMP9 or antigen-binding fragments thereof, comprising:
- (1) a heavy chain variable region selected among:
  - (i) the amino acid sequence of SEQ ID NO: 12
  - (ii) the amino acid sequence of SEQ ID NO: 17
  - (iii) the amino acid sequence of SEQ ID NO: 18
  - (iv) the amino acid sequence of SEQ ID NO: 19
  - (v) the amino acid sequence of SEQ ID NO: 20, and
- (2) a light chain variable region selected among:
  - (i) the amino acid sequence of SEQ ID NO: 29
  - (ii) the amino acid sequence of SEQ ID NO: 30.

More particularly, isolated antibodies specific for MMP9 or antigen-binding fragments thereof according to the invention can comprise:
- (1) a heavy chain variable region selected among:
  - (i) the amino acid sequence of SEQ ID NO: 17
  - (ii) the amino acid sequence of SEQ ID NO: 18
  - (iii) the amino acid sequence of SEQ ID NO: 19
  - (iv) the amino acid sequence of SEQ ID NO: 20, and
- (2) a light chain variable region of amino acid sequence SEQ ID NO: 30.

More particularly, isolated antibody specific for MMP9 or antigen-binding fragments thereof according to the invention can comprise a heavy chain variable region of SEQ ID NO: 19 and a light chain variable region of SEQ ID NO: 70.

Conjugates Comprising an Auxiliary Molecule

In another aspect of the invention, the isolated antibodies or antigen-binding fragment thereof according to the invention are optionally conjugated to an accessory molecule, and are then also referred to herein as "conjugated antibodies or "conjugated antibody fragments".

The accessory molecule may be conjugated to the antibody or antibody fragment directly or via a spacer of suitable length for instance as described in Kellogg et al., 2011, *Bioconjug Chem*, 22: 717-27).

In one embodiment, particularly adapted for therapeutic purposes, the accessory molecule can be a therapeutic effector group such as a cytotoxic (e.g. an enzymatically active toxin of bacterial, fungal, plant or animal origin, or fragment thereof), cytostatic, or immunomodulatory agent, including radioactive groups (i.e groups comprising a radionuclide or radioisotope), or small molecules.

In another embodiment, the accessory molecule comprises an antigen-binding fragment of an antibody, which, when conjugated to the antibody or antibody fragment according to the invention, form a bispecific antibody. In particular, said bispecific antibody may be directed to two different MMPs or to two different epitopes of one MMP such as two different epitopes of MMP9.

In a specific embodiment, the accessory molecule may be, for example, an agent active for the treatment of a disease, such as, for the treatment of Crohn's disease: the variable region of an anti-TNFα antibody, which, when conjugated to an antibody or antigen-binding fragment of the invention can form bi-specific anti-TNFα/MMP9 antibodies for the treatment of subjects suffering from moderate to severe Crohn's disease.

The conjugated antibodies and conjugated antibody fragments according to the invention can target the drug in vivo to a site of disease (e.g. a site of inflammation or a tumor) such that the conjugated auxiliary molecule can have a therapeutic effect on the site of disease.

In an alternative embodiment, particularly adapted for diagnostic purposes, the accessory molecule can be, for example, a labeling group including radioisotopes (e.g. 3H, 14C, 32P, 35S, 125I), chromogenic labels, e.g. enzymes which can be used to convert a substrate to a detectable colored (e.g. horseradish peroxidase, alkaline phosphatase, β-galactosidase) or fluorescent compound (e.g. Green Fluorescent Protein, Red Fluorescent Protein), spectroscopic labels (e.g. fluorescent labels such as fluorescein and its derivatives like FITC, Texas red, cyanine dyes, photocyan, rhodamine, or labels presenting a visible color), luminescent labels including luciferins, affinity labels which may be developed by a further compound specific for the label and allowing easy detection and quantification, or any other label used in standard ELISA.

Nucleic Acids Encoding the Polypeptides of the Invention

According to another embodiment, it is provided an isolated nucleic acid molecule encoding an antibody or antigen-binding fragment thereof according to the invention.

The isolated nucleic acid according to the invention may be, for instance, natural DNA or RNA or a recombinant or synthetic DNA, RNA or LNA or a recombinant nucleic acid molecule comprising any of the nucleic acid molecules according to the invention either alone or in combination. In a particular embodiment, the nucleic acid molecules according to the invention are cDNA.

In a particular embodiment, it is provided an isolated nucleic acid comprising one or more of:
- (1) a nucleic acid sequence encoding a heavy chain CDR1 of SEQ ID NO: 2, a heavy chain CDR2 of SEQ ID NO: 3, a heavy chain CDR3 of SEQ ID NO: 4, or a variant thereof wherein 1, 2, or 3 amino acids of said heavy chain CDR is substituted by a different amino acid, and
- (2) (i) a nucleic acid encoding a light chain CDR1 of SEQ ID NO: 21, a light chain CDR2 of SEQ ID NO: 22, a light chain CDR3 of SEQ ID NO: 23, or a variant thereof wherein 1, 2, or 3 amino acids of said light chain CDR is substituted by a different amino acid, or
- (2) (ii) a nucleic acid encoding a light chain CDR1 of SEQ ID NO: 26, a light chain CDR2 of SEQ ID NO: 27, a light chain CDR3 of SEQ ID NO: 28, or a variant thereof wherein 1, 2, or 3 amino acids of said light chain CDR is substituted by a different amino acid.

In a particular embodiment, it is provided an isolated nucleic acid comprising one or more of:
(1) a nucleic acid sequence encoding a variable region of heavy chain selected among:
  (i) the amino acid sequence of SEQ ID NO: 11
  (ii) the amino acid sequence of SEQ ID NO: 12
  (iii) the amino acid sequence of SEQ ID NO: 13
  (iv) the amino acid sequence of SEQ ID NO: 14
  (v) the amino acid sequence of SEQ ID NO: 15
  (vi) the amino acid sequence of SEQ ID NO: 16
  (vii) the amino acid sequence of SEQ ID NO: 17
  (viii) the amino acid sequence of SEQ ID NO: 18
  (ix) the amino acid sequence of SEQ ID NO: 19
  (x) the amino acid sequence of SEQ ID NO: 20
  (xi) the amino acid sequence of SEQ ID NO: 48
  (xii) the amino acid sequence of SEQ ID NO: 53
  (xiii) the amino acid sequence of SEQ ID NO: 54
  (xiv) the amino acid sequence of SEQ ID NO: 55
  (xv) the amino acid sequence of SEQ ID NO: 56
(2) a nucleic acid sequence encoding a variable region of light chain selected among:
  (i) the amino acid sequence of SEQ ID NO: 24
  (ii) the amino acid sequence of SEQ ID NO: 25
  (iii) the amino acid sequence of SEQ ID NO: 29
  (iv) the amino acid sequence of SEQ ID NO: 30
  (v) the amino acid sequence of SEQ ID NO: 57
  (vi) the amino acid sequence of SEQ ID NO: 58
  (vii) the amino acid sequence of SEQ ID NO: 59
  (viii) the amino acid sequence of SEQ ID NO: 60
  (ix) the amino acid sequence of SEQ ID NO: 61
  (x) the amino acid sequence of SEQ ID NO: 62
  (xi) the amino acid sequence of SEQ ID NO: 63
  (xii) the amino acid sequence of SEQ ID NO: 67
  (xiii) the amino acid sequence of SEQ ID NO: 68
  (xiv) the amino acid sequence of SEQ ID NO: 69
  (xv) the amino acid sequence of SEQ ID NO: 70.

In a particular embodiment, it is provided an isolated nucleic acid comprising one or more of:
(1) a nucleic acid sequence encoding a heavy chain variable region selected among:
  (i) the amino acid sequence SEQ ID NO: 11,
  (ii) the amino acid sequence SEQ ID NO: 12
  (iii) the amino acid sequence SEQ ID NO: 13
  (iv) the amino acid sequence SEQ ID NO: 14
  (v) the amino acid sequence SEQ ID NO: 15
  (vi) the amino acid sequence SEQ ID NO: 16, and
(2) a nucleic acid sequence encoding a light chain variable region selected among:
  (i) the amino acid sequence SEQ ID NO: 24
  (ii) the amino acid sequence SEQ ID NO: 25.

In an alternative particular embodiment, the invention provides an isolated nucleic acid comprising one or more of:
(1) a nucleic acid sequence encoding a heavy chain variable region selected among:
  (i) the amino acid sequence SEQ ID NO: 12
  (ii) the amino acid sequence SEQ ID NO: 17
  (iii) the amino acid sequence SEQ ID NO: 18
  (iv) the amino acid sequence SEQ ID NO: 19
  (v) the amino acid sequence SEQ ID NO: 20, and
(2) a nucleic acid sequence encoding a light chain variable region of amino acid sequence SEQ ID NO: 25.

In another particular embodiment, it is provided an isolated nucleic acid comprising one or more of:
(1) a nucleic acid sequence encoding a heavy chain variable region selected among:
  (i) the amino acid sequence SEQ ID NO: 11
  (ii) the amino acid sequence SEQ ID NO: 12
  (iii) the amino acid sequence SEQ ID NO: 13
  (iv) the amino acid sequence SEQ ID NO: 14
  (v) the amino acid sequence SEQ ID NO: 15
  (vi) the amino acid sequence SEQ ID NO: 16, and
(2) a nucleic acid sequence encoding a light chain variable region selected among:
  (i) the amino acid sequence SEQ ID NO: 29
  (ii) the amino acid sequence SEQ ID NO: 30.

In an alternative particular embodiment, it is provided an isolated nucleic acid comprising one or more of:
(1) a nucleic acid sequence encoding a heavy chain variable region selected among:
  (i) the amino acid sequence SEQ ID NO: 12
  (ii) the amino acid sequence SEQ ID NO: 17
  (iii) the amino acid sequence SEQ ID NO: 18
  (iv) the amino acid sequence SEQ ID NO: 19
  (v) the amino acid sequence SEQ ID NO: 20, and
(2) a nucleic acid sequence encoding a light chain variable region of amino acid sequence SEQ ID NO: 30.

In another particular embodiment, it is provided an isolated nucleic acid comprising one or more of:
(1) a nucleic acid sequence comprising SEQ ID NO: 31, SEQ ID NO: 32, and SEQ ID NO: 33, or a variant thereof having at least 80%, at least 90%, at least 95%, at least 96%, at least 97%, at least 98%, or at least 99% identity with one of said sequences, and/or
(2) a nucleic acid sequence selected from:
  a) a nucleic acid sequence comprising SEQ ID NO: 34, SEQ ID NO: 35, and SEQ ID NO: 36, or a variant thereof having at least 80%, at least 90%, at least 95%, at least 96%, at least 97%, at least 98%, or at least 99% identity with one of said sequences,
  b) a nucleic acid sequence comprising SEQ ID NO: 37, SEQ ID NO: 38, SEQ ID NO: 39, or a variant thereof having at least 80%, at least 90%, at least 95%, at least 96%, at least 97%, at least 98%, or at least 99% identity with one of said sequences.

Vectors and Host Cells for Production and Purification of the Polypeptides of the Invention In one embodiment, the invention provides a recombinant expression vector comprising a nucleic acid molecule according to the invention, wherein the vector optionally comprises an expression control sequence, allowing expression in prokaryotic or eukaryotic host cells of the encoded polypeptide, operably linked to said nucleic acid molecule.

Numerous expression systems can be used, including without limitation chromosomes, episomes, and derived viruses. More particularly, the recombinant vectors used can be derived from bacterial plasmids, transposons, yeast episomes, insertion elements, yeast chromosome elements, viruses such as baculovirus, papilloma viruses such as SV40, vaccinia viruses, adenoviruses, fox pox viruses, pseudorabies viruses, retroviruses. These recombinant vectors can equally be cosmid or phagemid derivatives.

The nucleic acid sequence can be inserted in the recombinant expression vector by methods well known to a person skilled in the art such as, for example, those that are described in MOLECULAR CLONING: A LABORATORY MANUAL, Sambrook et al., 4$^{th}$ Ed., Cold Spring Harbor Laboratory Press, Cold Spring Harbor, N.Y., 2001.

The recombinant vector can include nucleotide sequences that allow, control or regulate the expression and the transcription of a polynucleotide of the invention as well as the translation of a polypeptide of the invention, these sequences being selected according to the host cells that are used.

Thus, for example, an appropriate secretion signal can be integrated in the recombinant vector so that the polypeptide, encoded by the nucleic acid molecule of the invention, will be directed towards the lumen of the endoplasmic reticulum, towards the periplasmic space, on the membrane or towards the extracellular environment. The choice of an appropriate secretion signal may facilitate subsequent protein purification.

In a further embodiment, it is provided a host cell comprising a recombinant vector according to the invention.

The introduction of the recombinant vector in a host cell can be carried out according to methods that are well known to a person skilled in the art, such as those described in BASIC METHODS IN MOLECULAR BIOLOGY, Davis et al., 2nd ed., McGraw-Hill Professional Publishing, 1995, and MOLECULAR CLONING: A LABORATORY MANUAL, supra, such as transfection by calcium phosphate, transfection by DEAE dextran, transfection, microinjection, transfection by cationic lipids, electroporation, transduction or infection.

The host cell can be, for example, bacterial cells such as *E. coli* or *Streptomyces*, cells of fungi such as *Aspergillus* and yeasts such as *Saccharomyces*, insect cells, Chinese Hamster Ovary cells (CHO), C127 mouse cell line, BHK cell line of Syrian hamster cells, Human Embryonic Kidney 293 (HEK 293) cells. In a particular embodiment, the host cell is a CHO cell or a HEK 293 cell.

The host cells can be used, for example, to express a polypeptide of the invention. After purification by standard methods, the polypeptide of the invention can be used in a method described hereinafter.

For instance, when expression systems that secrete the recombinant protein are employed, the culture medium may first be concentrated using a commercially available protein concentration filter, for example, an Amicon or Millipore Pellicon ultrafiltration unit. Following the concentration step, the concentrate can be applied to a purification matrix such as a gel filtration matrix. Alternatively, an anion exchange and/or an affinity resin can be employed. The matrices can be acrylamide, agarose, dextran, cellulose or other types commonly employed in protein purification. Alternatively, a cation exchange step can be employed. Finally, one or more reversed-phase high performance liquid chromatography (RP-HPLC) steps employing hydrophobic RP-HPLC media can be employed to further purify the antibodies or fragments thereof. Some or all of the foregoing purification steps, in various combinations, are well known and can be employed to provide a substantially homogeneous recombinant protein.

Recombinant protein produced in bacterial culture can be isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Microbial cells can be disrupted by any convenient method, including freeze-thaw cycling, sonication, mechanical disruption, or use of cell lysing agents.

In another embodiment, the invention provides a process for producing cells capable of expressing a polypeptide according to the invention, comprising genetically engineering cells with a vector or a nucleic acid according to the invention In another embodiment, the invention provides a process for producing antibodies or fragments thereof according to the invention comprises culturing a host cell transformed with an expression vector comprising a nucleic sequence that encodes said antibodies or fragments thereof under conditions sufficient to promote expression of said polypeptides. The antibody or fragment thereof according to the invention is then recovered from culture medium or cell extracts, depending upon the expression system employed. As known to the skilled artisan, procedures for purifying a recombinant protein will vary according to such factors as the type of host cells employed and whether or not the recombinant protein is secreted into the culture medium as described above.

Compositions

The invention provides pharmaceutical or therapeutic agents as compositions and methods for treating a patient, preferably a mammalian patient, and most preferably a human patient who is suffering from a medical disorder, and in particular an inflammatory and/or autoimmune disease or a cancer. Alternatively, the invention provides methods for preventing a medical disorder, and in particular an inflammatory and/or autoimmune disease or a cancer.

In one embodiment, is provided a pharmaceutical composition comprising one or more of (i) an antibody specific for MMP9 or antigen-binding fragment thereof according to the invention, (ii) a nucleic acid according to the invention, (iii) a vector according to the invention, and/or (iv) a host cell according to the invention, and at least one pharmaceutically acceptable carrier.

Pharmaceutical compositions of the invention can contain one or more antibodies specific for MMP9 or antigen-binding fragment thereof in any form described herein. Compositions of this invention may further comprise one or more pharmaceutically acceptable additional ingredient(s) such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, freeze-dried forms, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Compositions of this invention may be liquid formulations including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agent include, but are not limited to, sorbitol syrup, methylcellulose, glucose/sugar syrup, gelatin, hydroxyethylcellulose, carboxymethylcellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in Part 5 of *Remington's The Science and Practice of Pharmacy, 22nd Edition,* 2012, Pharmaceutical Press and the University of the Sciences, Philadelphia College of Pharmacy, which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as transdermal formulations comprising aqueous or non-aqueous vehicles including, but not limited to, creams, ointments, lotions, pastes, medicated plaster, patch, or membrane.

Compositions of this invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

The compounds of this invention can also be administered in sustained release forms or from sustained release drug delivery systems. A description of representative sustained release materials can also be found in the incorporated materials in Remington's Pharmaceutical Sciences.

Injectable formulations are particularly appropriate for administering the compositions according to the invention.

In another embodiment, the invention provides an imaging composition or diagnostic composition comprising an antibody specific for MMP9 or an antigen-binding fragment thereof as described herewith.

In another embodiment, the invention provides a diagnostic composition comprising an antibody specific for MMP9 or antigen-binding fragment thereof as described herewith for detection of active MMP9 in subjects.

In another embodiment, the invention provides a diagnostic composition comprising an antibody specific for MMP9 or antigen-binding fragment thereof as described herewith for detection of active MMP9 in subjects, wherein said antibody comprises a heavy chain variable region of SEQ ID NO: 19 and a light chain variable region of SEQ ID NO: 70.

In one embodiment, diagnostic composition according to the invention comprise an antibody specific for MMP9 or antigen-binding fragment thereof as described herewith conjugated to a moiety selected from the group consisting of a radioisotope, a biotin, an avidin, a strepavidin, a chromophore, a fluorophore, a chemiluminescent moiety, a hapten and an enzyme.

The imaging composition or diagnostic composition according to the invention is useful for detecting elevated levels of MMP9 associated with inflammatory and/or autoimmune diseases or cancers.

Combination

According to the invention, an antibody specific for MMP9 or antigen-binding fragment thereof according to the invention can be administered alone or in combination with a co-agent useful in the prevention and/or treatment of an inflammatory and/or autoimmune disease, for example immune modulatory drugs including biologics, small molecules, and vaccines.

Alternatively, an antibody specific for MMP9 or antigen-binding fragment thereof according to the invention can be administered or in combination with a co-agent useful in the treatment of cancer, for example an anti-cancerous drug such as cytotoxic drugs (Folfox, Xelox, Folfirinox, Folfox6, capecitabine, docetaxel (Taxotere), paclitaxel (Taxol), Nab/paclitaxel, 5-fluorouracil (5-FU), 6-mercaptopurine (6-MP), Capecitabine (Xeloda), Cytarabine (Ara-C), Floxuridine, Fludarabine, Gemcitabine (Gemzar), Gemcitabine-Cisplatin, Hydroxyurea, Methotrexate, Pemetrexed (Alimta), ixabepilone (Ixempra), vinblastine (Velban), vincristine (Oncovin), and vinorelbine (Navelbine), Estramustine (Emcyt)), tyrosine kinase inhibitors (imatinib (Gleevec/Glivec), or gefitinib (Iressa), or erlotinib (Tarceva), Afatinib (Giotrif), Axitinib (Inlyta), Bosutinib (Bosulif), Crizotinib (Xalkori), Dasatinib (Sprycel), Lapatinib (Tyverb), Nilotinib (Tasigna), Pazopanib (Votrient), Sorafenib (Nexavar), Sunitinib (Sutent)) and therapeutic antibodies such as trastuzumab (Herceptin), Bevacizumab (Avastin), Cetuximab (Erbitux), Panitumumab (Vectibix), Pertuzumab (Perjeta), ipilimumab (Yervoy), nivolumab (Opdivo) and pembrolizumab (Keytruda) or anti-CD20 antibody rituximab (Rituxan).

The invention encompasses the administration of an antibody specific for MMP9 or antigen-binding fragment thereof wherein the antibody or fragment thereof is administered to an individual prior to, simultaneously or sequentially with other therapeutic regimens or co-agents useful in the prevention and/or treatment of an MMP9-related disease selected from the group consisting of inflammatory and autoimmune diseases, inflammatory bowel diseases, cancers or tumors, fibrotic diseases, cardiovascular diseases, neurological disorders, eye diseases, or any other MMP9-related disease or disorder, in a therapeutically effective amount. The antibody specific for MMP9 or antigen-binding fragment thereof according to the invention that are administered simultaneously with said co-agents can be administered in the same or different compositions and in the same or different routes of administration.

In a particular embodiment, an antibody specific for MMP9 or antigen-binding fragment thereof according to the invention can be administered in combination with an anti-TNFα antibody for the treatment of subjects suffering from moderate to severe Crohn's disease.

Mode of Administration

Compositions of this invention may be administered in any manner including, but not limited to, orally, parenterally, sublingually, transdermally, rectally, transmucosally, topically, via inhalation, via buccal or intranasal administration or intra bladder, or combinations thereof.

Parenteral administration includes, but is not limited to, intravenous, intra-arterial, intra-peritoneal, subcutaneous, intramuscular, intrathecal, and intra-articular. The compositions of this invention may also be administered in the form of an implant, which allows slow release of the compositions as well as a slow controlled i.v. infusion.

In a particular embodiment, an antibody specific for MMP9 or antigen-binding fragment thereof according to the invention is administered systemically or locally.

In a particular embodiment, an antibody specific for MMP9 or antigen-binding fragment thereof according to the invention is administered by subcutaneous or intravenous route.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Typically, therapeutically effective amounts of a pharmaceutically active antibody range from 1 mg to up to 150 mg/kg body weight dose. If the regimen is a continuous infusion, it may be in the range of 0.250 mg to 20 mg per kg of body weight.

In particular, therapeutically effective amounts of a pharmaceutically active antibody range from 1 mg to up to 50 mg/kg body weight dose. If the regimen is a continuous infusion, it may be in the range of 0.250 mg to 13 mg per kg of body weight.

Patients

Typically, patients according to the invention are patients suffering from a MMP9-related disease, in particular a MMP9-related disease selected from the group consisting of inflammatory and autoimmune diseases, cancers or tumors, lung diseases, fibrotic lung diseases, septicemia, muscular dystrophy, allergy, renal fibrosis, scleroderma, dilated cardiomyopathy, Chagas disease, cardiovascular diseases, neuropsychiatric disorders, diabetes, and eye diseases, or any other MMP9-related disease or disorder.

In an embodiment, patients according to the invention are patients suffering from an inflammatory and/or autoimmune disease including, for instance, inflammatory bowel diseases (IBD) including Crohn's disease (CD), ulcerative colitis (UC), indeterminate colitis, collagenous colitis, rheumatoid arthritis (RA), multiple sclerosis (MS), systemic lupus erythematosus (SLE), Sjogren's syndrome, systemic sclerosis, polymyositis, atherosclerosis.

In a particular embodiment, patients according to the invention are patients suffering from inflammatory bowel disease, more particularly penetrating and stricturing Crohn's disease and ulcerative colitis.

In another embodiment, patients according to the invention are patients suffering from a lung disease including asthma, fibrotic lung diseases such as idiopathic pulmonary, chronic obstructive pulmonary disease (COPD), or a disease selected from septicemia, muscular dystrophy, allergy, renal fibrosis, scleroderma, dilated cardiomyopathy, Chagas disease, cardiovascular diseases, neuropsychiatric disorders, diabetes, and eye diseases.

In another embodiment, patients according to the invention are patients suffering from a cancer or tumor including, for instance, haematopoetic cancer, brain cancer, breast cancer, colorectal cancer, head and neck cancer, pancreatic cancer, lung cancer, ovarian cancer, urinary bladder cancer, liver cancer, melanoma, prostate cancer, muscle cancer, mesenchymal cancer, esophagogastric adenocarcinoma, non-small lung cancer, lung squamous cell carcinoma, lung adenocarcinoma, gastric adenocarcinoma, pancreatic adenocarcinoma and hepatocellular carcinoma.

In a particular embodiment, patients according to the invention are patients suffering from colorectal cancer or adenocarcinoma.

In another embodiment, patients according to the invention are patients suffering from a disease selected from the group consisting of inflammatory and autoimmune diseases, inflammatory bowel diseases, cancers or tumors, fibrotic diseases, cardiovascular diseases, neuropsychiatric disorders or eye diseases.

In another embodiment, patients according to the invention are patients suffering from fibrotic diseases, for instance, systemic sclerosis, multifocal fibrosclerosis, sclerodermatous graft versus host disease in bone marrow transplant recipients, nephrogenic systemic fibrosis, pulmonary fibrosis, liver fibrosis, kidney fibrosis, rheumatoid arthritis, Crohn's disease, ulcerative colitis, myelofibrosis and systemic lupus erythematosus.

In another embodiment, patients according to the invention are patients suffering from eye diseases, for instance, fibrotic pathologies of the lens, corneal diseases, diabetic retinopathy, "dry" or "wet" age-related macular degeneration, proliferative vitreoretinopathy, cataract formation, pterygia, keratoconus, age-related macular degeneration and diabetic retinopathy.

In another embodiment, patients according to the invention are patients suffering from cardiovascular diseases, for instance, hypertension, atherosclerosis, myocardial infarction, heart failure or coronary artery disease hypertension, pulmonary hypertension, pulmonary or tricuspid valve disease, aortic and mitral valve disease, aortic coarctation, atherosclerosis, myocardial infarction, heart failure, ischemic cardiomyopathy, dilated cardiomyopathy, chronic arrhythmia, cardiac fibrosis and coronary artery disease.

In another embodiment, patients according to the invention are patients suffering from neurological disorders, for instance, amyotrophic lateral sclerosis, Alzheimer's disease, multiple sclerosis, neuroinflammation, cerebral ischemia and neuropathic pain.

Uses and Methods According to the Invention

The antibody specific for MMP9 or antigen-binding fragment thereof, the nucleic acids, the vectors, the host cells, the compositions according to the invention are for use in the diagnosis, prevention or treatment of disorders associated with, caused by, or accompanied by elevated levels of MMP9 and/or elevated MMP9 activity.

In one embodiment is provided an antibody specific for MMP9 or antigen-binding fragment thereof according to the invention for use as a medicament.

Another embodiment provides an antibody or fragment thereof according to the invention for use in the prevention and/or treatment of a MMP9-related disease selected from the group consisting of inflammatory and autoimmune diseases, cancers or tumors, lung diseases, fibrotic lung diseases, septicemia, muscular dystrophy, allergy, renal fibrosis, scleroderma, dilated cardiomyopathy, Chagas disease, cardiovascular diseases, neuropsychiatric disorders, diabetes, and eye diseases, or any other MMP9-related disease or disorder.

Another embodiment provides an antibody or fragment thereof according to the invention for use in the prevention and/or treatment of a MMP9-related disease selected from the group consisting of inflammatory and autoimmune diseases, inflammatory bowel diseases, cancers or tumors, fibrotic diseases, cardiovascular diseases, neuropsychiatric disorders or eye diseases.

Another particular embodiment provides an antibody or fragment thereof according to the invention for use in the prevention and/or treatment of an inflammatory and/or autoimmune disease, in particular inflammatory bowel diseases (IBD) including Crohn's disease (CD), ulcerative colitis (UC), indeterminate colitis, collagenous colitis, rheumatoid arthritis (RA), multiple sclerosis (MS), systemic lupus erythematosus (SLE), Sjogren's syndrome, systemic sclerosis, polymyositis, atherosclerosis.

Another particular embodiment provides an antibody or fragment thereof according to the invention for use in the prevention and/or treatment of a lung disease including asthma, fibrotic lung diseases such as idiopathic pulmonary, chronic obstructive pulmonary disease (COPD), or a disease selected from septicemia, muscular dystrophy, allergy, renal fibrosis, scleroderma, dilated cardiomyopathy, Chagas disease, cardiovascular diseases, neuropsychiatric disorders, diabetes, and eye diseases.

A still other particular embodiment provides an antibody or fragment thereof according to the invention for use in the prevention and/or treatment of a cancer or tumor, in particular a cancer selected from the group consisting of haematopoetic cancer, brain cancer, breast cancer, head and neck cancer, pancreatic cancer, ovarian cancer, urinary bladder cancer, lung cancer, liver cancer, melanoma, prostate cancer, muscle cancer, mesenchymal cancer, esophagogastric adenocarcinoma, non-small lung cancer, lung squamous cell carcinoma, lung adenocarcinoma, gastric adenocarcinoma, pancreatic adenocarcinoma, hepatocellular carcinoma, more particularly colorectal cancer or adenocarcinoma.

A still other particular embodiment provides an antibody or fragment thereof according to the invention for use in the prevention and/or treatment of a fibrotic disease, in particular systemic sclerosis, multifocal fibrosclerosis, sclerodermatous graft versus host disease in bone marrow transplant recipients, nephrogenic systemic fibrosis, pulmonary fibrosis, liver fibrosis, kidney fibrosis, rheumatoid arthritis, Crohn's disease, ulcerative colitis, myelofibrosis and systemic lupus erythematosus.

A still other particular embodiment provides an antibody or fragment thereof according to the invention for use in the prevention and/or treatment of an eye disease, in particular fibrotic pathologies of the lens, corneal diseases, diabetic retinopathy, "dry" or "wet" age-related macular degeneration, proliferative vitreoretinopathy, cataract formation, pterygia, keratoconus, age-related macular degeneration and diabetic retinopathy.

A still other particular embodiment provides an antibody or fragment thereof according to the invention for use in the prevention and/or treatment of a cardiovascular disease, in particular hypertension, pulmonary hypertension, pulmonary or tricuspid valve disease, aortic and mitral valve disease, aortic coarctation, atherosclerosis, myocardial infarction, heart failure, ischemic cardiomyopathy, dilated cardiomyopathy, chronic arrhythmia, cardiac fibrosis and coronary artery disease.

A still other particular embodiment provides an antibody or fragment thereof according to the invention for use in the prevention and/or treatment of a neurological disorder, in particular amyotrophic lateral sclerosis, Alzheimer's disease, multiple sclerosis, neuroinflammation, cerebral ischemia and neuropathic pain.

In another embodiment is provided a use of an antibody specific for MMP9 or antigen-binding fragment thereof according to the invention for the preparation of a pharmaceutical composition for preventing and/or treating a MMP9-related disease selected from the group consisting of inflammatory and autoimmune diseases, cancers or tumors, lung diseases, fibrotic lung diseases, septicemia, muscular dystrophy, allergy, renal fibrosis, scleroderma, dilated cardiomyopathy, Chagas disease, cardiovascular diseases, neuropsychiatric disorders, diabetes, and eye diseases, or any other MMP9-related disease or disorder.

In a specific embodiment is provided a use of an antibody specific for MMP9 or antigen-binding fragment thereof according to the invention for the preparation of a pharmaceutical composition for preventing and/or treating an inflammatory and autoimmune diseases, inflammatory bowel diseases, cancers or tumors, fibrotic diseases, cardiovascular diseases, neuropsychiatric disorders or eye diseases.

In one particular embodiment is provided a use of an antibody specific for MMP9 or antigen-binding fragment thereof according to the invention for the preparation of a pharmaceutical composition for preventing and/or treating an inflammatory and/or autoimmune disease in a subject, in particular for preventing or treating inflammatory bowel diseases (IBD) including Crohn's disease (CD), ulcerative colitis (UC), indeterminate colitis, collagenous colitis, rheumatoid arthritis (RA), multiple sclerosis (MS), systemic lupus erythematosus (SLE), Sjogren's syndrome, systemic sclerosis, polymyositis, atherosclerosis.

In a specific embodiment is provided a use of an antibody specific for MMP9 or antigen-binding fragment thereof according to the invention for the preparation of a pharmaceutical composition for preventing and/or treating inflammatory bowel disease, in particular penetrating and stricturing Crohn's disease and ulcerative colitis.

In one particular embodiment is provided a use of an antibody specific for MMP9 or antigen-binding fragment thereof according to the invention for the preparation of a pharmaceutical composition for preventing and/or treating a lung disease including asthma, fibrotic lung diseases such as idiopathic pulmonary, chronic obstructive pulmonary disease (COPD), or a disease selected from septicemia, muscular dystrophy, allergy, renal fibrosis, scleroderma, dilated cardiomyopathy, Chagas disease, cardiovascular diseases, neuropsychiatric disorders, diabetes, and eye diseases.

In an alternative embodiment is provided a use of an antibody specific for MMP9 or antigen-binding fragment thereof according to the invention for the preparation of a pharmaceutical composition for preventing and/or treating a cancer or tumor, in particular for preventing and/or treating a cancer selected from the group consisting of haematopoetic cancer, brain cancer, breast cancer, head and neck cancer, pancreatic cancer, ovarian cancer, urinary bladder cancer, lung cancer, liver cancer, melanoma, prostate cancer, muscle cancer, mesenchymal cancer, esophagogastric adenocarcinoma, non-small lung cancer, lung squamous cell carcinoma, lung adenocarcinoma, gastric adenocarcinoma, pancreatic adenocarcinoma, hepatocellular carcinoma, more particularly colorectal cancer or adenocarcinoma.

In a specific embodiment is provided a use of an antibody specific for MMP9 or antigen-binding fragment thereof according to the invention for the preparation of a pharmaceutical composition for preventing and/or treating colorectal cancer or adenocarcinoma.

In a specific embodiment is provided a use of an antibody specific for MMP9 or antigen-binding fragment thereof according to the invention for the preparation of a pharmaceutical composition for preventing and/or treating a fibrotic disease, in particular systemic sclerosis, multifocal fibrosclerosis, sclerodermatous graft versus host disease in bone marrow transplant recipients, nephrogenic systemic fibrosis, pulmonary fibrosis, liver fibrosis, kidney fibrosis, rheumatoid arthritis, Crohn's disease, ulcerative colitis, myelofibrosis and systemic lupus erythematosus.

In a specific embodiment is provided a use of an antibody specific for MMP9 or antigen-binding fragment thereof according to the invention for the preparation of a pharmaceutical composition for preventing and/or treating an eye disease, in particular fibrotic pathologies of the lens, corneal diseases, diabetic retinopathy, "dry" or "wet" age-related macular degeneration, proliferative vitreoretinopathy, cataract formation, pterygia, keratoconus, age-related macular degeneration and diabetic retinopathy.

In a specific embodiment is provided a use of an antibody specific for MMP9 or antigen-binding fragment thereof according to the invention for the preparation of a pharmaceutical composition for preventing and/or treating a cardiovascular disease, in particular hypertension, pulmonary hypertension, pulmonary or tricuspid valve disease, aortic and mitral valve disease, aortic coarctation, atherosclerosis, myocardial infarction, heart failure, ischemic cardiomyopathy, dilated cardiomyopathy, chronic arrhythmia, cardiac fibrosis and coronary artery disease.

In a specific embodiment is provided a use of an antibody specific for MMP9 or antigen-binding fragment thereof according to the invention for the preparation of a pharmaceutical composition for preventing and/or treating a neurological disorder, in particular amyotrophic lateral sclerosis, Alzheimer's disease, multiple sclerosis, neuroinflammation, cerebral ischemia and neuropathic pain.

In another embodiment is provided a method for preventing and/or treating a MMP9-related disease selected from the group consisting of inflammatory and autoimmune diseases, cancers or tumors, lung diseases, fibrotic lung diseases, septicemia, muscular dystrophy, allergy, renal fibrosis, scleroderma, dilated cardiomyopathy, Chagas disease, cardiovascular diseases, neuropsychiatric disorders, diabetes, and eye diseases, or any other MMP9-related disease or disorder comprising administering a therapeutically effective amount of an antibody specific for MMP9 or antigen-binding fragment thereof according to the invention, to a subject in need thereof.

In a particular embodiment is provided a method for preventing and/or treating an inflammatory and autoimmune diseases, inflammatory bowel diseases, cancers or tumors, fibrotic diseases, cardiovascular diseases, neuropsychiatric disorders or eye diseases comprising administering a therapeutically effective amount of an antibody specific for MMP9 or antigen-binding fragment thereof according to the invention, to a subject in need thereof.

In a particular embodiment is provided a method for preventing and/or treating an inflammatory and/or autoimmune disease, in particular for preventing or treating inflammatory bowel diseases (IBD) including Crohn's disease (CD), ulcerative colitis (UC), indeterminate colitis, collagenous colitis, rheumatoid arthritis (RA), multiple sclerosis (MS), systemic lupus erythematosus (SLE), Sjogren's syndrome, systemic sclerosis, polymyositis, atherosclerosis, comprising administering a therapeutically effective amount of an antibody specific for MMP9 or antigen-binding fragment thereof according to the invention, to a subject in need thereof.

In a specific embodiment is provided a method of preventing and/or treating an inflammatory bowel disease, in particular for preventing or treating penetrating and stricturing Crohn's disease and ulcerative colitis, comprising administering a therapeutically effective amount of an antibody specific for MMP9 or antigen-binding fragment thereof according to the invention, to a subject in need thereof.

In another particular embodiment is provided a method for preventing and/or treating a lung disease including asthma, fibrotic lung diseases such as idiopathic pulmonary, chronic obstructive pulmonary disease (COPD), or a disease selected from septicemia, muscular dystrophy, allergy, renal fibrosis, scleroderma, dilated cardiomyopathy, Chagas disease, cardiovascular diseases, neuropsychiatric disorders, diabetes, and eye diseases, comprising administering a therapeutically effective amount of an antibody specific for MMP9 or antigen-binding fragment thereof according to the invention, to a subject in need thereof.

In an alternative embodiment is provided a method of preventing and/or treating a cancer or tumor, in particular for preventing and/or treating a cancer selected from the group consisting of haematopoetic cancer, brain cancer, breast cancer, colorectal cancer, head and neck cancer, pancreatic cancer, lung cancer, liver cancer, melanoma, prostate cancer, muscle cancer, mesenchymal cancer, esophagogastric adenocarcinoma, non-small lung cancer, lung squamous cell carcinoma, lung adenocarcinoma, gastric adenocarcinoma, pancreatic adenocarcinoma, hepatocellular carcinomacolorectal cancer and hepatocellular carcinoma, comprising administering a therapeutically effective amount of an antibody specific for MMP9 or antigen-binding fragment thereof according to the invention, to a subject in need thereof.

In a specific embodiment is provided a method for preventing and/or treating colorectal cancer or adenocarcinoma comprising administering a therapeutically effective amount of an antibody specific for MMP9 or antigen-binding fragment thereof according to the invention, to a subject in need thereof.

In a specific embodiment is provided a method for preventing and/or treating fibrotic disease, in particular systemic sclerosis, multifocal fibrosclerosis, sclerodermatous graft versus host disease in bone marrow transplant recipients, nephrogenic systemic fibrosis, pulmonary fibrosis, liver fibrosis, kidney fibrosis, rheumatoid arthritis, Crohn's disease, ulcerative colitis, myelofibrosis and systemic lupus erythematosus comprising administering a therapeutically effective amount of an antibody specific for MMP9 or antigen-binding fragment thereof according to the invention, to a subject in need thereof.

In a specific embodiment is provided a method for preventing and/or treating eye disease, in particular fibrotic pathologies of the lens, corneal diseases, diabetic retinopathy, "dry" or "wet" age-related macular degeneration, proliferative vitreoretinopathy, cataract formation, pterygia, keratoconus, age-related macular degeneration and diabetic retinopathy comprising administering a therapeutically effective amount of an antibody specific for MMP9 or antigen-binding fragment thereof according to the invention, to a subject in need thereof.

In a specific embodiment is provided a method for preventing and/or treating cardiovascular disease, in particular hypertension, pulmonary hypertension, pulmonary or tricuspid valve disease, aortic and mitral valve disease, aortic coarctation, atherosclerosis, myocardial infarction, heart failure, ischemic cardiomyopathy, dilated cardiomyopathy, chronic arrhythmia, cardiac fibrosis and coronary artery disease comprising administering a therapeutically effective amount of an antibody specific for MMP9 or antigen-binding fragment thereof according to the invention, to a subject in need thereof.

In a specific embodiment is provided a method for preventing and/or treating neurological disorder, in particular amyotrophic lateral sclerosis, Alzheimer's disease, multiple sclerosis, neuroinflammation, cerebral ischemia and neuropathic pain comprising administering a therapeutically effective amount of an antibody specific for MMP9 or antigen-binding fragment thereof according to the invention, to a subject in need thereof.

In an alternative embodiment is provided a method of detecting MMP9 in a biological sample comprising contacting a biological sample from a subject with an antibody specific for MMP9 or antigen-binding fragment thereof according to the invention.

As used herewith "biological sample" refers to cells, tissue samples or cell components (such as cellular membranes or cellular components) obtained from a subject, in particular from a subject suspected of, or suffering from, inflammatory or autoimmune disease and/or cancer or tumor or at high risk of developing such a disorder.

Examples of biological sample include blood, serum, plasma, cerebrospinal fluid, synovial fluid, urine, feces and tissue samples including cells isolated from said tissue. Tissue samples include formalin-fixed or frozen tissue sections.

Any suitable method for detection and analysis of MMP9 can be employed, including diagnostic assay techniques known in the art such as competitive binding assays, direct or indirect sandwich assays and immunoprecipitation assays conducted in either heterogeneous or homogeneous phases.

In a particular embodiment, the invention provides an ex vivo method for detecting the presence and/or concentration of MMP9 protein in a biological sample, comprising the steps of:
(i) Providing a biological sample from a subject,
(ii) Reacting said biological sample with at least one antibody or antigen-binding fragment thereof according to the invention, under conditions sufficient for binding MMP9 protein present in said biological sample to said at least one antibody or fragment thereof through antigen-antibody interactions; and
(iii) Detecting a signal proportional to the level of antigen-antibody complex formed in step (ii),
wherein the intensity of the signal correlates with the concentration of MMP9 protein in the biological sample.

In a particular embodiment, the invention provides an ex vivo method for detecting the presence and/or concentration of active MMP9 protein in a biological sample, comprising the steps of:
(i) Providing a biological sample from a subject,
(ii) Reacting said biological sample with at least one antibody or antigen-binding fragment thereof according to the invention, under conditions sufficient for binding active MMP9 protein present in said biological sample to said at least one antibody or fragment thereof through antigen-antibody interactions; and
(iii) Detecting a signal proportional to the level of antigen-antibody complex formed in step (ii),
wherein the intensity of the signal correlates with the concentration of active MMP9 protein in the biological sample.

In a particular embodiment, the invention provides an ex vivo method for detecting the presence and/or concentration of active MMP9 protein in a biological sample, wherein at least one antibody or antigen-binding fragment thereof according to the invention comprises a heavy chain variable region of SEQ ID NO: 19 and a light chain variable region of SEQ ID NO: 70.

More particularly, it is provided an ex-vivo method of prognosis or diagnosis of an inflammatory and/or autoimmune disease or a cancer associated with an elevated level of MMP9 from a biological sample of a subject comprising the steps of:
(a) Providing a biological sample from a subject;
(b) Bringing said biological sample into contact with a solid matrix where at least one antibody or fragment thereof according to the invention is bound to, wherein the contacting is under conditions sufficient for binding MMP9 protein present in said biological fluid sample to said at least one antibody or fragment thereof through antigen-antibody interactions;
(c) Removing any unbound MMP9 protein from the surface of said solid matrix;
(d) Detecting a signal proportional to the level of antigen-antibody complex bound to said solid matrix,
(e) Comparing the level of signal detected in step (d) with the level of signal detected in the same conditions with a negative control,
wherein a level of signal detected in the subject's sample that is higher than the level of signal detected in the negative control is indicative of an elevated level of MMP9 associated with an inflammatory and/or autoimmune disease or a cancer.

Kit

One aspect of the invention relates to a kit comprising at least one antibody or antigen-binding fragment thereof according to the invention, and/or at least one nucleic acid encoding said antibody or fragment thereof, and/or at least one vector comprising said nucleic acid, and/or at least one host cell according to the invention, and optionally instructional material.

In a particular embodiment, the kit according to the invention comprises at least one antibody or antigen-binding fragment thereof according to the invention, to be coupled or already coupled to a solid matrix.

Examples of solid matrix suitable for the invention include any solid phase support suitable for carrying out an immunoassay or a method according to the invention, such as beads, microparticles, nanoparticles, tubes, fabrics or plates, films, slides, wells, formed from or coated with glass, polystyrene, polypropylene, nitrocellulose, quartz, ceramic, dextran or other materials. For example, the solid matrix is in a form of microtiter wells, such as a 96-well microtiter plate.

The fixation of the antibodies or fragments thereof according to the invention to the solid matrix in a kit according to the invention may be carried out by adsorption or chemical coupling to a solid phase support. Any means known in the art for immobilizing a protein or peptide to a solid support can be used. The antibodies or fragments thereof according to the invention can be either covalently or non-covalently bound to the solid matrix by techniques such as covalent bonding via an amide or ester linkage or adsorption. Peptides can be bound using binding pairs such as biotin and avidin or antibody and antigen. After the peptides are affixed to the solid matrix, the solid matrix can be incubated with a blocking solution (containing a blocking protein such as bovine serum albumin) to reduce non-specific adsorption of antibodies in a test sample to the support surface. According to one aspect, the antibodies or fragment thereof according to the invention can be synthesized directly on the solid matrix of the kit of the invention.

According to one embodiment, when the kit comprises at least one antibody or fragment thereof according to the invention or a combination thereof for coupling to a solid matrix as solid phase support, the kit further optionally comprises coupling reagents and/or a solid matrix for performing an immunoassay.

According to another further embodiment, the kit according to the invention further comprises at least one rinsing reagent for washing unbound material before detection in order to avoid background noise detection. Typically rinsing reagents comprise standard buffers known in the art.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention having been described, the following examples are presented by way of illustration, and not limitation.

EXAMPLES

Example 1: Generation and Isolation of the Anti-MMP9 Antibodies According to the Invention The anti-MMP9 antibodies according to the invention were obtained by carrying out the following steps:

1/ Phage Display Hit Discovery (HD)

A ScFv library was used as a source of ScFv fragments. This library is naive in origin (i.e. constructed using PBMCs of non-immunised healthy human donors), of modest size (about $2.5.10^9$ VH/VL combinations) and contains VH domains derived from the clonally unselected and non-class-switched IgM repertoire. Using this library, ScFv candidates were first selected based on their binding to human or mouse MMP9 (full-length, pro-, and activated forms) by phage display, the ScFvs were reformatted into IgG1 and screened for functional neutralization of MMP9 activity (in particular by determining $IC_{50}$, species selectivity, modality of neutralization (proMMP9 or MMP9). This step allowed the identification of 10 candidate antibodies, which could be divided into two mechanistic classes: those blocking MMP9 activity by interfering with the activation of latent proMMP9 (suggesting that the pro-domain is part of the epitope recognized by the antibodies) and those interfering directly with the catalytic activity of activated MMP9 (suggesting that the CAT_fn domain is part of the epitope recognized by the antibodies).

2/ Hit Optimization (HO) by VL Chain Shuffling for Affinity Maturation:

Four of the HD candidates obtained in the previous step were subjected to hit optimization via lambda light chain shuffling to improve their potency. Basically, parental HD clone VH chains were permutated against the entire VL lambda content of the original library, generating several new clone-specific libraries.

3/ Lead Optimization:

Two HO candidates (F20-VH/B03-VLc and F20-VH/B08-VLc) were selected based on their mechanism of action i.e. inhibition of MMP9 enzymatic activity, for lead optimization and characterization, through in particular (i) optimization by germlining framework residues (as defined by Kabat) to minimize sequence deviation from closest human germline to potentially improve biophysical properties and reduce immunogenicity risk and (ii) change some amino acids or amino acid motifs within the CDRs which might lead to chemical instability or aggregation of antibodies. This strategy allowed the generation of antibodies comprising the VH/VL regions indicated in above Table 2.

In the following examples, the specific VH/VL regions mentioned in Table 3 that follows were reformatted as human IgG4 for further characterization. For this purpose, the nucleic acids encoding the VH and VL chains of interest were cloned in pTT vectors (engineered for cloning compatibility with original chains) for transient co-expression of IgG4 in HEK293 cells.

TABLE 3

| Name | Sequence of Heavy chain variable region | Sequence of Light chain variable region |
|---|---|---|
| F20-VH-GL1/B03-VL-GL1c | SEQ ID NO: 12 | SEQ ID NO: 68 |
| F20-VH-GL1-V1-V9-V14/B03-VL-GL1c | SEQ ID NO: 18 | SEQ ID NO: 68 |
| F20-VH-GL1-V4-V9-V14/B03-VL-GL1c | SEQ ID NO: 20 | SEQ ID NO: 68 |
| F20-VH-GL1/B08-VL-GL6c | SEQ ID NO: 12 | SEQ ID NO: 70 |
| F20-VH-GL1-V1-V9/B08-VL-GL6c | SEQ ID NO: 17 | SEQ ID NO: 70 |
| F20-VH-GL1-V1-V9-V14/B08-VL-GL6c | SEQ ID NO: 18 | SEQ ID NO: 70 |
| F20-VH-GL1-V4-V9/B08-VL-GL6c | SEQ ID NO: 19 | SEQ ID NO: 70 |
| F20-VH-GL1-V4-V9-V14/B08-VL-GL6c | SEQ ID NO: 20 | SEQ ID NO: 70 |

Example 2: Potency and Efficacy of Some Anti-MMP9 Antibodies According to the Invention in Human MMP3/MMP9 and Human MMP9 Activity Assays The functional neutralization of MMP9 catalytic activity towards the fluorogenic polymer substrate DQ-gelatin by some antibodies according to the invention was evaluated.

The signature activity of MMP9 (and MMP2) is gelatin degradation. Gelatin is essentially an irreversibly denatured form derived from various collagens, several of which are considered key physiological substrates for MMP9. Unlike small peptidic substrates, the binding and recognition of gelatin (similar to that of collagen) by MMP9 is complex and known to be mediated via regions of the molecule other than the active site, including the fibronectin and PEX domains. In order to retain these physiologically relevant 'exosite' interactions and to facilitate the isolation of potential 'non-classical' allosteric neutralizer classes, a fluorogenically quenched soluble gelatin polymer (DQ-gelatin) was chosen as the key substrate for plate-based screening and ranking purposes. Substrate hydrolysis was mediated by truncated fragment of MMP9 (ie. pro-domain removed). The assay was performed in two modes.

The first mode, named "MMP9 assay", utilized pre-activated MMP9 (from engineered MMP9 containing a LETD caspase 8 recognition motif at the native cleavage junction) in which the pro-domain was first removed via directed caspase 8 cleavage. The second mode, named "MMP3/MMP9 assay", was devised to incorporate the removal of the pro-domain (i.e. the activation step) as an additional linked process within the assay. This was achieved by combining catalytic domain of human MMP3 (Calbiochem, 444217-5) and full length (latent form) proMMP9 in the assay cocktail together with the DQ-gelatin substrate (Lubio Science, D12054) and test antibodies. MMP3, considered as a physiologically relevant activator of MMP9, has been shown to remove the pro-domain via a two-step sequential mechanism (Ogata et al, 1992, *J. Biol. Chem.* 267(6): 3581-4), and is frequently co-expressed with MMP9 in diseased tissues. Importantly, activated MMP3 itself does not appear to significantly cleave the DQ-gelatin substrate. Hence, DQ-gelatin hydrolysis (emission of fluorescence) in this assay is dependent on MMP3-mediated MMP9 activation and intrinsic MMP9 catalytic activity, which offers the potential to characterize neutralizers that interfere with either process.

Thus, the "MMP3/MMP9 assay" was used to determine the ability of anti-MMP9 antibodies to neutralize proMMP9 activation and its downstream catalytic activity. Briefly, aliquots of recombinant human proMMP9 were pre-incubated with various dilutions of test antibodies for one hour. The digestion was started by adding a recombinant catalytic domain of human MMP3, together with the MMP9-specific fluorescent substrate DQ-Gelatin. Emitted fluorescence signal (Excitation at 485 nm, Emission at 520 nm) is proportional to the digestion of the gelatin substrate, thus to the catalytic activity of mature MMP9 enzyme. The fluorescence signal was plotted against the antibody concentrations and half-maximal inhibitory potencies ($IC_{50}$ values) are deduced from non-linear regression curves.

The "MMP9 assay" was used to determine the capacity of anti-MMP9 antibodies to directly neutralize the catalytic activity of mature MMP9. Briefly, the assay is similar to the "MMP3/MMP9 assay" but uses a catalytically active caspase-cleaved recombinant MMP9 instead of proMMP9, therefore the addition of recombinant catalytic domain of human MMP3 is not required.

Figure 6:
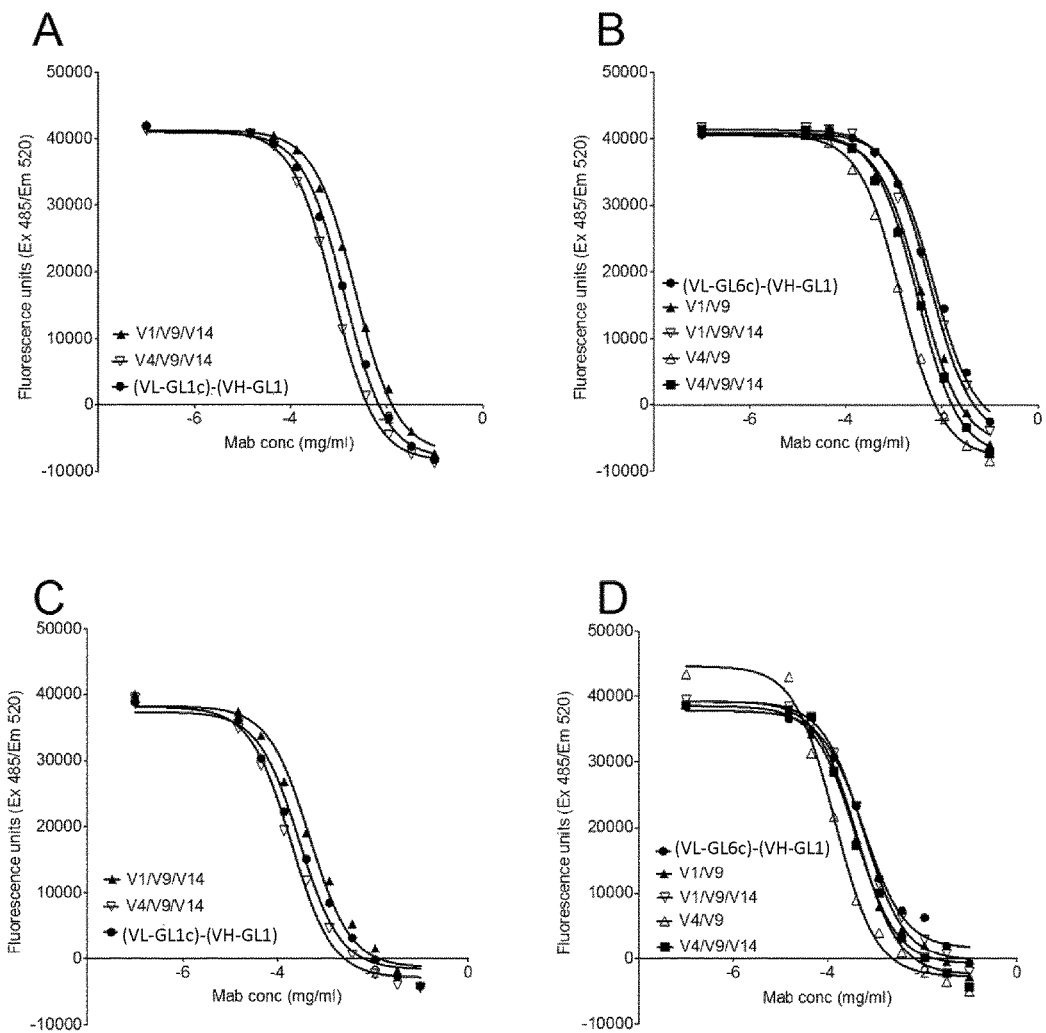
FIG. 6 shows titration of neutralizing activity of exemplary anti-MMP9 antibodies according to the invention (F20-VH/B03-VLc and F20-VH/B08-VLc variants) towards human proMMP9 (A, B) and human mature MMP9 (C, D). F20-VH/B03-VLc variants (A, C), F20-VH/B08-VLc variants (B, D).

All antibodies according to the invention that were tested were able to effectively decrease digestion of DQ-gelatin in both enzymatic assays. This result indicates that all antibodies according to the invention block activation of the proMMP9 to the catalytically active enzyme and/or block the catalytic activity of MMP9 (Table 4, FIG. 6).

TABLE 4

Potency and efficacy of anti-MMP9 antibodies to neutralize processing of human proMMP9 and/or its downstream catalytic activity on gelatin

| Heavy/light variable regions comprised in the antibody | Human MMP9 (i.e. activated MMP9) | | Human proMMP9 | |
|---|---|---|---|---|
| | $IC_{50}$ (nM) | Efficacy | $IC_{50}$ (nM) | Efficacy |
| F20-VH-GL1/B03-VL-GL1c | 1.92 | 100% | 9.05 | 100% |
| F20-VH-GL1-V1-V9-V14/ B03-VL-GL1c | 3.16 | 100% | 15.24 | 100% |
| F20-VH-GL1-V4-V9-V14/ B03-VL-GL1c | 1.30 | 100% | 5.48 | 100% |

TABLE 4-continued

Potency and efficacy of anti-MMP9 antibodies to neutralize processing of human proMMP9 and/or its downstream catalytic activity on gelatin

| Heavy/light variable regions comprised in the antibody | Human MMP9 (i.e. activated MMP9) | | Human proMMP9 | |
|---|---|---|---|---|
| | $IC_{50}$ (nM) | Efficacy | $IC_{50}$ (nM) | Efficacy |
| F20-VH-GL1/B08-VL-GL6c | 3.92 | 100% | 43.99 | 100% |
| F20-VH-GL1-V1-V9/ B08-VL-GL6c | 2.64 | 100% | 23.74 | 100% |
| F20-VH-GL1-V1-V9-V14/ B08-VL-GL6c | 3.86 | 100% | 38.07 | 100% |
| F20-VH-GL1-V4-V9/ B08-VL-GL6c | 0.97 | 100% | 9.52 | 100% |
| F20-VH-GL1-V4-V9-V14/ B08-VL-GL6c | 2.92 | 100% | 20.44 | 100% |

Antibody F20-VH-GL1-V4-V9/B08-VL-GL6c according to the invention was compared with comparative antibody 1 (antibody known as AB0041, that has an amino acid sequence of heavy chain of SEQ ID NO: 44 and of light chain SEQ ID NO: 45) using the "MMP9 assay" with highly purified activated MMP9. Only antibody F20-VH-GL1-V4-V9/B08-VL-GL6c according to the invention effectively decreased digestion of DQ-gelatin with an $IC_{50}$ of 2.6 nM while comparative antibody 1 was inactive. This result indicates that antibody F20-VH-GL1-V4-V9/B08-VL-GL6c according to the invention is an inhibitor of MMP9 enzymatic activity while comparative antibody 1 is not.

In the "MMP3/MMP9 assay", antibody F20-VH-GL1-V4-V9/B08-VL-GL6c according to the invention and comparative antibody 1 effectively decreased digestion of DQ-gelatin with an $IC_{50}$ of 9.52 nM and 0.20 nM, respectively. Taken together, results in these two enzymatic assays indicate that comparative antibody 1 is an inhibitor of MMP9 activation, while antibody F20-VH-GL1-V4-V9/B08-VL-GL6c is an inhibitor of MMP9 catalytic activity and possibly an inhibitor of MMP9 activation.

Example 3: Species-Specificity of Some Anti-MMP9 Antibodies According to the Invention in MMP3/MMP9 Assay The species-specificity of the enzymatic inhibitory activities of anti-MMP9 antibodies was evaluated using the "MMP3/MMP9 assay" described in the Example 2. The enzyme used was either Cynomologus monkey (cyno), rat, or mouse proMMP9.

Some antibodies according to the invention, which were tested, were able to efficiently block the activation and/or the downstream catalytic activity of Cynomologus monkey (cyno), rat, and mouse proMMP9 (Tables 5, 6, and 7 respectively).

TABLE 5

Potency and efficacy of anti-MMP9 antibodies to neutralize cynomolgus monkey proMMP9 in MMP3/MMP9 gelatin assay.

| Heavy/light variable regions comprised in the antibody | Cyno proMMP9 | |
|---|---|---|
| | $IC_{50}$ (nM) | Efficacy |
| F20-VH-GL1/ B03-VL-GL1c | 3.85 | 100% |
| F20-VH-GL1-V1-V9-V14/B03- VL-GL1c | 12.49 | 100% |

TABLE 5-continued

Potency and efficacy of anti-MMP9 antibodies to neutralize cynomolgus monkey proMMP9 in MMP3/MMP9 gelatin assay.

| Heavy/light variable regions comprised in the antibody | Cyno proMMP9 | |
|---|---|---|
| | $IC_{50}$ (nM) | Efficacy |
| F20-VH-GL1-V4-V9-V14/B03-VL-GL1c | 3.75 | 100% |
| F20-VH-GL1/B08-VL-GL6c | 29.89 | 100% |
| F20-VH-GL1-V1-V9/B08-VL-GL6c | 15.79 | 100% |
| F20-VH-GL1-V1-V9-V14/B08-VL-GL6c | 27.57 | 100% |
| F20-VH-GL1-V4-V9/B08-VL-GL6c | 5.86 | 100% |
| F20-VH-GL1-V4-V9-V14/B08-VL-GL6c | 10.80 | 100% |

TABLE 6

Potency and efficacy of anti-MMP9 antibodies to neutralize rat proMMP9 in MMP3/MMP9 gelatin assay.

| Heavy/light variable regions comprised in the antibody | Rat proMMP9 | |
|---|---|---|
| | $IC_{50}$ (nM) | Efficacy |
| F20-VH-GL1/B03-VL-GL1c | 4.99 | 100% |
| F20-VH-GL1-V1-V9-V14/B03-VL-GL1c | 8.82 | 100% |
| F20-VH-GL1-V4-V9-V14/B03-VL-GL1c | 2.83 | 100% |
| F20-VH-GL1/B08-VL-GL6c | 17.41 | 100% |
| F20-VH-GL1-V1-V9/B08-VL-GL6c | 7.77 | 100% |
| F20-VH-GL1-V1-V9-V14/B08-VL-GL6c | 12.28 | 100% |
| F20-VH-GL1-V4-V9/B08-VL-GL6c | 3.16 | 100% |
| F20-VH-GL1-V4-V9-V14/B08-VL-GL6c | 6.19 | 100% |

TABLE 7

Potency and efficacy of anti-MMP9 antibodies to neutralize mouse proMMP9 or active MMP9 in MMP3/MMP9 and MMP9 gelatin assays, respectively.

| Heavy/light variable regions comprised in the antibody | Mouse MMP9 | | Mouse proMMP9 | |
|---|---|---|---|---|
| | $IC_{50}$ (nM) | Efficacy | $IC_{50}$ (nM) | Efficacy |
| F20-VH-GL1/B03-VL-GL1c | 333 | 100% | 38.77 | 25% |
| F20-VH-GL1-V1-V9-V14/B03-VL-GL1c | >500 | ND | >500 | ND |
| F20-VH-GL1-V4-V9-V14/B03-VL-GL1c | 164 | 100% | 462 | 100% |
| F20-VH-GL1/B08-VL-GL6c | 0.86 | 100% | 7.91 | 100% |
| F20-VH-GL1-V1-V9/B08-VL-GL6c | 1.20 | 100% | 7.69 | 100% |
| F20-VH-GL1-V1-V9-V14/B08-VL-GL6c | 1.91 | 100% | 11.11 | 100% |
| F20-VH-GL1-V4-V9/B08-VL-GL6c | 1.27 | 100% | 7.80 | 100% |
| F20-VH-GL1-V4-V9-V14/B08-VL-GL6c | 2.37 | 100% | 12.67 | 100% |

ND: not determined

Example 4: MMP Selectivity of Some Anti-MMP9 Antibodies According to the Invention in Human MMPs Catalytic Activity Assay The selectivity of anti-MMP9 antibodies was evaluated in an assay assessing MMPs mediated cleavage of a fluorogenic peptide substrate, OmniMMP™ RED (Enzo, BML-P277-9090), using the MMP Inhibitor Profiling Kit (Enzo, BML-AK308). Briefly, aliquots of recombinant catalytic domain of various human MMPs (MMP1, MMP2, MMP3, MMP8, MMP9, MMP12, MMP13, MMP14 and MMP19) were pre-incubated with a fixed concentration (100 nM) of test antibodies for one hour. The MMP inhibitor NNGH (Enzo, BML-PI115-9090) and anti-MMP2/9 (539A-M0237-D02, comparative antibody 3, that has an amino acid sequence of heavy chain of SEQ ID NO: 64 and of light chain SEQ ID NO: 65), anti-MMP9 (539A-M0240-B03, comparative antibody 2, that has an amino acid sequence of heavy chain of SEQ ID NO: 46 and of light chain SEQ ID NO: 47) and isotype control (anti-HEL IgG1) antibodies were included in the test, as positive and negative controls. Fluorogenic peptide substrate was then added and fluorescence was measured. Emitted fluorescence signal is proportional to the digestion of the peptidic substrate, thus to the activity of MMP catalytic domains. The fluorescence signal in the absence of inhibitor was normalized to 100% activity. Signal obtained in the presence of each inhibitor was given relative to this value and referred as to percentage of remaining activity.

Figure 7:
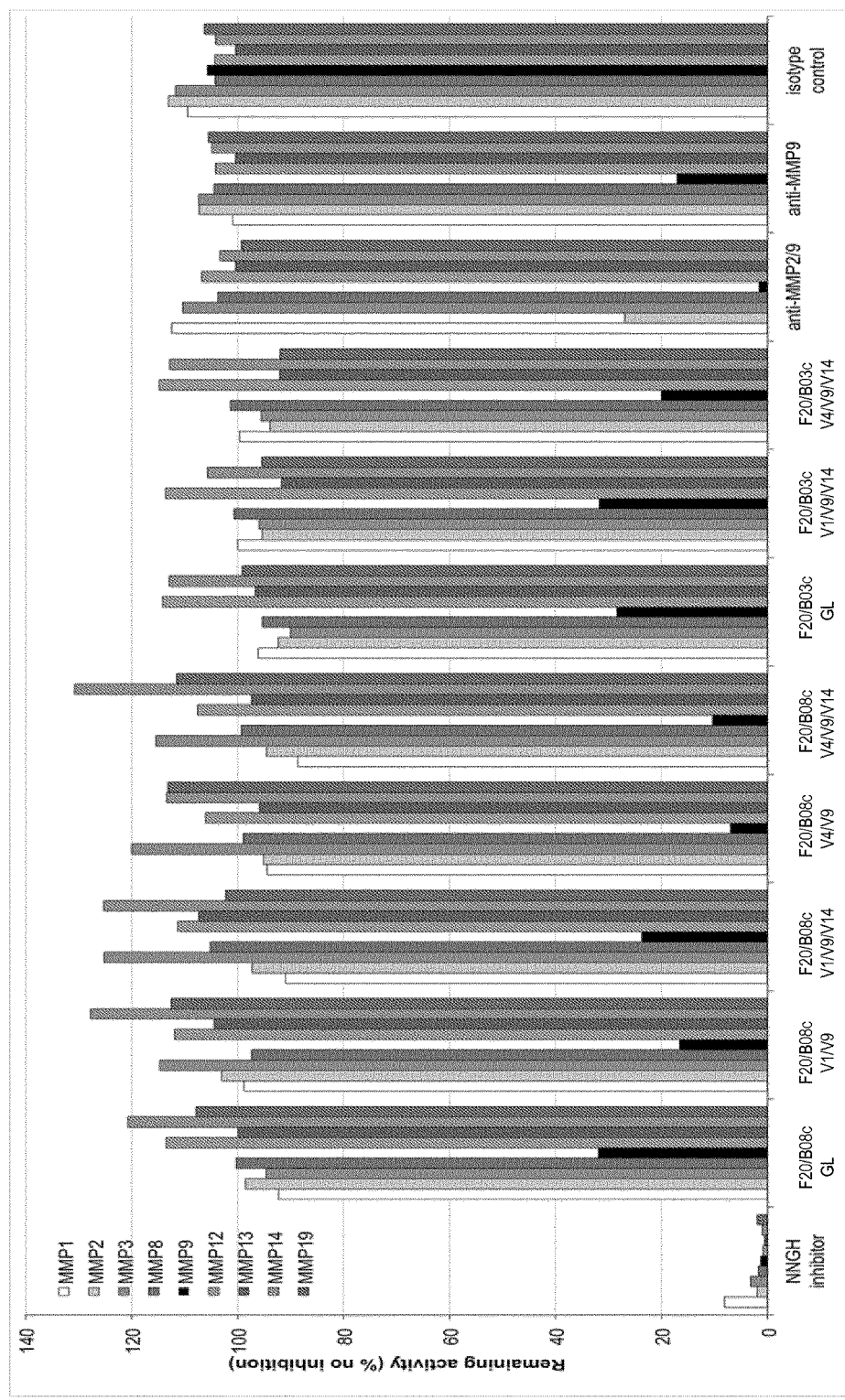
FIG. 7 shows neutralizing activity of exemplary anti-MMP9 antibodies according to the invention towards catalytic domains of various recombinant human matrix metalloproteinases.

All antibodies according to the invention, which were tested, were able to efficiently block the catalytic activity of human MMP9, while they had no significant effect on the catalytic activity of the eight other human MMPs tested (FIG. 7). All antibodies according to the invention also had no significant effect on the catalytic activity of human MMP7, MMP10, MMP16 and MMP17 (data not shown).

Example 5: Potency of Anti-MMP9 Antibody According to the Invention in Activity Assays Using Neutrophil-Secreted Natural Forms of Human MMP9

Several natural forms of human MMP9 have been described (monomeric MMP9, dimeric MMP9, and MMP9-bound to neutrophil gelatinase B-associated lipocalin NGAL (also called lipocalin-2) form, this later form being also named NGAL/MMP9 (Rudd et al., 1999, Biochemistry, 38, 13937-13950)) and shown to be associated with disease conditions.

Additional characterization of anti-MMP9 antibodies of the invention includes neutralization of neutrophil-derived natural forms of MMP9. To this aim, the functional neutralization of neutrophil-derived MMP9 catalytic activity towards the fluorogenic substrate OmniMMP™ RED (from ENZO) by antibodies according to the invention was evaluated.

Activation of the proMMP9 fraction in neutrophil-derived MMP9 preparations was performed by pre-treatment with APMA (p-aminophenyl mercuric acetate), which renders the MMP9 catalytic site accessible, before functional neutralization assay with F20-VH/B08-VLc anti-MMP9 antibody variant of the invention (F20-VH-GL1-V4-V9/B08-VL-GL6c). Briefly, aliquots of various APMA-activated neutrophil-derived human forms of proMMP9 (monomeric, dimeric and NGAL/MMP9) were incubated with the test antibody for one hour. The isotype control (anti-HEL IgG4) antibody was included in the test, as negative control.

Fluorogenic peptide substrate was then added and fluorescence was measured. Emitted fluorescence signal (Excitation at 540 nm, Emission at 590 nm) is proportional to the digestion of the peptidic substrate, thus to the activity of MMP catalytic domains.

Figure 8:
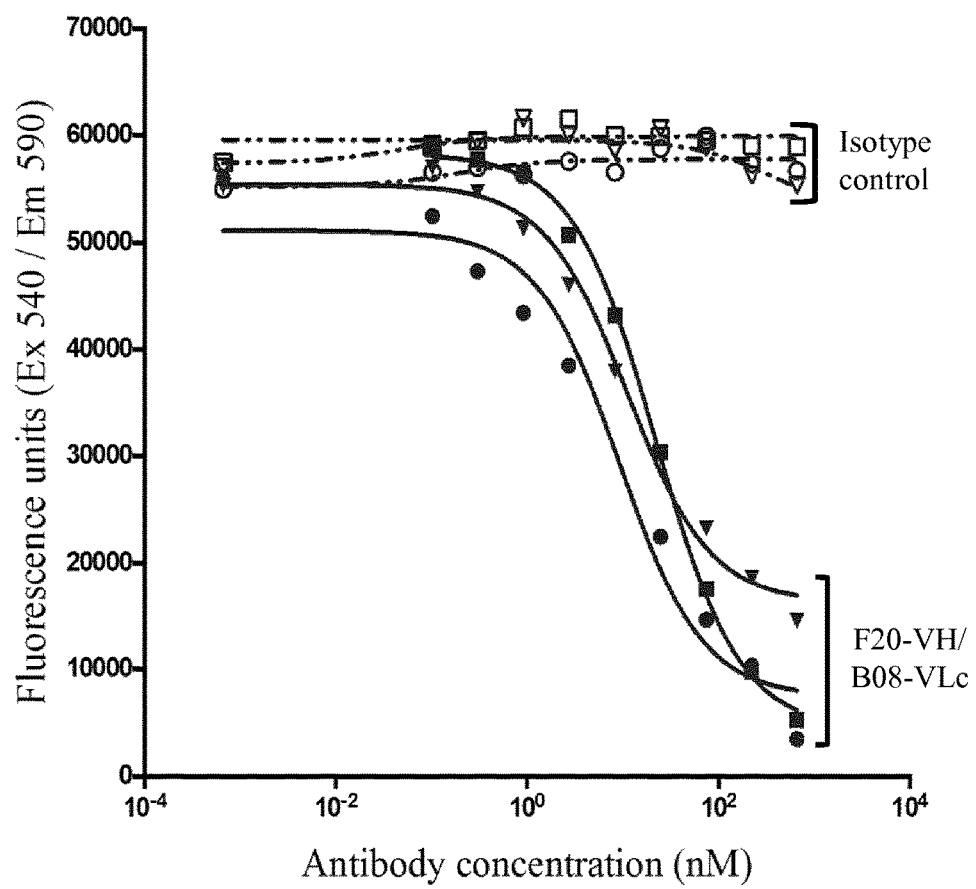
FIG. 8 shows titration of neutralizing activity of exemplary anti-MMP9 antibody according to the invention (F20-VH/B08-VLc variant; solid lines and closed symbols) or isotype control (dashed lines and open symbols) towards neutrophil-derived human dimeric MMP9 (circles), human monomeric MMP9 (triangles) and human NGAL-MMP9 complex (squares).

As shown in FIG. 8, F20-VH/B08-VLc antibody variant of the invention (F20-VH-GL1-V4-V9/B08-VL-GL6c) neutralizes activity of multiple physiological forms of human MMP9: monomeric MMP9, dimeric MMP9 and NGAL/MMP9 with 100% efficacy.

Figure 9:
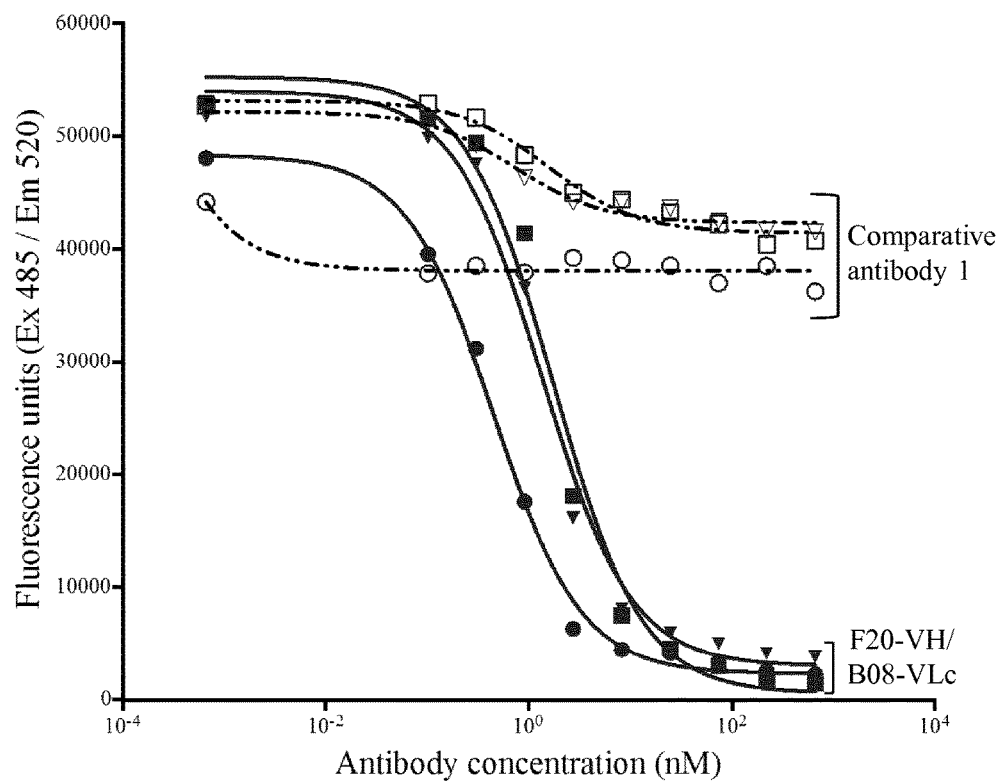
FIG. 9 shows titration of neutralizing activity of exemplary anti-MMP9 antibody according to the invention (F20-VH/B08-VLc variant; solid lines and closed symbols) or anti-MMP9 comparative antibody 1 (dashed lines and open symbols) towards MMP3-activated human monomeric MMP9 (triangles), dimeric MMP9 (circles) and NGAL-MMP9 complex (squares) derived from human neutrophils.

Antibody of the invention was compared to comparative antibody 1 using the "MMP3/MMP9 assay" described in the Example 2. F20-VH/B08-VLc antibody variant of the invention (F20-VH-GL1-V4-V9/B08-VL-GL6c) inhibits enzymatic activity of human neutrophil-derived MMP9 with 100% efficacy, whether it is as monomeric or dimeric form or bound to NGAL (FIG. 9), while comparative antibody 1 only shows partial inhibition (25% efficacy) on all forms of neutrophil-derived MMP9 (FIG. 9). Complete neutralization of all natural active forms of MMP9 by the antibody variant of the invention F20-VH/B08-VLc (F20-VH-GL1-V4-V9/B08-VL-GL6c) should translate into superior efficacy in patients with high serum levels of monomeric, dimeric MMP9 and/or NGAL/MMP9 complex.

Figure 10:
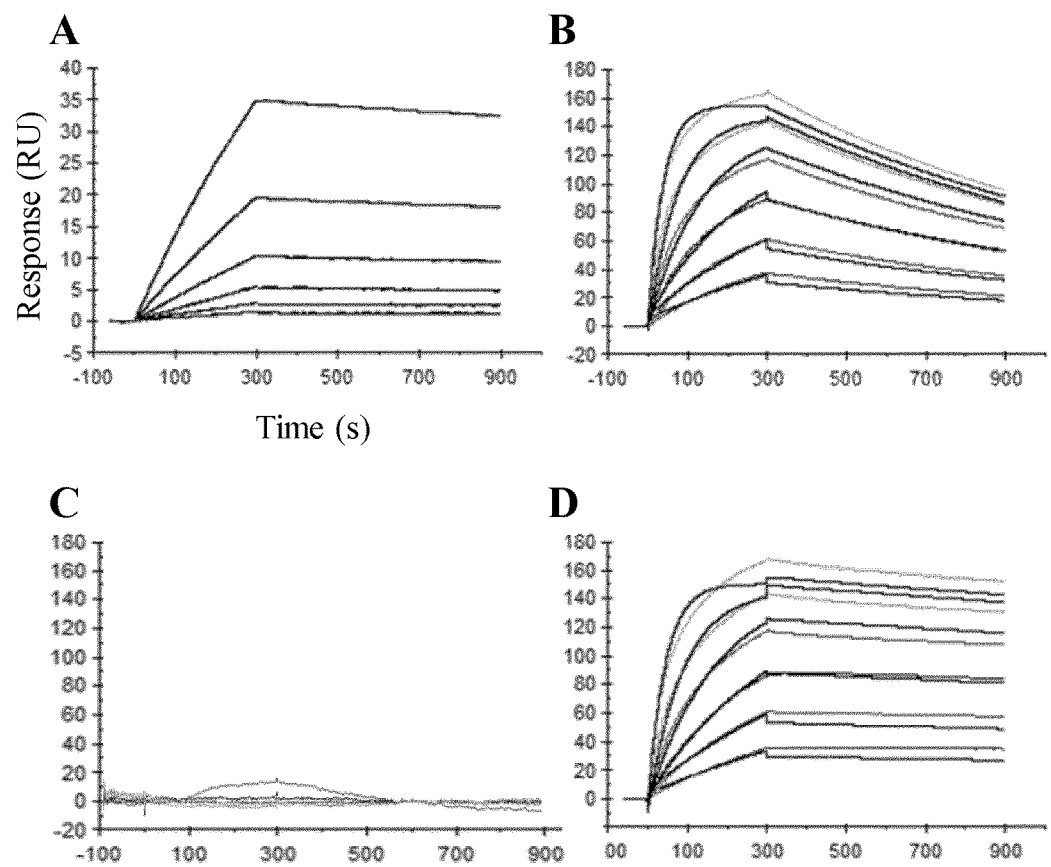
FIG. 10 shows kinetics of binding of anti-MMP9 antibodies to recombinant human MMP9 antigen. MMP3-activated MMP9 (panels A and B) and pro-MMP9 (panels C and D) were titrated on BIAcore sensor chip onto which anti-MMP9 antibodies, F20-VH/B08-VLc variant (panels A and C) and comparative antibody 1 (panels B and D), have been first immobilized. Sensorgrams of kinetics of binding are reported. Resonance unit (RU). All y axis-response (RU); all x axis-time (s).

Example 6: Binding Kinetics and Affinity for Pro- and Activated Forms of Human MMP9 of Anti-MMP9 Antibody According to the Invention Binding of anti-MMP9 antibodies towards recombinant human MMP9 antigen was characterized using standard Surface Plasmon Resonance (SPR) assay. In a first step, anti-MMP9 antibodies were captured by anti-human Fc antibody immobilized onto a BIAcore sensor chip. In a second step, pro-MMP9 or MMP3-activated MMP9 were titrated from 4.7 to 150 nM in 2-fold dilutions. Sensograms reveal that both F20-VH/B08-VLc variant (F20-VH-GL1-V4-V9/B08-VL-GL6c) and comparative antibody 1 bind well to MMP3-activated MMP9 (FIG. 10). Comparative antibody 1 also binds well to pro-MMP9, but minimal signal was observed with F20-VH/B08-VLc variant (F20-VH-GL1-V4-V9/B08-VL-GL6c) antibody (FIG. 10). Table 8 reports binding affinities ($K_D$) of F20-VH/B08-VLc antibody variant according to the invention (F20-VH-GL1-V4-V9/B08-VL-GL6c) and of comparative antibody 1 towards recombinant human pro-MMP9 and MMP3-activated MMP9. Since less then 1% binding was observed at a 150 nM antibody concentration, the $K_D$ of the F20-VH/B08-VLc antibody variant (F20-VH-GL1-V4-V9/B08-VL-GL6c) antibody for pro-MMP9 was estimated to be greater than 15 µM.

TABLE 8

| Antibody | Antigen | $K_D$ (nM) |
|---|---|---|
| F20-VH/ | Pro-MMP9 | >15,000 |
| B08-VLc | MMP9 | 11.7 |
| Comparative | Pro-MMP9 | 0.9 |
| antibody-1 | MMP9 | 5.0 |

$K_D$ - equilibrium dissociation constant, all calculated from the curves

Example 7: Epitope Mapping of Anti-MMP9 Antibody According to the Invention

Further characterization of anti-MMP9 antibodies of the invention included identification of regions of human MMP9, which are important for antibody binding and thereby define the epitopes. This characterization was carried out on one member of each of the F20/B08 and F20/B03 antibodies, namely F20-VH-GL1-V1-V9-V14/B03-VL-GL1c and F20-VH-GL1-V4-V9/B08-VL-GL6c.

The technology used to determine MMP9 epitopes capable of specific binding to anti-MMP9 antibodies of the invention applies chemical cross-linking and mass spectrometry (Peter and Tomer, 2001, *Anal. Chem.*, 73, 4012-4019; Pimenova et al, 2008, *J. Mass Spectrom. JMS*, 43, 185-195; Herzog et al., 2012, *Science* 337, 1348-1352). First, antibodies of the invention and pro-MMP9 were mixed in solution and submitted to chemical cross-linking using specially designed deuterated cross-linkers. Then, MMP9 and the covalently bound MMP9-antibody complex were submitted to proteolysis using 3 different proteolytic enzymes in order to generate a large number of overlapping peptides covering the entire sequence of MMP9. Peptides from MMP9 alone and from cross-linked MMP9-antibody complex were analyzed by high-resolution mass spectrometry (nLC-Orbitrap MS) and compared so as to determine the interacting peptides of the immuno-complex.

This analysis showed that the interaction interface between human MMP9 (SEQ ID NO 1) and antibodies of the invention is located within 3 discontinuous MMP9 epitopes which include the following MMP9 amino acid sequences:

SEQ ID NO: 41: $^{150}$AVTPLTFTRVYSRDADIVIQF$^{170}$ (corresponding to amino acid positions 150 to 170 of human MMP9) (herewith called region 1), SEQ ID NO: 42: $^{198}$IQGDAHFDDDELWSLGKGVVVP-TRFG$^{223}$ (corresponding to amino acid positions 198 to 223 of human MMP9) (herewith called region 2), and SEQ ID NO: 43: $^{419}$MYPMYRFTEGPPLHKDDVNGIR$^{440}$ (corresponding to amino acid positions 419 to 440 of human MMP9) (herewith called region 3).

Various recombinant mutants of human MMP9 were used to determine amino acids important for binding of comparative antibody 1 to MMP9 (mouse monoclonal AB0041, WO 2013/130078). The analysis identified residues E111, D113, R162 and I198 as important for binding of comparative antibody 1 to human MMP9. Two of these amino acids, R162 and I198, are present in epitope regions recognized by the anti-MMP9 antibodies of the invention (region 1 and region 2). However, region 3 defines a novel epitope region specifically important for anti-MMP9 antibodies of the invention. Region 3 is within the catalytic domain of MMP9. Because anti-MMP9 antibodies of the invention, unlike comparative antibody 1, are able to inhibit enzymatic activity of fully mature MMP9 while comparative antibody 1 does bind to fully mature MMP9, it is possible that binding to region 3 confers to the anti-MMP9 antibodies of the invention the capacity to neutralize the enzymatic activity of fully mature MMP9.

Further, the mouse monoclonal antibody REGA-3G12 (Martens et al., supra) was shown to bind to the peptide G171 to L187 of the human MMP9 using binding and competition assays. The region of MMP9 (G171-L187) bound by REGA-3G12 antibody is outside the 3 MMP9 regions recognized by the anti-MMP9 antibodies of the invention.

Example 8: Direct Binding and Competitive Binding of Anti-MMP9 Antibodies to Pro- and Activated Forms of Human MMP9

Figure 11:
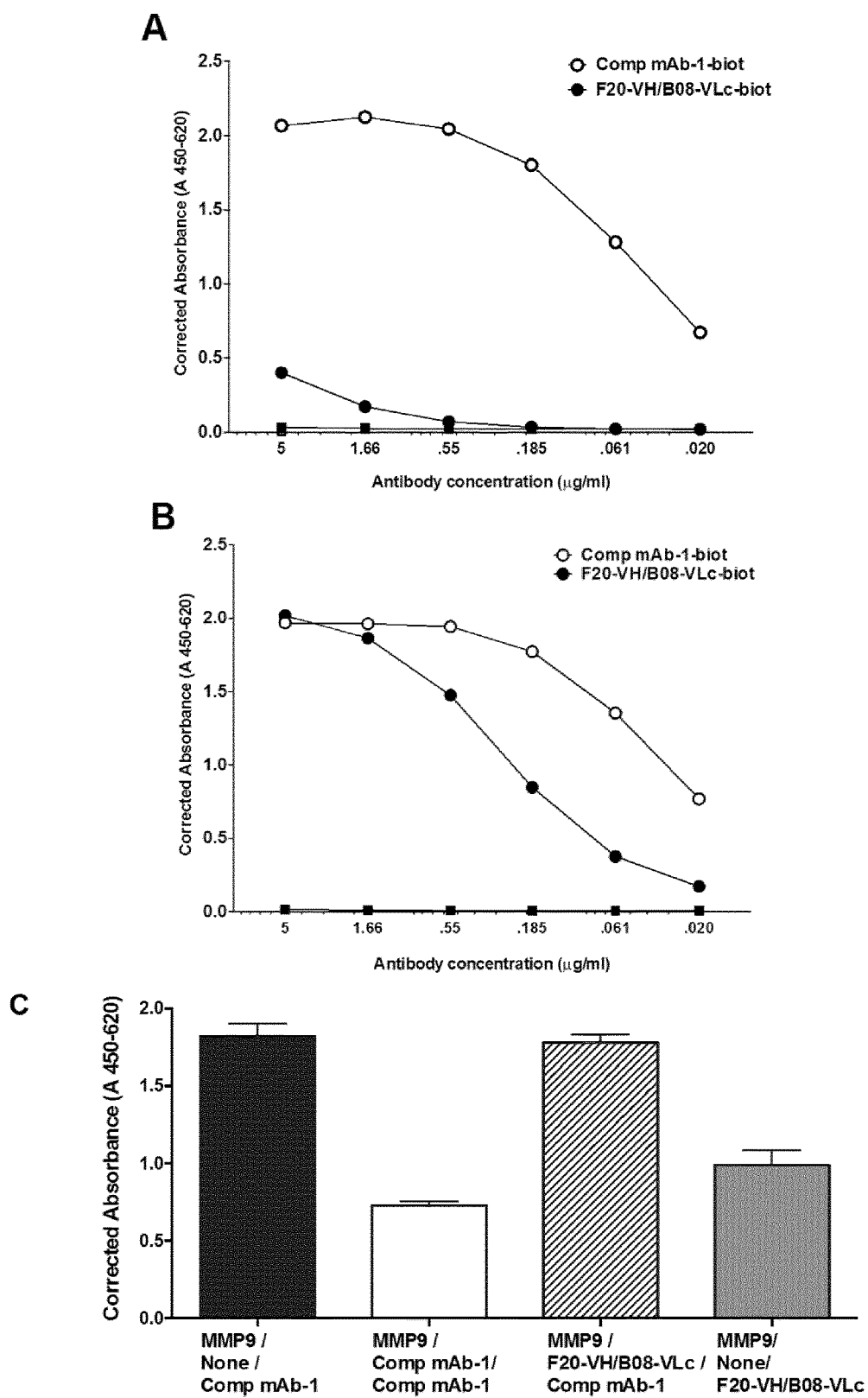
FIG. 11 shows direct and competitive binding of anti-MMP9 antibodies to human MMP9. Direct binding capacity of various concentrations of biotinylated anti-MMP9 antibodies F20-VH/B08-VLc variant (closed circles) and comparative antibody 1 (open circles) towards pro-MMP9 (panel A) or MMP3-activated MMP9 (panel B) was assessed using a standard ELISA protocol. MMP9 antigens were coated at 2.5 µg/ml. Controls were streptavidin-HRP alone (closed triangles), or human IgG4 isotype control plus biotinylated anti-human-IgG second step Fab antibody (closed squares). For competitive binding experiments (panel C), after a pre-incubation with buffer (none) or purified F20-VH/B08-VLc variant or comparative antibody 1 (both used at 50 µg/mL), coated MMP3-activated MMP9 was revealed using an optimal dose of biotinylated comparative antibody 1 (2.5 µg/mL) or F20-VH/B08-VLc variant (50 µg/mL). For panels A, B, C, results are expressed as mean±SD of corrected absorbance (A450-A620) for each condition performed in duplicate.

Direct binding capacities of anti-MMP9 antibodies towards human pro-MMP9 and MMP3-activated human MMP9, respectively, were assessed using a standard ELISA protocol. Briefly, 96-well plates were coated with (2.5 µg/ml) of either form of MMP9 for 16 h at room temperature. Following 2 h incubation with blocking buffer (2% goat serum in PBS/Tween) and four washes with wash buffer (PBS/Tween 0.05% v/v), various concentrations of biotinylated anti-MMP9 antibodies (comparative antibody 1 or F20-VH/B08-VLc variant (F20-VH-GL1-V4-V9/B08-VL-GL6c) were added in duplicate and incubated for 1 h. Wells were then washed four times and bound biotinylated antibodies were revealed using HRP-coupled Streptavidin and TMB substrate. Absorbance was read at 450 nm and 620 nm for each duplicate and data were expressed as corrected absorbance (A450-A620). Results shown in FIG. 11 indicate that both comparative antibody 1 and F20-VH/B08-VLc variant (F20-VH-GL1-V4-V9/B08-VL-GL6c) anti-MMP9 antibodies strongly bind to MMP3-activated MMP9 (FIG. 11B), in a dose-dependent manner. On the contrary, while comparative antibody 1 binds well to pro-MMP9, in a dose-dependent manner (FIG. 11A), the F20-VH/B08-VLc variant (F20-VH-GL1-V4-V9/B08-VL-GL6c) anti-MMP9 antibody only shows significant binding to pro-MMP9 at the highest concentration tested (5 µg/mL) (FIG. 11A).

To test whether F20-VH/B08-VLc variant (F20-VH-GL1-V4-V9/B08-VL-GL6c) antibody would compete with comparative antibody 1 for binding to MMP9, the same ELISA assay was used with coating of MMP3-activated MMP9 but purified antibodies F20-VH/B08-VLc variant or comparative antibody 1 were added for 2 hours prior to the addition of biotinylated anti-MMP9 antibodies. Following four washes with wash buffer, a predefined optimal dose of biotinylated comparative antibody 1 or F20-VH/B08-VLc was added and incubated for 1 h. Results shown in FIG. 11 panel C, indicate that addition of the F20-VH/B08-VLc variant (F20-VH-GL1-V4-V9/B08-VL-GL6c) anti-MMP9 antibody does not prevent binding of comparative antibody 1 to MMP9, while the same concentration of purified comparative antibody 1 fully prevents further binding of biotinylated comparative antibody 1 to MMP9.

Taken together, these binding experiments show that, unlike comparative antibody 1, the F20-VH/B08-VLc variant (F20-VH-GL1-V4-V9/B08-VL-GL6c) anti-MMP9 antibody preferentially binds to the active form of MMP9 versus pro-MMP9, and that it does not compete with comparative antibody 1 for binding to MMP9.

Example 9: Effect of Anti-MMP9 Antibody According to the Invention in Cancer Cell Invasion Assay Cancer cell line invasion was assessed using Matrigel-coated transwells. Insert membranes of transwells (provided in kit from Cultrex—3455-024) were coated with basement membrane extract (BME ×0.5; provided in Cultrex's kit) and incubated for 24 h at 37° C. Meanwhile, MGC803 (human gastric cancer cell line—Easy-Bio, China) were starved in RPMI culture medium (Gibco—52400025) deprived of serum (starving medium). Cells were then recovered and resuspended at $0.5 \times 10^6$ cells/ml in starving medium containing 100 ng/ml PMA (Phorbol 12-Myristate 13-Acetate from Sigma—P8139) and either 25 µM MMP inhibitor (GM-6001 from Millipore—CC1000), 10 µg/ml anti-MMP9 antibody (F20-VH/B08-VLc variant F20-VH-GL1-V4-V9/B08-VL-GL6c), 10 µg/ml anti-IgG4 antibody (isotype control) or none (medium). One hundred µl of treated cells were seeded into Matrigel-coated transwells and 500 µl of RPMI medium containing 10% FCS were added in the lower side of the transwell. Plates were incubated for 16 h at 37° C. Invading cells were quantified by incubation of the bottom side of transwell membrane with Calcein-AM, whose cleavage into fluorescent Calcein is proportional to cell counts. Emitted fluorescent signal (Excitation at 485 nm, emission at 520 nm) reflects efficiency of cell invasion through Matrigel.

Figure 12:
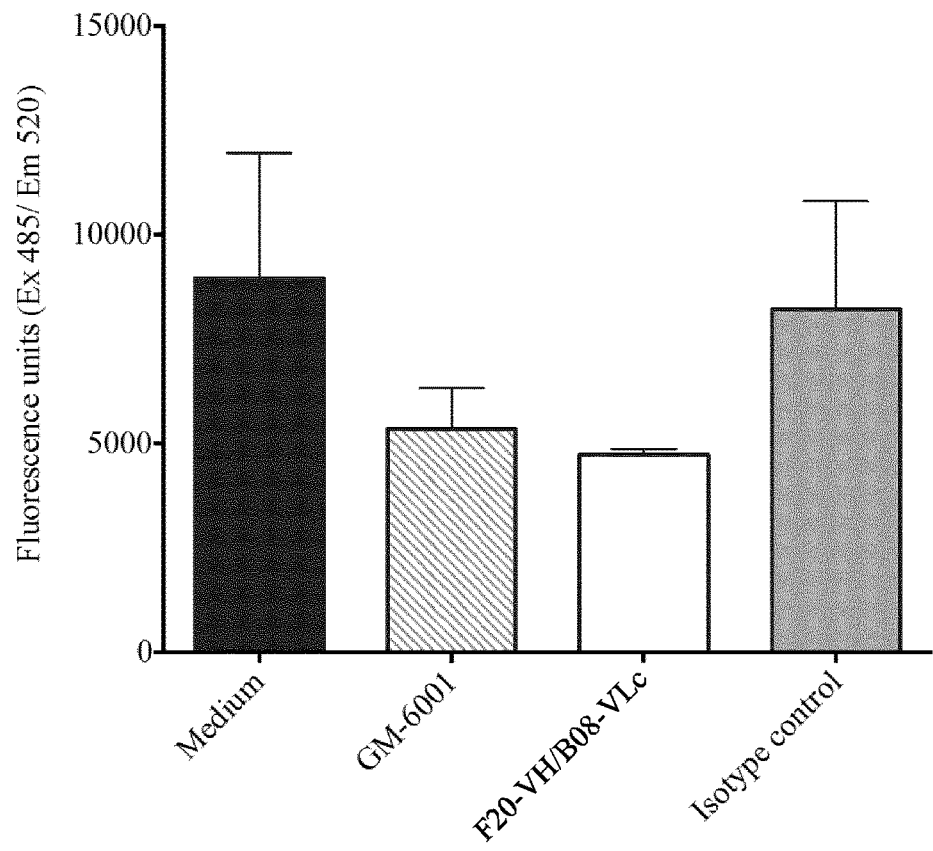
FIG. 12 shows the effect of anti-MMP9 antibody (F20-VH/B08-VLc variant) on cancer cell line invasion through Matrigel-coated transwell. MGC803 human gastric cancer cells were incubated with Phorbol 12-Myristate 13-Acetate (PMA) and with a broad chemical inhibitor of MMPs (GM-6001), anti-MMP9 antibody (F20-VH/B08-VLc), isotype control or medium alone. Invading cells were quantified after 16 hours using Calcein-AM. Each condition was performed in duplicates and means and SD of fluorescence units are reported.

The results show that anti-MMP-9 antibody F20-VH/B08-VLc variant (F20-VH-GL1-V4-V9/B08-VL-GL6c) efficiently inhibits migration of MGC803 cancer cells through Matrigel with similar efficacy when compared to MMP inhibitor GM-6001 (FIG. 12). As metastatic cells escape from their site of origin by invading surrounding tissue, including basement membranes, this result indicates that anti-MMP9 of the invention might be an effective anti-migratory and anti-invasive drug for metastatic cancers.

Example 10: Activity of Anti-MMP9 Antibody According to the Invention in a Mouse Model of Colitis The dextran sodium sulphate (DSS)-induced colitis mouse model of inflammatory bowel disease (IBD) is widely used model in preclinical studies. Drugs that are approved for treatment of ulcerative colitis, such as steroids, metronidazole, 5'-aminocalicylates, cyclosporine, and anti-TNFα immunotherapy have demonstrated efficacy in reducing disease severity in the DSS model showing that this model is a relevant model for the translation of mouse data to human disease (Perse et al., 2012, *J. Biomed. Biotechnol.*, 2012:718617). Mouse colitis is induced by addition of DSS to drinking water resulting in damage to the colonic mucosa. Clinical manifestation of DSS colitis in acute phase may include weight loss and diarrhea. Typical histological changes of acute DSS-colitis are similar to what observed in human IBD and include mucin depletion, epithelial degeneration, and necrosis leading to disappearance of epithelial cells. The latter is accompanied by neutrophils infiltration within the lamina propria and submucosa, cryptitis, crypt abscesses, and inflammation of the colonic mucosa and submucosa.

The therapeutic efficacy of an anti-MMP9 antibody according to the invention was assessed in a DSS-induced colitis model in BALB/c mice. Colitis was induced with 4% (w/v) DSS in drinking water for 5 days. Doses of 30 mg/kg F20-VH/B08-VLc (variant F20-VH-GL1-V4-V9/B08-VL-GL6c) or isotype control (IgG4) antibodies were intraperitoneally injected to groups of 10 mice at day 6, 9 and 12, and animals were sacrificed at day 14.

Figure 13:
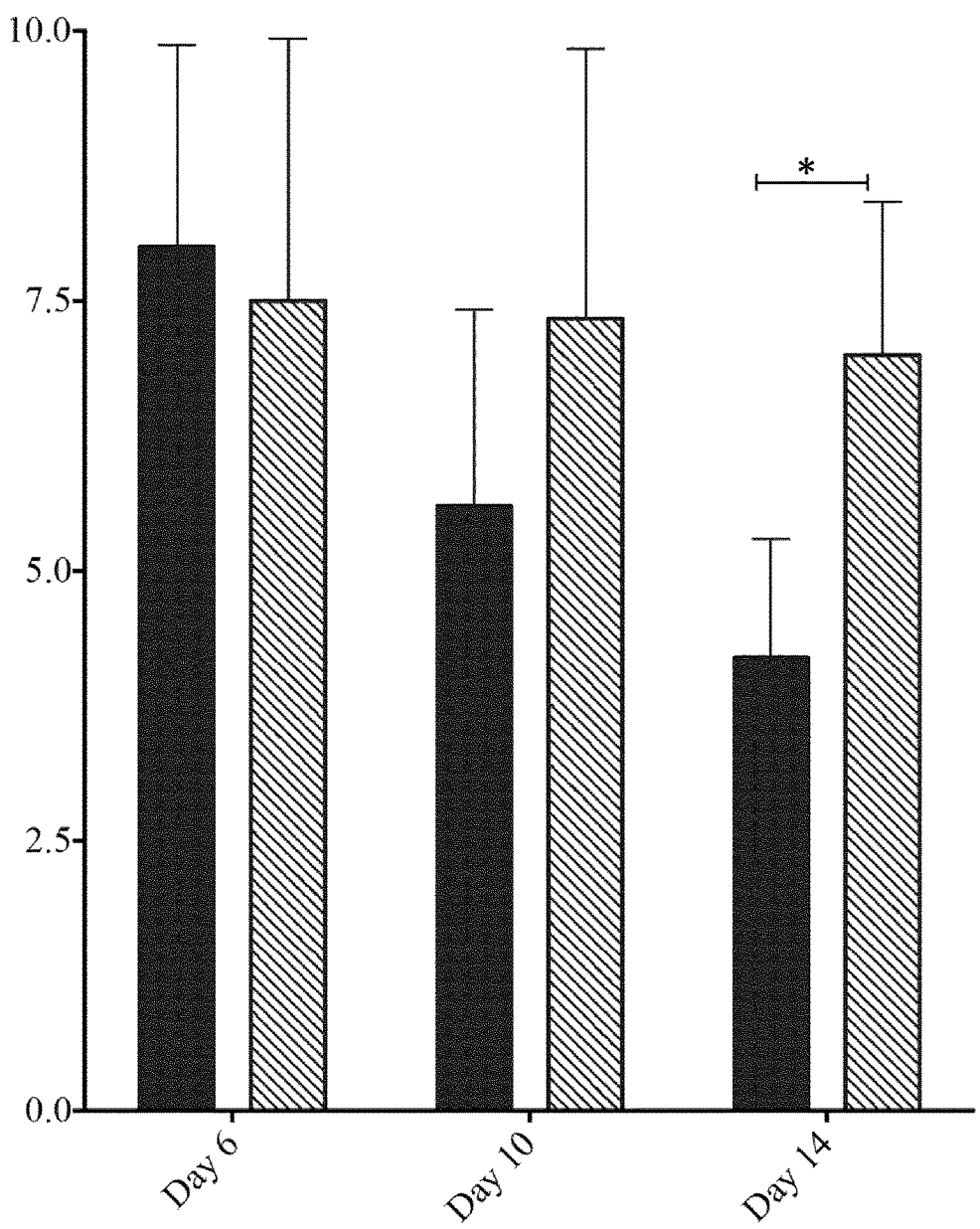
FIG. 13 shows endoscopic scores in a DSS-induced mouse colitis model. At day 6 after DSS induction, mice were treated by anti-MMP9 antibody (F20-VH/B08-VLc variant) or by isotype control antibody. Effects of F20-VH/B08-VLc variant are shown as black bars, isotype control shown as hatched bars. Means and SD of endoscopic scores are reported for both groups of treated mice (n=5 for F20-VH/B08-VLc; n=6 for isotype control); Statistical comparisons of group data (F20-VH/B08-VLc versus isotype control at day 14 after DSS induction) were performed using two-way, unpaired T test, using Graph Pad Prism. *p=0.005.

The course of the disease was evaluated in blind fashion by video endoscopy of the lower colon at days 6, 10 and 14. Colitis was scored visually on a scale of 0-14 based on the degree of ulceration, vascularisation, and granularity present in tissue and colon length involved as follows: ulceration (0, 1, 2 or 3), masking of vascularisation (0, 1, 2 or 3), granularity (0, 1, 2 or 3), erythema (0, 1, 2 or 3), length involved (0, 1: localized, 2: diffuse). Each mouse was assigned a single endoscopy score corresponding to the damage observed throughout the entire length of the colon examined. Animals that had an endoscopic score <5 at Day 6, prior starting antibody treatment, were not considered to have sufficient disease severity and were excluded from further analysis. As shown in FIG. 13, at Day 6, both groups had similar mean endoscopy score while at study termination Day 14, F20-VH/B08-VLc-treated animals showed a significant improvement (p=0.005) in mean endoscopy score in comparison to the isotype control antibody-treated group.

Figure 14:
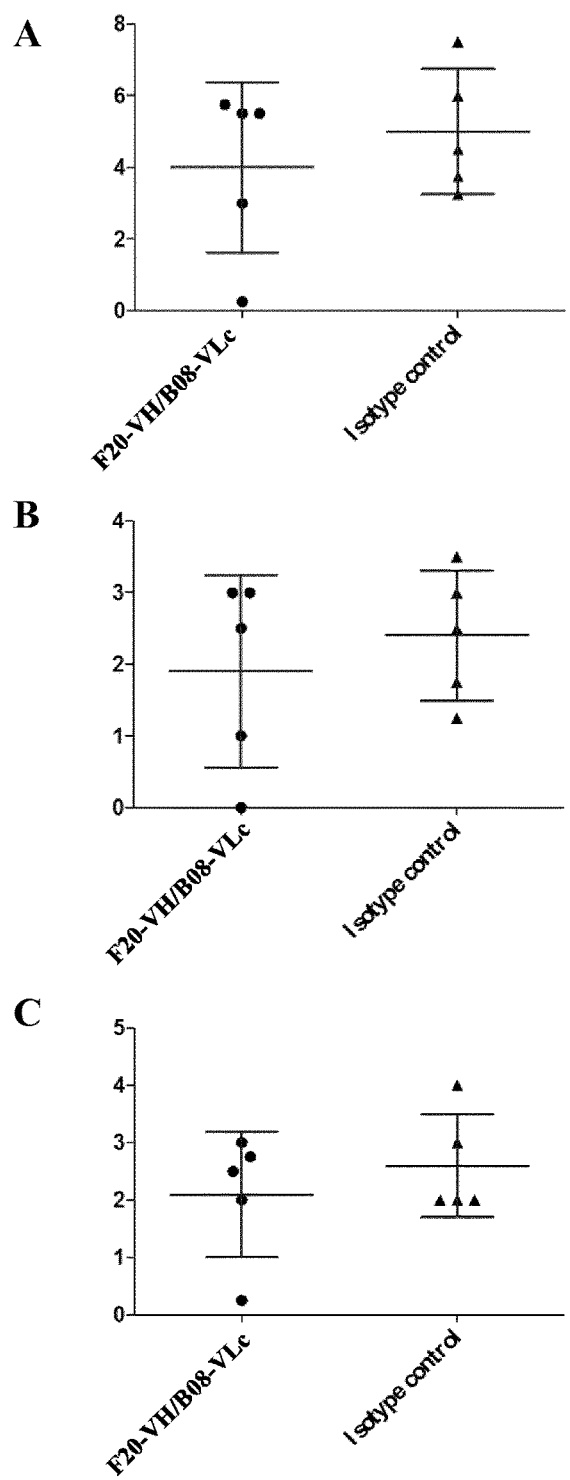
FIG. 14 shows total histology scores, infiltrate and epithelial damage scores of colon sections from mice with DSS-induced colitis treated with anti-MMP9 antibody (F20-VH/B08-VLc variant) or isotype control antibody. (A) total histology score, (B) infiltrate (C) epithelial damage. Individual values, means and SD for each criterion are reported for both groups of treated mice (n=5 for F20-VH/B08-VLc; n=5 for isotype control).

At study termination (Day 14), distal colon was excised from each mouse, formalin-fixed and embedded in paraffin and sectioned for histology. All sections were stained with haematoxylin and eosin and examined in a fashion blind as to treatment groups. Tissues were scored for epithelium damage and infiltration of inflammatory cells according to the scoring scale of 1-4 for each parameter. The histology score represents the sum of the epithelium damage and infiltration of inflammatory cell scores, and thus ranges from 0 to 8. The results are shown in FIG. 14.

DSS-treated mice developed a colitis characterised by epithelial hyperplasia and goblet cell depletion, infiltration of inflammatory cells into the mucosa and sub-mucosa. Crypt abscesses and mucosal erosion and ulceration were also observed in some colon cross-sections. As shown in FIG. 13, analysis of histological scores showed that treatment with anti-MMP9 antibody was associated with a decrease in mean colitis severity score in F20-VH/B08-VLc compared to isotype antibody treated-control group. Similarly, mean scores for infiltration of inflammatory cells and epithelial damage were also decreased by the anti-MMP9 antibody treatment when compared to isotype antibody-treated control group.

Example 11: Activity of an Anti-MMP9 Antibody According to the Invention in a Heterotopic Transplant Mouse Model of Intestinal Fibrosis Severe mucosal tissue damage is a main feature of inflammatory bowel disease (IBD). Tissue injury is a trigger for repair activities by the surrounding cells. Rapid wound closure is important to reduce the time during which the barrier function of the intestinal wall is impaired, but excessive tissue repair promotes fibrosis, a common occurrence in Crohn's disease (CD). Fibrosis is leading to stricture formation in 10-40% of patients (Cosnes et al., 2002, *Inflamm. Bowel Dis.*, 8(4): 244-50; Freeman, 2003, *J. Clin. Gastroenerol.*, 37(3): 216-9), an indication for surgery in approximately 80% of strictured patients (Cosnes et al., 2002, supra).

The heterotopic transplantation of intestinal resections in mice leads to the disappearance of intestinal epithelium and culminate in the fibrotic occlusion of the intestinal lumen, recapitulating histologic and molecular features of human intestinal fibrosis, such as luminal wall thickening, exaggerated collagen deposition, and expression of profibrotic mediators.

Donor (green fluorescent protein-marked C57BL/6-Tg UBC-GFP mice) small bowel resections were transplanted subcutaneously into the neck of recipient C57BL/6 mice. Mice were injected intraperitoneally at day 5, 8 and 10 with 30 mg/kg of an anti-MMP9 antibody of the invention (F20-VH/B08-VLc, variant F20-VH-GL1-V4-V9/B08-VL-GL6c), or isotype control antibody (IgG4), 5 mice per group. Small bowel grafts were explanted 14 days after transplantation. After explant, each graft was divided into three equal segments. The central segment was fixed in 4% formalin, and prepared for histopathological assessment. The two outer segments were snap frozen in liquid nitrogen and stored at −70° C. until RNA or protein extraction.

Histologic cross sections were stained with Sirius red to highlight collagen (red stain). Collagen layer thickness was determined by an independent investigator blinded to the type of experiment. Microscopic assessment was done using an AxioCam MRc5 on a Zeiss Axiophot microscope. The thickness of the collagen layer was measured with the AxioVision Release 4.7.2 software (Zeiss). Thickness was calculated from eight places in representative areas (in eight samples investigated for each time point) at 100-fold magnification. Statistical analyses were performed using PRISM 6 software. Unpaired t test was used for comparison among groups.

Figure 15:
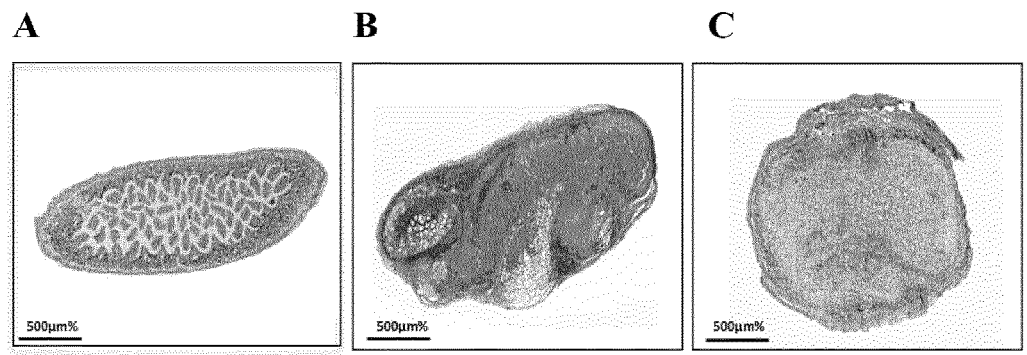
FIG. 15 shows representative cross-sections of mouse intestinal explanted grafts stained with hematoxylin-eosin. (A) Day 0—Freshly isolated small bowel resection with open lumen and typical crypt structures. (B) Isotype control day 14—complete occlusion of the intestinal lumen 14 days after transplantation in the isotype control-treated mice (n=5). (C) F20-VH/B08-VLc variant day 14—partial occlusion of the intestinal lumen 14 days after transplantation in the anti-MMP9-treated mice (n=5).

Compared with control isotype, anti-MMP9 treatment with F20-VH/B08-VLc significantly protects against loss of epithelial structure in heterotopic intestinal grafts as shown in FIG. 15 and significantly (p<0.0001) reduces collagen layer thickness in heterotopic intestinal grafts, as show on FIG. 16. This result indicates that anti-MMP9 antibody of the invention might effectively fibrotic diseases and fistulizing Crohn's disease.

Example 12: Effect of Anti-MMP9 Antibody in Swiss Nude Mice Bearing Subcutaneous HCT-116 Human Colon Tumor Cells Human colon cancer cell line HCT-116 ($1 \times 10^7$ cells) are injected subcutaneously into the right flank of nude mice and allowed to grow to ≈100 mm³ prior to treatment initiation. Anti-MMP9 antibody of the invention F20-VH/B08-VLc, variant F20-VH-GL1-V4-V9/B08-VL-GL6c or isotype control antibody IgG4 are injected intraperitoneally for 3 weeks. Mice receive a loading dose of antibodies at 50 mg/kg on the first day of treatment and are thereafter dosed twice per week at 30 mg/kg. Mice are sacrificed at day 21-post treatment initiation and primary tumor and organs with metastasis are collected for analysis. Weight and size of primary tumor are measured and the number of visually metastatic foci in lymph nodes, liver, lung and peritoneum counted.

LIST OF SEQUENCES

Amino acid sequence of Human MMP9 (NCBI Reference Sequence: NP_004985.2)
SEQ ID NO: 1

```
mslwqplvlv llvlgccfaa prqrqstlvl fpgdlrtnlt drqlaeeyly rygytrvaem
rgeskslgpa lllqkqlsl petgeldsat lkamrtprcg vpdlgrfqtf egdlkwhhhn
itywiqnyse dlpravidda farafalwsa vtpltftrvy srdadiviqf gvaehgdgyp
fdgkdgllah afppgpgiqg dahfdddelw slgkgvvvpt rfgnadgaac hfpfifegrs
ysacttdgrs dglpwcstta nydtddrfgf cpserlytqd gnadgkpcqf pfifqgqsys
acttdgrsdg yrwcattany drdklfgfcp tradstvmgg nsagelcvfp ftflgkeyst
ctsegrgdgr lwcattsnfd sdkkwgfcpd qgyslflvaa hefghalgld hssvpealmy
pmyrftegpp lhkddvngir hlygprpepe prpptttpq ptapptvcpt gpptvhpser
ptagptgpps agptgpptag pstattvpls pvddacnvni fdaiaeignq lylfkdgkyw
rfsegrgsrp qgpfliadkw palprkldsv feerlskklf ffsgrqvwvy tgasvlgprr
ldklglgadv aqvtgalrsg rgkmllfsgr rlwrfdvkaq mvdprsasev drmfpgvpld
thdvfqyrek ayfcqdrfyw rvssrselnq vdqvgyvtyd ilqcped
```

LIST OF SEQUENCES

Amino acid sequence of heavy chain F20-VH-CDR1
SEQ ID NO: 2: DYPMH

Amino acid sequence of heavy chain F20-VH-CDR2
SEQ ID NO: 3: GISSNSGSVGYADSVKG

Aminoacid sequence of heavy chain F20-VH-CDR3
SEQ ID NO: 4: DKIYYGSGSYDFYYYGMDV

Amino acid sequence of heavy chain F20-VH-CDR2-V1
SEQ ID NO: 5: GISSQSGSVGYADSVKG Amino acid sequence of heavy chain F20-VH-CDR2-V4
SEQ ID NO: 6: GISSRSGSVGYADSVKG Amino acid sequence of heavy chain F20-VH-CDR2-V9
SEQ ID NO: 7: GISSNSGSVGYAESVKG Amino acid sequence of heavy chain F20-VH-CDR2-V1-V9
SEQ ID NO: 8: GISSQSGSVGYAESVKG Amino acid sequence of heavy chain F20-VH-CDR2-V4-V9
SEQ ID NO: 9: GISSRSGSVGYAESVKG Amino acid sequence of heavy chain F20-VH-CDR3-V14
SEQ ID NO: 10: DKIYYGSGSYDFYYYGIDV Amino acid sequence of heavy chain F20-VH
SEQ ID NO: 11:
EVQLVESGGGLVQPGRSLRLSCAASGFTFN<u>DYPMH</u>WVRQAPGKGLEWVS<u>GISSNSGSV
GYADSVKG</u>RFTISRDNAKNSLYLQMNSLRDEDTAVYYCAR<u>DKIYYGSGSYDFYYYGM
DV</u>WGQGTTVTVSS Amino acid sequence of F20-VH-GL1
SEQ ID NO: 12:
EVQLVESGGGLVQPGRSLRLSCAASGFTFN<u>DYPMH</u>WVRQAPGKGLEWVS<u>GISSNSGSV
GYADSVKG</u>RFTISRDNAKNSLYLQMNSLRAEDTALYYCAR<u>DKIYYGSGSYDFYYYGM
DV</u>WGQGTTVTVSS Amino acid sequence of heavy chain F20-VH-GL1-V1
SEQ ID NO: 13:
EVQLVESGGGLVQPGRSLRLSCAASGFTFN<u>DYPMH</u>WVRQAPGKGLEWVS<u>GISSQSGSV
GYADSVKG</u>RFTISRDNAKNSLYLQMNSLRAEDTALYYCAR<u>DKIYYGSGSYDFYYYGM
DV</u>WGQGTTVTVSS Amino acid sequence of heavy chain F20-VH-GL1-V4
SEQ ID NO: 14:
EVQLVESGGGLVQPGRSLRLSCAASGFTFN<u>DYPMH</u>WVRQAPGKGLEWVS<u>GISSRSGSV
GYADSVKG</u>RFTISRDNAKNSLYLQMNSLRAEDTALYYCAR<u>DKIYYGSGSYDFYYYGM
DV</u>WGQGTTVTVSS Amino acid sequence of heavy chain F20-VH-GL1-V9
SEQ ID NO: 15:
EVQLVESGGGLVQPGRSLRLSCAASGFTFN<u>DYPMH</u>WVRQAPGKGLEWVS<u>GISSNSGSV
GYAESVKG</u>RFTISRDNAKNSLYLQMNSLRAEDTALYYCAR<u>DKIYYGSGSYDFYYYGM
DV</u>WGQGTTVTVSS Amino acid sequence of heavy chain F20-VH-GL1-V14
SEQ ID NO: 16:
EVQLVESGGGLVQPGRSLRLSCAASGFTFN<u>DYPMH</u>WVRQAPGKGLEWVS<u>GISSNSGSV
GYADSVKG</u>RFTISRDNAKNSLYLQMNSLRAEDTALYYCAR<u>DKIYYGSGSYDFYYYGI
DV</u>WGQGTTVTVSS Amino acid sequence of heavy chain F20-VH-GL1-V1-V9
SEQ ID NO: 17:
EVQLVESGGGLVQPGRSLRLSCAASGFTFN<u>DYPMH</u>WVRQAPGKGLEWVS<u>GISSQSGSV
GYAESVKG</u>RFTISRDNAKNSLYLQMNSLRAEDTALYYCAR<u>DKIYYGSGSYDFYYYGM
DV</u>WGQGTTVTVSS Amino acid sequence of heavy chain F20-VH-GL1-V1-V9-V14
SEQ ID NO: 18:
EVQLVESGGGLVQPGRSLRLSCAASGFTFN<u>DYPMH</u>WVRQAPGKGLEWVS<u>GISSQSGSV
GYAESVKG</u>RFTISRDNAKNSLYLQMNSLRAEDTALYYCAR<u>DKIYYGSGSYDFYYYGI
DV</u>WGQGTTVTVSS

LIST OF SEQUENCES

Amino acid sequence of heavy chain F20-VH-GL1-V4-V9
SEQ ID NO: 19:
EVQLVESGGGLVQPGRSLRLSCAASGFTFNDYPMHWVRQAPGKGLEWVSGISSRSGSV
GYAESVKGRFTISRDNAKNSLYLQMNSLRAEDTALYYCARDKIYYGSGSYDFYYYGM
DVWGQGTTVTVSS Amino acid sequence of heavy chain F20-VH-GL1-V4-V9-V14
SEQ ID NO: 20:
EVQLVESGGGLVQPGRSLRLSCAASGFTFNDYPMHWVRQAPGKGLEWVSGISSRSGSV
GYAESVKGRFTISRDNAKNSLYLQMNSLRAEDTALYYCARDKIYYGSGSYDFYYYGI
DVWGQGTTVTVSS Amino acid sequence of light chain B03-VL-CDR+.
SEQ ID NO: 21: QGDSLRSYYAS Amino acid sequence of light chain B03-VL-CDR2
SEQ ID NO: 22: GKNNRPS Amino acid sequence of light chain B03-VL-CDR3
SEQ ID NO: 23: QSRDNIGNHRVVL Amino acid sequence of light chain B03-VL
SEQ ID NO: 24:
SSELTQDPAVSVALGQTVRITCQGDSLRSYYASWYQQKPGQAPVVVIYGKNNRPSGIP
DRFSGSSSGNTVSLTITGAQAEDEADYYCQSRDNIGNHRVVLFGGGTKVTVLG Amino acid sequence of light chain B03-VL-GL1
SEQ ID NO: 25:
SSELTQDPAVSVALGQTVRITCQGDSLRSYYASWYQQKPGQAPVVVIYGKNNRPSGIP
DRFSGSSSGNTVSLTITGAQAEDEADYYCQSRDNIGNHRVVLFGGGTKLTVLG Amino acid sequence of light chain B08-VL-CDR1
SEQ ID NO: 26: TGTSNDVGAYNRVS Amino acid sequence of light chain B08-VL-CDR2
SEQ ID NO: 27: GVSNRPS Amino acid sequence of light chain B08-VL-CDR3
SEQ ID NO: 28: TSYSSSTTSYVV Amino acid sequence of light chain B08-VL
SEQ ID NO: 29:
QSALTQPRSVSGSPGQSVTISCTGTSNDVGAYNRVSWYQQHPGKAPKLLIYGVSNRPS
GVSTRFSGSKSGNTASLTISGLLAADEADFYCTSYSSSTTSYVVFGGGTKVTVLG Amino acid sequence of light chain B08-VL-GL6
SEQ ID NO: 30:
QSALTQPASVSGSPGQSITISCTGTSNDVGAYNRVSWYQQHPGKAPKLMIYGVSNRPS
GVSNRFSGSKSGNTASLTISGLQAEDEADFYCTSYSSSTTSYVVFGGGTKVTVLG Nucleic acid sequence of heavy chain F20-VH-CDR1
SEQ ID NO: 31: gactacccatgcac Nucleic acid sequence of heavy chain F20-VH-CDR2
SEQ ID NO: 32:
ggcatctcctccaactccggctccgtgggctacgccgactccgtgaagggc Nucleic acid sequence of heavy chain F20-VH-CDR3
SEQ ID NO: 33:
gacaagatctactacggctccggctcctacgacttctactactactacggcatggacg
tg Nucleic acid sequence of light chain B03-VL-CDR1
SEQ ID NO: 34: caaggcgattctctgcgctcatattatgcttct Nucleic acid sequence of light chain B03-VL-CDR2
SEQ ID NO: 35: ggaaaaaacaaccgaccatct Nucleic acid sequence of light chain B03-VL-CDR3
SEQ ID NO: 36: caatctcgagacaatatagggaaccatagagttgttctg Nucleic acid sequence of light chain B08-VL-CDR1
SEQ ID NO: 37: acaggaacgtctaatgatgtgggggcttacaatcgcgtcagt Nucleic acid sequence of light chain B08-VL-CDR2
SEQ ID NO: 38: ggcgtgtctaacaggcctagc

LIST OF SEQUENCES

Nucleic acid sequence of light chain B08-VL-CDR3
SEQ ID NO: 39: acaagctacagtagcagtaccacatcatatgtcgtc Amino acid sequence of engineered human IgG4 heavy chain constant region
SEQ ID NO: 40:
ASTKGPSVFPLAPCSRSTSESTAALGCLVKDYFPEPVTVSWNSGALTSGVHTFPAVLQ
SSGLYSLSSVVTVPSSSLGTKTYTCNVDHKPSNTKVDKRVESKYGPPCPPCPAPEFLG
GPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLP
PSQEEMTKNQVSLTCLVKGFYPSDIAVEWESNGQPENNYKTIPPVLDSDGSFFLYSKL
TVDKSRWQEGNVFSCSVMHEALHNHYTQKSLSLSLG Amino acid sequence of region 1 comprised in the MMP9 epitope
SEQ ID NO: 41: AVTPLTFTRVYSRDADIVIQF Amino acid sequence of region 2 comprised in the MMP9 epitope
SEQ ID NO: 42: IQGDAHFDDDELWSLGKGVVVPTRFG Amino acid sequence of region 3 comprised in the MMP9 epitope
SEQ ID NO: 43: MYPMYRFTEGPPLHKDDVNGIR Amino acid sequence of heavy chain of comparative antibody 1 (known as AB0041)
SEQ ID NO: 44:
QVQLKESGPGLVAPSQSLSITCTVSGFSLLSYGVHWVRQPPGKGLEWLGVIWTGGTTN
YNSALMSRLSISKDDSKSQVFLKMNSLQTDDTAIYYCARYYYGMDYWGQGTSVTVSSA
STKGPSVFPLAPCSRSTSESTAALGCLVKDYFPEPVTVSWNSGALTSGVHTFPAVLQS
SGLYSLSSVVTVPSSSLGTKTYTCNVDHKPSNTKVDKRVESKYGPPCPPCPAPEFLGG
PSVFLFPPKPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPREPQVYTLPP
SQEEMTKNQVSLTCLVKGFYPSDIAVEWESNGQPENNYKTTPPVLDSDGSFFLYSKLT
VDKSRWQEGNVFSCSVMHEALHNHYTQKSLSLSLG Amino acid sequence of light chain of comparative antibody 1 (known as AB0041)
SEQ ID NO: 45:
DIVMTQSHKFMSTSVGDRVSITCKASQDVRNTVAWYQQKTGQSPKLLIYSSSYRNTGV
PDRFTGSGSGTDFTFTISSVQAEDLAVYFCQQHYITPYTFGGGTKLEIKRTVAAPSVF
IFPPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC Amino acid sequence of heavy chain of comparative antibody 2 (known as 539A-M0240-B03)
SEQ ID NO: 46:
EVQLLESGGGLVQPGGSLRLSCAASGFTFSTYQMVWVRQAPGKGLEWVSVIYPSGGPT
VYADSVKGRFTISRDNSKNTLYLQMNSLRAEDTAVYYCARGEDYYDSSGPGAFDIWGQ
GTMVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHT
CPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGK Amino acid sequence of light chain of comparative antibody 2 (known as 539A-M0240-B03)
SEQ ID NO: 47:
QYELTQPRSVSGSPGQSVTISCTGTSSDVGGYNYVSWYQQHPGKAPKLMIYDVSKRPS
GVPDRFSGSKSGNTASLTISGLQAEDEADYYCCSYAGSYTLVFGGGTKLTVLGQPKAN
PTVTLFPPSSEELQANKATLVCLISDFYPGAVTVAWKADGSPVKAGVETTKPSKQSNN
KYAASSYLSLTPEQWKSHRSYSCQVTHEGSTVEKTVAPTECS Amino acid sequence of heavy chain F20-VH-GL2
SEQ ID NO: 48:
EVQLVESGGGLVQPGRSLRLSCAASGFTF<u>DDYPMH</u>WVRQAPGKGLEWVS<u>GISSNSGSV
GYADSVKG</u>RFTISRDNAKNSLYLQMNSLR<u>A</u>EDTA<u>L</u>YYCARD<u>KIYYGSGSYDFYYYGM
DV</u>WGQGTTVTVSS Amino acid sequence of heavy chain F20-VH-CDR2-V2
SEQ ID NO: 49: GISS<u>H</u>SGSVGYADSVKG Amino acid sequence of heavy chain F20-VH-CDR2-V3
SEQ ID NO: 50: GISS<u>K</u>SGSVGYADSVKG -continued

LIST OF SEQUENCES

Amino acid sequence of heavy chain F20-VH-CDR2-V11
SEQ ID NO: 51: GISSNSGSVGYADTVKG Amino acid sequence of heavy chain F20-VH-CDR3-V13
SEQ ID NO: 52: DKIYYGSGSYDFYYYGLDV Amino acid sequence of heavy chain F20-VH-GL1-V2
SEQ ID NO: 53:
EVQLVESGGGLVQPGRSLRLSCAASGFTFNDYPMHWVRQAPGKGLEWVSGISSHSGSV
GYADSVKGRFTISRDNAKNSLYLQMNSLRAEDTALYYCARDKIYYGSGSYDFYYYGM
DVWGQGTTVTVSS Amino acid sequence of heavy chain F20-VH-GL1-V3
SEQ ID NO: 54:
EVQLVESGGGLVQPGRSLRLSCAASGFTFNDYPMHWVRQAPGKGLEWVSGISSKSGSV
GYADSVKGRFTISRDNAKNSLYLQMNSLRAEDTALYYCARDKIYYGSGSYDFYYYGM
DVWGQGTTVTVSS Amino acid sequence of heavy chain F20-VH-GL1-V11
SEQ ID NO: 55:
EVQLVESGGGLVQPGRSLRLSCAASGFTFNDYPMHWVRQAPGKGLEWVSGISSNSGSV
GYADTVKGRFTISRDNAKNSLYLQMNSLRAEDTALYYCARDKIYYGSGSYDFYYYGM
DVWGQGTTVTVSS Amino acid sequence of heavy chain F20-VH-GL1-V13
SEQ ID NO: 56:
EVQLVESGGGLVQPGRSLRLSCAASGFTFNDYPMHWVRQAPGKGLEWVSGISSNSGSV
GYADSVKGRFTISRDNAKNSLYLQMNSLRAEDTALYYCARDKIYYGSGSYDFYYYGL
DVWGQGTTVTVSS Amino acid sequence of light chain B03-VL-GL2
SEQ ID NO: 57:
SSELTQDPAVSVALGQTVRITCQGDSLRSYYASWYQQKPGQAPVLVIYGKNNRPSGIP
DRFSGSSSGNTASLTITGAQAEDEADYYCQSRDNIGNHRVVLFGGGTKLTVL Amino acid sequence of light chain B08-VL-GL1
SEQ ID NO: 58:
QSALTQPRSVSGSPGQSITISCTGTSNDVGAYNRVSWYQQHPGKAPKLLIYGVSNRPS
GVSNRFSGSKSGNTASLTISGLQAEDEADFYCTSYSSSTTSYVVFGGGTKVTVL Amino acid sequence of light chain B08-VL-GL2
SEQ ID NO: 59:
QSALTQPASVSGSPGQSITISCTGTSNDVGAYNRVSWYQQHPGKAPKLLIYGVSNRPS
GVSNRFSGSKSGNTASLTISGLQAEDEADFYCTSYSSSTTSYVVFGGGTKVTVL Amino acid sequence of light chain B08-VL-GL3
SEQ ID NO: 60:
QSALTQPRSVSGSPGQSITISCTGTSNDVGAYNRVSWYQQHPGKAPKLLIYGVSNRPS
GVSNRFSGSKSGNTASLTISGLQAEDEADYYCTSYSSSTTSYVVFGGGTKVTVL Amino acid sequence of light chain B08-VL-GL4
SEQ ID NO: 61:
QSALTQPRSVSGSPGQSITISCTGTSNDVGAYNRVSWYQQHPGKAPKLMIYGVSNRPS
GVSNRFSGSKSGNTASLTISGLQAEDEADFYCTSYSSSTTSYVVFGGGTKVTVL Amino acid sequence of light chain B08-VL-GL5
SEQ ID NO: 62:
QSALTQPASVSGSPGQSITISCTGTSNDVGAYNRVSWYQQHPGKAPKLLIYGVSNRPS
GVSNRFSGSKSGNTASLTISGLQAEDEADYYCTSYSSSTTSYVVFGGGTKVTVL Amino acid sequence of light chain B08-VL-GL7
SEQ ID NO: 63:
QSALTQPASVSGSPGQSITISCTGTSNDVGAYNRVSWYQQHPGKAPKLMIYGVSNRPS
GVSNRFSGSKSGNTASLTISGLQAEDEADYYCTSYSSSTTSYVVFGGGTKVTVL Amino acid sequence of heavy chain of comparative antibody
3 (known as 539A-M0237-D02)
SEQ ID NO: 64:
EVQLVESGGGLVQPGGSLRLSCAASGFTFSQYPMWWVRQAPGKGLEWVSYIVPSGGRT
YYADSVKGRFTISRDNSKNTLYLQMNSLRAEDTAVYYCAKDRAYGDYVGWNGFDYWGQ
GTLVTVSSASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEPKSCDKTHT
CPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGK Amino acid sequence of light chain of comparative antibody 3 (known as 539A-M0237-D02)
SEQ ID NO: 65:
DIQMTQSPATLSLSPGERATLSCRASQSISSFLAWYQQKPGQAPRLLIYDASYRATGI
PARFSGSGSGTDFTLTISSLEPEDFAVYYCQQRGNWPITFGQGTRLEIKRTVAAPSVF
IFPPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC Amino acid sequence of engineered human IgG4 light chain constant region
SEQ ID NO: 66:
GQPKAAPSVTLFPPSSEELQANKATLVCLISDFYPGAVTVAWKADSSPVKAGVETTTP
SKQSNNKYAASSYLSLTPEQWKSHRSYSCQVTHEGSTVEKTVAPTECS Amino acid sequence of light chain B03-VLc
SEQ ID NO: 67:
SSELTQDPAVSVALGQTVRITCQGDSLRSYYASWYQQKPGQAPVVVIYGKNNRPSGIP
DRFSGSSSGNTVSLTITGAQAEDEADYYCQSRDNIGNHRVVLFGGGTKVTVL Amino acid sequence of light chain B03-VL-GL1c
SEQ ID NO: 68:
SSELTQDPAVSVALGQTVRITCQGDSLRSYYASWYQQKPGQAPVVVIYGKNNRPSGIP
DRFSGSSSGNTVSLTITGAQAEDEADYYCQSRDNIGNHRVVLFGGGTKLTVL Amino acid sequence of light chain B08-VLc
SEQ ID NO: 69:
QSALTQPRSVSGSPGQSVTISCTGTSNDVGAYNRVSWYQQHPGKAPKLLIYGVSNRPS
GVSTRFSGSKSGNTASLTISGLLAADEADFYCTSYSSSTTSYVVFGGGTKVTVL Amino acid sequence of light chain B08-VL-GL6c
SEQ ID NO: 70:
QSALTQPASVSGSPGQSITISCTGTSNDVGAYNRVSWYQQHPGKAPKLMIYGVSNRPS
GVSNRFSGSKSGNTASLTISGLQAEDEADFYCTSYSSSTTSYVVFGGGTKVTVL Amino acid sequence combining heavy chain variable region F20-VH-GL1-V1-V9 (SEQ ID NO: 17) and an IgG4 heavy chain constant region (SEQ ID NO: 40)
SEQ ID NO: 71:
EVQLVESGGGLVQPGRSLRLSCAASGFTFNDYPMHWVRQAPGKGLEWVS
GISSQSGSVGYAESVKGRFTISRDNAKNSLYLQMNSLRAEDTALYYCAR
DKIYYGSGSYDFYYYYGMDVWGQGTTVTVSSASTKGPSVFPLAPCSRSTS
ESTAALGCLVKDYFPEPVTVSWNSGALTSGVHTFPAVLQSSGLYSLSSVV
TVPSSSLGTKTYTCNVDHKPSNTKVDKRVESKYGPPCPPCPAPEFLGGPS
VFLFPPKPKDTLMISRTPEVTCVVVDVSQEDPEVQFNWYVDGVEVHNAKT
KPREEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQPEN
NYKTTPPVLDSDGSFFLYSKLTVDKSRWQEGNVFSCSVMHEALHNHYTQ
KSLSLSLG Amino acid sequence combining heavy chain variable region F20-VH-GL1-V1-V9-V14(SEQ ID NO: 18) and an IgG4 heavy chain constant region (SEQ ID NO: 40)
SEQ ID NO: 72:
EVQLVESGGGLVQPGRSLRLSCAASGFTFNDYPMHWVRQAPGKGLEWVS
GISSQSGSVGYAESVKGRFTISRDNAKNSLYLQMNSLRAEDTALYYCAR
DKIYYGSGSYDFYYYYGIDVWGQGTTVTVSSASTKGPSVFPLAPCSRST
SESTAALGCLVKDYFPEPVTVSWNSGALTSGVHTFPAVLQSSGLYSLS
SVVTVPSSSLGTKTYTCNVDHKPSNTKVDKRVESKYGPPCPPCPAPEF
LGGPSVFLFPPKPKDTLMISRTPEVTCVVVDVSQEDPEVQFNWYVDGVE
VHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEW
ESNGQPENNYKTTPPVLDSDGSFFLYSKLTVDKSRWQEGNVFSCSVMHE
ALHNHYTQKSLSLSLG Amino acid sequence combining heavy chain variable region F20-VH-GL1-V4-V9 (SEQ ID NO: 19) and an IgG4 heavy chain constant region (SEQ ID NO: 40)
SEQ ID NO: 73:
EVQLVESGGGLVQPGRSLRLSCAASGFTFNDYPMHWVRQAPGKGLEWVS
GISSRSGSVGYAESVKGRFTISRDNAKNSLYLQMNSLRAEDTALYYCAR
DKIYYGSGSYDFYYYYGMDVWGQGTTVTVSSASTKGPSVFPLAPCSRST
SESTAALGCLVKDYFPEPVTVSWNSGALTSGVHTFPAVLQSSGLYSLS
SVVTVPSSSLGTKTYTCNVDHKPSNTKVDKRVESKYGPPCPPCPAPEFL
GGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIE
KTISKAKGQPREPQVYTLPPSQEEMTKNQVSLTCLVKGFYPSDIAVEW
ESNGUENNYKTTPPVLDSDGSFFLYSKLTVDKSRWQEGNVFSCSVMHE
ALHNHYTQKSLSLSLG Amino acid sequence combining heavy chain variable region F20-VH-GL1-V4-V9-V14 (SEQ ID NO: 20) and an IgG4 heavy chain constant region (SEQ ID NO: 40)
SEQ ID NO: 74:
EVQLVESGGGLVQPGRSLRLSCAASGFTFN<u>DYPMH</u>WVRQAPGKGLEWVS
<u>GISSRSGSVGYAE</u>SVKGRFTISRDNAKNSLYLQMNSLRAEDTALYYCAR
<u>DKIYYGSGSYDFYYYYGMDV</u>WGQGTTVTVSSASTKGPSVFPLAPCSRST
SESTAALGCLVKDYFPEPVTVSWNSGALTSGVHTFPAVLQSSGLYSLS
SVVTVPSSSLGTKTYTCNVDHKPSNTKVDKRVESKYGPPCPPCPAPEFL
GGPSVFLFPPKPKDTLMISRTPEVTCVVVDVSQEDPEVQFNWYVDGVEV
HNAKTKPREEQFNSTYRVVSVLTVLHQDWLNGKEYKCKVSNKGLPSSIE
KTISKAKGQPREPQVYTLPPSQEEMTKNQVSLTCLVKGFYPSDIAVEW
ESNGUENNYKTTPPVLDSDGSFFLYSKLTVDKSRWQEGNVFSCSVMHE
ALHNHYTQKSLSLSLG Amino acid sequence of Cynomologus monkey MMP9
SEQ ID NO: 75:
MLGLPHTHTHTHTHTHTHTPCPLSQHLPVKEGWGHRSASLKPPQQQLQ
SDTAALTMSLWQPLVLALLVLGCCCAAPRQRQSTLVLFPGDLKTNLTD
RQLAEDYLYRYGYTRVAEMHGDSKSLGPALLLLQKQLSLPQTGELDSA
TLKAMRTPRCGVPDLGRFQTFEGDLKWHHHNITYWIQNYSEDLPRAVI
EDAFARAFALWSAVTPLTFTRVYSRDADIVIQFGVAEHGDGYPFDGKD
GLLAHAFPPGPGIQGDAHFDDDELWSLGKGVVVPTKFGNADGAACHFP
FTFEGRSYSACTTDGRSDGVPWCSTTANYDTDRRFGCPSERLYTQDG
NADGKPCQFPFIFQGQSYSACTTDGRSDGYRWCATTANYDQDKLYGFC
PTRADSTVIGGNSAGELCVFPFTFLGKEYSTCTSEGRGDGRLWCATTS
NFDRDKKWGFCPDQGYSLFLVAAHEFGHALGLDHTSVPEALMYPMYRF
TEEPPLHKDDVNGIQYLYGSRPEPEPRPPTTTTPQPTAPPTVCPTGPP
TVRPSDRPTAGPTGPPSAGPTGPPTAGPSTTTTVPLNPVDDACNVNIF
DAITEIGNQLYLFKDGRYWRFSERRGSRLQGPFLIADTWPALPRKLDS
AFEEPLSKKLFFFSGRQVWVYTGSSVLGPRRLDKLGLGADVAQVTGAL
RRGAGKMLLFSGRRFWRFDVKAQMVDPRSASEVDRMFPGVPLDTHDV
FQYQEKAYFCQDRFYWRVSSQSGVNQVDQVGYVTYDILQCPED Amino acid sequence of rat MMP9
SEQ ID NO: 76:
MSPWQPLLLVLLALGYSFAAPHQRQPTYVVFPRDLKTSNLTDTQLAEDY
LYRYGYTRAAQMMGEKQSLRPALLMLQKQLSLPQTGELDSETLKAIRSP
RCGVPDVGKFQTFDGDLKWHHHNITYWIQSYTEDLPRDVIDDSFARAFA
VWSAVTPLTFTRVYGLEADIVIQFGVAEHGDGYPFDGKDGLLAHAFPPG
PGIQGDAHFDDDELWSLGKGAVVPTYFGNANGAPCHFPFTFEGRSYLSC
TTDGRNDGKPWCGTTADYDTDRKYGFCPSENLYTEHGNGDKPCVFPFI
FEGHSYSACTTKGRSDGYRWCATTANYDQDKADGFCPTRADVTVTGGNS
AGEMCVFPFVFLGKQYSTCTSEGRSDGRLWCATTSNFDADKKWGFCPDQ
GYSLFLVAAHEFGHALGLDHSSVPEALMYPMYHEDSPLHEDDIKGIH
HLYGRGSKPDPRPPATTAAEPQPTAPPTMCSTAPPMAYPTGGPTVAPTG
APSPGPTGPPTAGPSEAPTESSTPDDNPCNVDVFDAIADIQGALHFFK
DGRYWKFSNHGGNQLQGPFLIARTWPAFPSKLNSAFEDPQPKKIFFFL
WAQMWVYTGQSVLGPRSLDKLGLGSEVTLVTGLLPRRGGKALLISRERI
WKFDLKSQKVDPQSVTRLDNEFSGVPWNSHNVFQYQDKAYFCHDKYFWR
VSFHNRVNQVDHVAYVTYDLLQCP Amino acid sequence of mouse MMP9
SEQ ID NO: 77:
MSPWQPLLLALLAFGCSSAAPYQRQPTFVVFPKDLKTSNLTDTQLAEA
YLYRYGYTRAAQMMGEKQSLRPALLMLQKQLSLPQTGELDSQTLKAIR
TPRCGVPDVGRFQTFKGLKWDHHNITYWIQNYSEDLPRDMIDDAFARA
FAVWGEVAPLTFTRVYGPEADIVIQFGVAEHGDGYPFDGKDGLLAHAF
PPGAGVQGDAHFDDDELWSLGKGVVIPTYYGNSNGAPCHFPFTFEGRS
YSACTTDGRNDGTPWCSTTADYDKDGKFGFCPSERLYTEHGNGEGKPC
VFPFIFEGRSYSACTTKGRSDGYRWCATTANYDQDKLYGFCPTRVDAT
VVGGNSAGELCVFPFVFLGKQYSSCTSDGRRDGRLWCATTSNFDTDKK
WGFCPDQGYSLFLVAAHEFGHALGLDHSSVPEALMYPLYSYLEGFPLN
KDDIDGIQYLYGRGSKPDPRPPATTTTEPQPTAPPTMCPTIPPTAYPT
VGPTVGPTGAPSPGPTSSPSPGPTGAPSPGPTAPPTAGSSEASTESLS
PADNPCNVDVFDAIAEIQGALHFFKDGWYWKFLNHRGSPLQGPFLTAR
TWPALPATLDSAFEDPQTKRVFFFSGRQMWVYTGKTVLGPRSLDKLG
LGPEVTHVSGLLPRRLGKALLFSKGRVWRFDLKSQKVDPQSVIRVDK
EFSGVPWNSHDIFQYQDKAYFCHGKFFWRVSFQNEVNKVDHEVNQV
DDVGYVTYDLLQCP Amino acid sequence combining heavy chain variable region F20-VH (SEQ ID NO: 11) and an IgG4 heavy chain constant region (SEQ ID NO: 40)
SEQ ID NO: 78:
EVQLVESGGGLVQPGRSLRLSCAASGFTFN<u>DYPMH</u>WVRQAPGKGLEWVS
<u>GISSNSGSVGYADS</u>VKGRFTISRDNAKNSLYLQMNSLRDEDTAVYYCAR
<u>DKIYYGSGSYDFYYYYGMDV</u>WGQGTTVTVSSASTKGPSVFPLAPCSRST
SESTAALGCLVKDYFPEPVTVSWNSGALTSGVHTFPAVLQSSGLYSLSS
VVTVPSSSLGTKTYTCNVDHKPSNTKVDKRVESKYGPPCPPCPAPEFLG
GPSVFLFPPKPKDTLMISRTPEVTCVVVDVSQEDPEVQFNWYVDGVEVH
NAKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESN
GQPENNYKTTPPVLDSDGSFFLYSKLTVDKSRWQEGNVFSCSVMHEALHN
HYTQKSLSLSLG Amino acid sequence combining heavy chain variable region F20-VH-GL1 (SEQ ID NO: 12) and an IgG4 heavy chain constant region (SEQ ID NO: 40)
SEQ ID NO: 79:
EVQLVESGGGLVQPGRSLRLSCAASGFTFN<u>DYPMH</u>WVRQAPGKGLEWVS
<u>GISSNSGSVGYADS</u>VKGRFTISRDNAKNSLYLQMNSLRDEDTAVYYCAR
<u>DKIYYGSGSYDFYYYYGMDV</u>WGQGTTVTVSSASTKGPSVFPLAPCSRST
SESTAALGCLVKDYFPEPVTVSWNSGALTSGVHTFPAVLQSSGLYSLSS -continued
VVTVPSSSLGTKTYTCNVDHKPSNTKVDKRVESKYGPPCPPCPAPEFLG

GPSVFLFPPKPKDTLMISRTPEVTCVVVDVSQEDPEVQFNWYVDGVEVH

NAKTKPREEQFNSTYRVVSVLTVLHQDWLNGKEYKCKVSNKGLPSSIEK

TISKAKGQPREPQVYTLPPSQEEMTKNQVSLTCLVKGFYPSDIAVEWESN

GQPENNYKTTPPVLDSDGSFFLYSKLTVDKSRWQEGNVFSCSVMHEALHN

HYTQKSLSLSLG

Amino acid sequence combining light chain variable region B03-VLc (SEQ ID NO: 67) and an IgG4 light chain constant region (SEQ ID NO: 66)
SEQ ID NO: 80:
SSELTQDPAVSVALGQTVRITC<u>QGDSLRSYYAS</u>WYQQKPGQAPVVVI <u>YGKNNRPS</u>GIPDRFSGSSSGNTVSLTITGAQAEDEADYYC<u>QSRDNI</u>

<u>GNHRVV</u>LFGGGTKLTVLGQPKAAPSVTLFPPSSEELQANKATLVC

LISDFYPGAVTVAWKADSSPVKAGVETTTPSKQSNNKYAASSYLSLT

PEQWKSHRSYSCQVTHEGSTVEKTVAPTECS

Amino acid sequence combining light chain variable region B03-VL-GL1c(SEQ ID NO: 68) and an IgG4 light chain constant region (SEQ ID NO: 66)
SEQ ID NO: 81:
SSELTQDPAVSVALGQTVRITC<u>QGDSLRSYYAS</u>WYQQKPGQAPVVVI Y<u>GKNNRPS</u>GIPDRFSGSSSGNTVSLTITGAQAEDEADYYC<u>QSRDNI</u>

<u>GNHRVV</u>LFGGGTKLTVLGQPKAAPSVTLFPPSSEELQANKATLVC

LISDFYPGAVTVAWKADSSPVKAGVETTTPSKQSNNKYAASSYLSLT

PEQWKSHRSYSCQVTHEGSTVEKTVAPTECS

Amino acid sequence combining light chain variable region B08-VLc (SEQ ID NO: 69) and an IgG4 light chain constant region (SEQ ID NO: 66)
SEQ ID NO: 82:
QSALTQPASVSGSPGQSITISC<u>TGTSNDVGAYNRVS</u>WYQQHPGKAPKLM IYG<u>VSNRPS</u>GVSNRFSGSKSGNTASLTISGLQAEDEADFYC<u>TSYSSSTT</u>

<u>SYVV</u>FGGGTKVTVLGQPKAAPSVTLFPPSSEELQANKATLVCLISDFYP

GAVTVAWKADSSPVKAGVETTTPSKQSNNKYAASSYLSLTPEQWKSHR

SYSCQVTHEGSTVEKTVAPTECS

Amino acid sequence combining light chain variable region B08-VL-GL6c(SEQ ID NO: 70) and an IgG4 light chain constant region (SEQ ID NO: 66)
SEQ ID NO: 83:
QSALTQPASVSGSPGQSITISC<u>TGTSNDVGAYNRVS</u>WYQQHPGKAPKLM IYG<u>VSNRPS</u>GVSNRFSGSKSGNTASLTISGLQAEDEADFYC<u>TSYSSSTT</u>

<u>SYVV</u>FGGGTKVTVLGQPKAAPSVTLFPPSSEELQANKATLVCLISDFYP

GAVTVAWKADSSPVKAGVETTTPSKQSNNKYAASSYLSLTPEQWKSHR

SYSCQVTHEGSTVEKTVAPTECS

---

The invention claimed is:

1. An isolated antibody specific for MMP9 or an antigen-binding fragment thereof, said antibody or antigen-binding fragment comprising:
   a) a heavy chain variable region comprising:
      (i) SEQ ID NO: 2 (heavy chain CDR1) or a variant thereof wherein 1, 2, or 3 amino acids of said heavy chain CDR1 is substituted by a different amino acid;
      (ii) SEQ ID NO: 3 (heavy chain CDR2) or a variant thereof wherein 1, 2, or 3 amino acids of said heavy chain CDR2 is substituted by a different amino acid; and
      (iii) SEQ ID NO: 4 (heavy chain CDR3) or a variant thereof wherein 1, 2, or 3 amino acids of said heavy chain CDR3 is substituted by a different amino acid; and
   b) a light chain variable region comprising:
      (i) SEQ ID NO: 21 (light chain CDR1) or a variant thereof wherein 1, 2, or 3 amino acids of said light chain CDR1 is substituted by a different amino acid;
      (ii) SEQ ID NO: 22 (light chain CDR2) or a variant thereof wherein 1, 2, or 3 amino acids of said light chain CDR2 is substituted by a different amino acid; and
      (iii) SEQ ID NO: 23 (light chain CDR3) or a variant thereof wherein 1, 2, or 3 amino acids of said light chain CDR3 is substituted by a different amino acid, or
   c) a light chain variable region comprising:
      (i) SEQ ID NO: 26 (light chain CDR1) or a variant thereof wherein 1, 2, or 3 amino acids of said light chain CDR1 is substituted by a different amino acid;
      (ii) SEQ ID NO: 27 (light chain CDR2) or a variant thereof wherein 1, 2, or 3 amino acids of said light chain CDR2 is substituted by a different amino acid; and
      (iii) SEQ ID NO: 28 (light chain CDR3) or a variant thereof wherein 1, 2, or 3 amino acids of said light chain CDR3 is substituted by a different amino acid.

2. The isolated antibody or antigen-binding fragment according to claim 1, said isolated antibody or antigen-binding fragment comprising a light chain variable region comprising:
   (i) SEQ ID NO: 26 (light chain CDR1) or a variant thereof wherein 1, 2, or 3 amino acids of said light chain CDR1 is substituted by a different amino acid;
   (ii) SEQ ID NO: 27 (light chain CDR2) or a variant thereof wherein 1, 2, or 3 amino acids of said light chain CDR2 is substituted by a different amino acid; and
   (iii) SEQ ID NO: 28 (light chain CDR3) or a variant thereof wherein 1, 2, or 3 amino acids of said light chain CDR3 is substituted by a different amino acid.

3. The isolated antibody or antigen-binding fragment according to claim 1, wherein the heavy chain variable region comprises SEQ ID NO: 11, or a variant thereof wherein 1, 2, or 3 amino acids of at least one of the heavy chain CDR1, CDR2, and/or CDR3, and/or 1, 2, 3, 4, 5, 6, 7, 8, 9, 10, 11, 12, 13, 14 or 15 amino acids of the heavy chain variable framework region is substituted by a different amino acid.

4. The isolated antibody or antigen-binding fragment according to claim 1, wherein said heavy chain variable region comprises an amino acid sequence selected from:
   (i) the amino acid sequence SEQ ID NO: 12;
   (ii) the amino acid sequence SEQ ID NO: 13;
   (iii) the amino acid sequence SEQ ID NO: 14;
   (iv) the amino acid sequence SEQ ID NO: 15;
   (v) the amino acid sequence SEQ ID NO: 16;
   (vi) the amino acid sequence SEQ ID NO: 17;
   (vii) the amino acid sequence SEQ ID NO: 18;
   (viii) the amino acid sequence SEQ ID NO: 19;
   (ix) the amino acid sequence SEQ ID NO: 20; or
   (x) the amino acid sequence of SEQ ID NO: 11.

5. The isolated antibody or antigen-binding fragment according to claim 1, said antibody or antigen-binding fragment comprising a light chain variable region comprising:
   (i) SEQ ID NO: 21 (light chain CDR1) or a variant thereof wherein 1, 2, or 3 amino acids of said light chain CDR1 is substituted by a different amino acid;
   (ii) SEQ ID NO: 22 (light chain CDR2) or a variant thereof wherein 1, 2, or 3 amino acids of said light chain CDR2 is substituted by a different amino acid; and (iii) SEQ ID NO: 23 (light chain CDR3) or a variant thereof wherein 1, 2, or 3 amino acids of said light chain CDR3 is substituted by a different amino acid.

6. The isolated antibody or antigen-binding fragment according to claim 1, wherein the light chain variable region comprises an amino acid sequence selected from:
   (1) SEQ ID NO: 24, or a variant thereof wherein 1, 2, or 3 amino acids of at least one of the light chain CDR1, CDR2, and/or CDR3, and/or 1, 2, 3, 4, 5, 6, 7, 8, 9, 10, 11, 12, 13, 14 or 15 amino acids of the light chain variable framework region is substituted by a different amino acid, or
   (2) SEQ ID NO: 29, or a variant thereof wherein 1, 2, or 3 amino acids of at least one of the light chain CDR1, CDR2, and/or CDR3, and/or 1, 2, 3, 4, 5, 6, 7, 8, 9, 10, 11, 12, 13, 14, or 15 amino acids of the light chain variable framework region is substituted by a different amino acid.

7. The isolated antibody or antigen-binding fragment according to claim 1, wherein the light chain variable region comprises an amino acid sequence selected from:
   (i) the amino acid sequence of SEQ ID NO: 67;
   (ii) the amino acid sequence of SEQ ID NO: 68;
   (iii) the amino acid sequence of SEQ ID NO: 69; or
   (iv) the amino acid sequence of SEQ ID NO: 70.

8. The isolated antibody according to claim 1, which is a human monoclonal antibody.

9. An isolated nucleic acid molecule encoding an antibody or antigen binding fragment according to claim 1.

10. A recombinant expression vector comprising a nucleic acid molecule according to claim 9.

11. An isolated host cell comprising a recombinant vector according to claim 10.

12. A process for producing antibodies or antigen-binding fragments comprising culturing a host cell transformed with an expression vector comprising a nucleic acid molecule according to claim 9, that encodes said antibodies or antigen-binding fragments under conditions sufficient to promote expression of said antibodies or said antigen-binding fragments.

13. A pharmaceutical composition comprising an antibody specific for MMP9 or antigen binding fragment thereof according to claim 1, and at least one pharmaceutically acceptable carrier.

14. An ex-vivo method for detecting the presence and/or concentration of MMP9 protein in a biological sample, comprising the steps of:
   (i) providing a biological sample from a subject,
   (ii) reacting said biological sample with at least one antibody or antigen-binding fragment according to claim 1, under conditions sufficient for binding MMP9 protein present in said biological sample to said at least one antibody or antigen binding fragment through antigen-antibody interactions; and
   (iii) detecting a signal proportional to the level of antigen-antibody complex foiined in step (ii),
   wherein the intensity of the signal correlates with the concentration of MMP9 protein in the biological sample.

15. The ex-vivo method according to claim 14 for detecting the presence and/or concentration of active MMP9 protein in a biological sample.

16. The ex-vivo method according to claim 14, wherein at least one antibody or antigen binding fragment thereof comprises a heavy chain variable region of SEQ ID NO: 19 and a light chain variable region of SEQ ID NO: 70.

17. An isolated antibody specific for MMP9 or an antigen-binding fragment thereof, wherein said the antibody or fragment thereof comprises a heavy chain variable region of SEQ ID NO: 19 and a light chain variable region of SEQ ID NO: 70.

* * * * *

UNITED STATES PATENT AND TRADEMARK OFFICE
CERTIFICATE OF CORRECTION

Page 1 of 2

PATENT NO. : 10,364,296 B2
APPLICATION NO. : 15/503447
DATED : July 30, 2019
INVENTOR(S) : Yolande Chvatchko Missotten et al.

It is certified that error appears in the above-identified patent and that said Letters Patent is hereby corrected as shown below:

In the Specification

Column 6,
Line 32, "*F20-VII-GL1-V1-V9-V14" should read --*F20-VH-GL1-V1-V9-V14--.

Column 62,
Line 40, "1198" should read --I198--.

Column 69,
Line 9, "GYAESVKGR" should read --GYAESVKGR--.

Column 77,
Line 19, "ESNGUENNY" should read --ESNGQPENNY--.

Column 78,
Lines 38-39, "andchain an IgG4 heavy constant region" should read --and an IgG4 heavy chain constant region--.
Line 62, "QMNSLRDEDTAVYY" should read --QMNSLRAEDTALYY--.

Column 79,
Line 17, "GTKLTVL" should read --GTKVTVL--.

Column 80,
Line 11, "TQPAS" should read --TQPRS--.
Line 11, "QSITIS" should read --QSVTIS--.
Line 11, "KAPKLM" should read --KAPKLL--.
Line 13, "SGLQAEDEAD" should read --SGLLAADEAD--.

Signed and Sealed this
Eighteenth Day of February, 2020

Andrei Iancu
*Director of the United States Patent and Trademark Office*

In the Claims

Column 168,
Line 20, "foiined in step" should read --formed in step--.

SEQUENCE LISTING

<160> NUMBER OF SEQ ID NOS: 83

<210> SEQ ID NO 1
<211> LENGTH: 707
<212> TYPE: PRT
<213> ORGANISM: Homo sapiens

<400> SEQUENCE: 1

Met Ser Leu Trp Gln Pro Leu Val Leu Val Leu Val Leu Gly Cys
1               5                   10                  15

Cys Phe Ala Ala Pro Arg Gln Arg Gln Ser Thr Leu Val Leu Phe Pro
                20                  25                  30

Gly Asp Leu Arg Thr Asn Leu Thr Asp Arg Gln Leu Ala Glu Glu Tyr
            35                  40                  45

Leu Tyr Arg Tyr Gly Tyr Thr Arg Val Ala Glu Met Arg Gly Glu Ser
        50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
                100                 105                 110

Asp Leu Lys Trp His His His Asn Ile Thr Tyr Trp Ile Gln Asn Tyr
            115                 120                 125

Ser Glu Asp Leu Pro Arg Ala Val Ile Asp Asp Ala Phe Ala Arg Ala
        130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly

```
                    165                 170                 175
Asp Gly Tyr Pro Phe Asp Gly Lys Asp Gly Leu Leu Ala His Ala Phe
                180                 185                 190

Pro Pro Gly Pro Gly Ile Gln Gly Asp Ala His Phe Asp Asp Glu
            195                 200                 205

Leu Trp Ser Leu Gly Lys Gly Val Val Pro Thr Arg Phe Gly Asn
        210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
                260                 265                 270

Ser Glu Arg Leu Tyr Thr Gln Asp Gly Asn Ala Asp Gly Lys Pro Cys
            275                 280                 285

Gln Phe Pro Phe Ile Phe Gln Gly Gln Ser Tyr Ser Ala Cys Thr Thr
            290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
            355                 360                 365

Gly Arg Leu Trp Cys Ala Thr Thr Ser Asn Phe Asp Ser Asp Lys Lys
        370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
                420                 425                 430

Lys Asp Asp Val Asn Gly Ile Arg His Leu Tyr Gly Pro Arg Pro Glu
            435                 440                 445

Pro Glu Pro Arg Pro Pro Thr Thr Thr Pro Gln Pro Thr Ala Pro
450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
            500                 505                 510

Asp Asp Ala Cys Asn Val Asn Ile Phe Asp Ala Ile Ala Glu Ile Gly
            515                 520                 525

Asn Gln Leu Tyr Leu Phe Lys Asp Gly Lys Tyr Trp Arg Phe Ser Glu
        530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Arg Leu Ser
                565                 570                 575

Lys Lys Leu Phe Phe Phe Ser Gly Arg Gln Val Trp Val Tyr Thr Gly
            580                 585                 590
```

```
Ala Ser Val Leu Gly Pro Arg Arg Leu Asp Lys Leu Gly Leu Gly Ala
        595                 600                 605

Asp Val Ala Gln Val Thr Gly Ala Leu Arg Ser Gly Arg Gly Lys Met
    610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
            660                 665                 670

Phe Cys Gln Asp Arg Phe Tyr Trp Arg Val Ser Ser Arg Ser Glu Leu
        675                 680                 685

Asn Gln Val Asp Gln Val Gly Tyr Val Thr Tyr Asp Ile Leu Gln Cys
        690                 695                 700

Pro Glu Asp
705

<210> SEQ ID NO 2
<211> LENGTH: 5
<212> TYPE: PRT
<213> ORGANISM: Artificial Sequence
<220> FEATURE:
<223> OTHER INFORMATION: heavy chain F20-VH-CDR1

<400> SEQUENCE: 2

Asp Tyr Pro Met His
1               5

<210> SEQ ID NO 3
<211> LENGTH: 17
<212> TYPE: PRT
<213> ORGANISM: Artificial Sequence
<220> FEATURE:
<223> OTHER INFORMATION: heavy chain F20-VH-CDR2

<400> SEQUENCE: 3

Gly Ile Ser Ser Asn Ser Gly Ser Val Gly Tyr Ala Asp Ser Val Lys
1               5                   10                  15

Gly

<210> SEQ ID NO 4
<211> LENGTH: 20
<212> TYPE: PRT
<213> ORGANISM: Artificial Sequence
<220> FEATURE:
<223> OTHER INFORMATION: heavy chain F20-VH-CDR3

<400> SEQUENCE: 4

Asp Lys Ile Tyr Tyr Gly Ser Gly Ser Tyr Asp Phe Tyr Tyr Tyr Tyr
1               5                   10                  15

Gly Met Asp Val
            20

<210> SEQ ID NO 5
<211> LENGTH: 17
<212> TYPE: PRT
<213> ORGANISM: Artificial Sequence
<220> FEATURE:
<223> OTHER INFORMATION: heavy chain F20-VH-CDR2-V1

<400> SEQUENCE: 5
```

```
Gly Ile Ser Ser Gln Ser Gly Ser Val Gly Tyr Ala Asp Ser Val Lys
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: heavy chain F20-VH-CDR2-V4

<400> SEQUENCE: 6

Gly Ile Ser Ser Arg Ser Gly Ser Val Gly Tyr Ala Asp Ser Val Lys
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: heavy chain F20-VH-CDR2-V9

<400> SEQUENCE: 7

Gly Ile Ser Ser Asn Ser Gly Ser Val Gly Tyr Ala Glu Ser Val Lys
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: heavy chain F20-VH-CDR2-V1-V9

<400> SEQUENCE: 8

Gly Ile Ser Ser Gln Ser Gly Ser Val Gly Tyr Ala Glu Ser Val Lys
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: heavy chain F20-VH-CDR2-V4-V9

<400> SEQUENCE: 9

Gly Ile Ser Ser Arg Ser Gly Ser Val Gly Tyr Ala Glu Ser Val Lys
1               5                   10                  15

Gly

<210> SEQ ID NO 10
<211> LENGTH: 20
<212> TYPE: PRT
<213> ORGANISM: Artificial Sequence
<220> FEATURE:
<223> OTHER INFORMATION: heavy chain F20-VH-CDR3-V14

<400> SEQUENCE: 10

Asp Lys Ile Tyr Tyr Gly Ser Gly Ser Tyr Asp Phe Tyr Tyr Tyr
1               5                   10                  15

Gly Ile Asp Val
```

-continued

```
                20

<210> SEQ ID NO 11
<211> LENGTH: 129
<212> TYPE: PRT
<213> ORGANISM: Artificial Sequence
<220> FEATURE:
<223> OTHER INFORMATION: heavy chain F20-VH

<400> SEQUENCE: 11

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Pro Met His Trp Val Arg Gln Ala Pro Gly Lys Gly Leu Glu Trp Val
        35                  40                  45

Ser Gly Ile Ser Ser Asn Ser Gly Ser Val Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Lys Ile Tyr Tyr Gly Ser Gly Ser Tyr Asp Phe Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 12
<211> LENGTH: 129
<212> TYPE: PRT
<213> ORGANISM: Artificial Sequence
<220> FEATURE:
<223> OTHER INFORMATION: F20-VH-GL1

<400> SEQUENCE: 12

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Pro Met His Trp Val Arg Gln Ala Pro Gly Lys Gly Leu Glu Trp Val
        35                  40                  45

Ser Gly Ile Ser Ser Asn Ser Gly Ser Val Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 13
<211> LENGTH: 129
<212> TYPE: PRT
<213> ORGANISM: Artificial Sequence
```

```
<220> FEATURE:
<223> OTHER INFORMATION: heavy chain F20-VH-GL1-V1

<400> SEQUENCE: 13
```

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Arg |
| 1 | | | | 5 | | | | | 10 | | | | | 15 |

Ser Leu Arg Leu Ser Cys Ala Ala Ser Gly Phe Thr Phe Asn Asp Tyr
                20                  25                  30

Pro Met His Trp Val Arg Gln Ala Pro Gly Lys Gly Leu Glu Trp Val
            35                  40                  45

Ser Gly Ile Ser Ser Gln Ser Gly Ser Val Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
            100                 105                 110

Tyr Tyr Gly Met Asp Val Trp Gly Gln Gly Thr Thr Val Thr Val Ser
        115                 120                 125

Ser

```
<210> SEQ ID NO 14
<211> LENGTH: 129
<212> TYPE: PRT
<213> ORGANISM: Artificial Sequence
<220> FEATURE:
<223> OTHER INFORMATION: heavy chain F20-VH-GL1-V4

<400> SEQUENCE: 14
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
                20                  25                  30

Pro Met His Trp Val Arg Gln Ala Pro Gly Lys Gly Leu Glu Trp Val
            35                  40                  45

Ser Gly Ile Ser Ser Arg Ser Gly Ser Val Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
            100                 105                 110

Tyr Tyr Gly Met Asp Val Trp Gly Gln Gly Thr Thr Val Thr Val Ser
        115                 120                 125

Ser

```
<210> SEQ ID NO 15
<211> LENGTH: 129
<212> TYPE: PRT
<213> ORGANISM: Artificial Sequence
<220> FEATURE:
<223> OTHER INFORMATION: heavy chain F20-VH-GL1-V9

<400> SEQUENCE: 15
```

Glu Val Gln Leu Val Glu Ser Gly Gly Gly Leu Val Gln Pro Gly Arg
1               5                   10                  15

```
Ser Leu Arg Leu Ser Cys Ala Ala Ser Gly Phe Thr Phe Asn Asp Tyr
            20                  25                  30

Pro Met His Trp Val Arg Gln Ala Pro Gly Lys Gly Leu Glu Trp Val
            35                  40                  45

Ser Gly Ile Ser Ser Asn Ser Gly Ser Val Tyr Ala Glu Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
            100                 105                 110

Tyr Tyr Gly Met Asp Val Trp Gly Gln Gly Thr Thr Val Thr Val Ser
            115                 120                 125

Ser
```

<210> SEQ ID NO 16
<211> LENGTH: 129
<212> TYPE: PRT
<213> ORGANISM: Artificial Sequence
<220> FEATURE:
<223> OTHER INFORMATION: heavy chain F20-VH-GL1-V14

<400> SEQUENCE: 16

```
Glu Val Gln Leu Val Glu Ser Gly Gly Gly Leu Val Gln Pro Gly Arg
 1               5                   10                  15

Ser Leu Arg Leu Ser Cys Ala Ala Ser Gly Phe Thr Phe Asn Asp Tyr
            20                  25                  30

Pro Met His Trp Val Arg Gln Ala Pro Gly Lys Gly Leu Glu Trp Val
            35                  40                  45

Ser Gly Ile Ser Ser Asn Ser Gly Ser Val Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
            100                 105                 110

Tyr Tyr Gly Ile Asp Val Trp Gly Gln Gly Thr Thr Val Thr Val Ser
            115                 120                 125

Ser
```

<210> SEQ ID NO 17
<211> LENGTH: 129
<212> TYPE: PRT
<213> ORGANISM: Artificial Sequence
<220> FEATURE:
<223> OTHER INFORMATION: heavy chain F20-VH-GL1-V1-V9

<400> SEQUENCE: 17

```
Glu Val Gln Leu Val Glu Ser Gly Gly Gly Leu Val Gln Pro Gly Arg
 1               5                   10                  15

Ser Leu Arg Leu Ser Cys Ala Ala Ser Gly Phe Thr Phe Asn Asp Tyr
            20                  25                  30

Pro Met His Trp Val Arg Gln Ala Pro Gly Lys Gly Leu Glu Trp Val
            35                  40                  45
```

Ser Gly Ile Ser Ser Gln Ser Gly Ser Val Gly Tyr Ala Glu Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
               100                 105                 110

Tyr Tyr Gly Met Asp Val Trp Gly Gln Gly Thr Thr Val Thr Val Ser
            115                 120                 125

Ser

<210> SEQ ID NO 18
<211> LENGTH: 129
<212> TYPE: PRT
<213> ORGANISM: Artificial Sequence
<220> FEATURE:
<223> OTHER INFORMATION: heavy chain F20-VH-GL1-V1-V9-V14

<400> SEQUENCE: 18

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asn Asp Tyr
                20                  25                  30

Pro Met His Trp Val Arg Gln Ala Pro Gly Lys Gly Leu Glu Trp Val
            35                  40                  45

Ser Gly Ile Ser Ser Gln Ser Gly Ser Val Gly Tyr Ala Glu Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
               100                 105                 110

Tyr Tyr Gly Ile Asp Val Trp Gly Gln Gly Thr Thr Val Thr Val Ser
            115                 120                 125

Ser

<210> SEQ ID NO 19
<211> LENGTH: 129
<212> TYPE: PRT
<213> ORGANISM: Artificial Sequence
<220> FEATURE:
<223> OTHER INFORMATION: heavy chain F20-VH-GL1-V4-V9

<400> SEQUENCE: 19

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asn Asp Tyr
                20                  25                  30

Pro Met His Trp Val Arg Gln Ala Pro Gly Lys Gly Leu Glu Trp Val
            35                  40                  45

Ser Gly Ile Ser Ser Arg Ser Gly Ser Val Gly Tyr Ala Glu Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys

```
                    85                  90                  95
Ala Arg Asp Lys Ile Tyr Tyr Gly Ser Gly Ser Tyr Asp Phe Tyr Tyr
                100                 105                 110

Tyr Tyr Gly Met Asp Val Trp Gly Gln Gly Thr Thr Val Thr Val Ser
        115                 120                 125

Ser

<210> SEQ ID NO 20
<211> LENGTH: 129
<212> TYPE: PRT
<213> ORGANISM: Artificial Sequence
<220> FEATURE:
<223> OTHER INFORMATION: heavy chain F20-VH-GL1-V4-V9-V14

<400> SEQUENCE: 20

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Pro Met His Trp Val Arg Gln Ala Pro Gly Lys Gly Leu Glu Trp Val
        35                  40                  45

Ser Gly Ile Ser Ser Arg Ser Gly Ser Val Gly Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
                100                 105                 110

Tyr Tyr Gly Ile Asp Val Trp Gly Gln Gly Thr Thr Val Thr Val Ser
        115                 120                 125

Ser

<210> SEQ ID NO 21
<211> LENGTH: 11
<212> TYPE: PRT
<213> ORGANISM: Artificial Sequence
<220> FEATURE:
<223> OTHER INFORMATION: light chain B03-VL-CDR1

<400> SEQUENCE: 21

Gln Gly Asp Ser Leu Arg Ser Tyr Tyr Ala Ser
1               5                   10

<210> SEQ ID NO 22
<211> LENGTH: 7
<212> TYPE: PRT
<213> ORGANISM: Artificial Sequence
<220> FEATURE:
<223> OTHER INFORMATION: light chain B03-VL-CDR2

<400> SEQUENCE: 22

Gly Lys Asn Asn Arg Pro Ser
1               5

<210> SEQ ID NO 23
<211> LENGTH: 13
<212> TYPE: PRT
<213> ORGANISM: Artificial Sequence
<220> FEATURE:
<223> OTHER INFORMATION: light chain B03-VL-CDR3
```

<400> SEQUENCE: 23

Gln Ser Arg Asp Asn Ile Gly Asn His Arg Val Val Leu
1               5                   10

<210> SEQ ID NO 24
<211> LENGTH: 111
<212> TYPE: PRT
<213> ORGANISM: Artificial Sequence
<220> FEATURE:
<223> OTHER INFORMATION: light chain B03-VL

<400> SEQUENCE: 24

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Val Val Ile Tyr
            35                  40                  45

Gly Lys Asn Asn Arg Pro Ser Gly Ile Pro Asp Arg Phe Ser Gly Ser
    50                  55                  60

Ser Ser Gly Asn Thr Val Ser Leu Thr Ile Thr Gly Ala Gln Ala Glu
65                  70                  75                  80

Asp Glu Ala Asp Tyr Tyr Cys Gln Ser Arg Asp Asn Ile Gly Asn His
                85                  90                  95

Arg Val Val Leu Phe Gly Gly Gly Thr Lys Val Thr Val Leu Gly
            100                 105                 110

<210> SEQ ID NO 25
<211> LENGTH: 111
<212> TYPE: PRT
<213> ORGANISM: Artificial Sequence
<220> FEATURE:
<223> OTHER INFORMATION: light chain B03-VL-GL1

<400> SEQUENCE: 25

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Val Val Ile Tyr
            35                  40                  45

Gly Lys Asn Asn Arg Pro Ser Gly Ile Pro Asp Arg Phe Ser Gly Ser
    50                  55                  60

Ser Ser Gly Asn Thr Val Ser Leu Thr Ile Thr Gly Ala Gln Ala Glu
65                  70                  75                  80

Asp Glu Ala Asp Tyr Tyr Cys Gln Ser Arg Asp Asn Ile Gly Asn His
                85                  90                  95

Arg Val Val Leu Phe Gly Gly Gly Thr Lys Leu Thr Val Leu Gly
            100                 105                 110

<210> SEQ ID NO 26
<211> LENGTH: 14
<212> TYPE: PRT
<213> ORGANISM: Artificial Sequence
<220> FEATURE:
<223> OTHER INFORMATION: light chain B08-VL-CDR1

<400> SEQUENCE: 26

Thr Gly Thr Ser Asn Asp Val Gly Ala Tyr Asn Arg Val Ser

<210> SEQ ID NO 27
<211> LENGTH: 7
<212> TYPE: PRT
<213> ORGANISM: Artificial Sequence
<220> FEATURE:
<223> OTHER INFORMATION: light chain B08-VL-CDR2

<400> SEQUENCE: 27

Gly Val Ser Asn Arg Pro Ser
1               5

<210> SEQ ID NO 28
<211> LENGTH: 12
<212> TYPE: PRT
<213> ORGANISM: Artificial Sequence
<220> FEATURE:
<223> OTHER INFORMATION: light chain B08-VL-CDR3

<400> SEQUENCE: 28

Thr Ser Tyr Ser Ser Ser Thr Thr Ser Tyr Val Val
1               5                   10

<210> SEQ ID NO 29
<211> LENGTH: 113
<212> TYPE: PRT
<213> ORGANISM: Artificial Sequence
<220> FEATURE:
<223> OTHER INFORMATION: light chain B08-VL

<400> SEQUENCE: 29

Gln Ser Ala Leu Thr Gln Pro Arg Ser Val Ser Gly Ser Pro Gly Gln
1               5                   10                  15

Ser Val Thr Ile Ser Cys Thr Gly Thr Ser Asn Asp Val Gly Ala Tyr
            20                  25                  30

Asn Arg Val Ser Trp Tyr Gln Gln His Pro Gly Lys Ala Pro Lys Leu
        35                  40                  45

Leu Ile Tyr Gly Val Ser Asn Arg Pro Ser Gly Val Ser Thr Arg Phe
    50                  55                  60

Ser Gly Ser Lys Ser Gly Asn Thr Ala Ser Leu Thr Ile Ser Gly Leu
65                  70                  75                  80

Leu Ala Ala Asp Glu Ala Asp Phe Tyr Cys Thr Ser Tyr Ser Ser Ser
                85                  90                  95

Thr Thr Ser Tyr Val Val Phe Gly Gly Gly Thr Lys Val Thr Val Leu
            100                 105                 110

Gly

<210> SEQ ID NO 30
<211> LENGTH: 113
<212> TYPE: PRT
<213> ORGANISM: Artificial Sequence
<220> FEATURE:
<223> OTHER INFORMATION: light chain B08-VL-GL6

<400> SEQUENCE: 30

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ala Tyr
            20                  25                  30

Asn Arg Val Ser Trp Tyr Gln Gln His Pro Gly Lys Ala Pro Lys Leu
        35                  40                  45

```
Met Ile Tyr Gly Val Ser Asn Arg Pro Ser Gly Val Ser Asn Arg Phe
        50                  55                  60
Ser Gly Ser Lys Ser Gly Asn Thr Ala Ser Leu Thr Ile Ser Gly Leu
 65                  70                  75                  80
Gln Ala Glu Asp Glu Ala Asp Phe Tyr Cys Thr Ser Tyr Ser Ser Ser
                 85                  90                  95
Thr Thr Ser Tyr Val Val Phe Gly Gly Gly Thr Lys Val Thr Val Leu
                100                 105                 110
Gly
```

<210> SEQ ID NO 31
<211> LENGTH: 15
<212> TYPE: DNA
<213> ORGANISM: Artificial Sequence
<220> FEATURE:
<223> OTHER INFORMATION: heavy chain F20-VH-CDR1

<400> SEQUENCE: 31
gactacccca tgcac                                                    15

<210> SEQ ID NO 32
<211> LENGTH: 51
<212> TYPE: DNA
<213> ORGANISM: Artificial Sequence
<220> FEATURE:
<223> OTHER INFORMATION: heavy chain F20-VH-CDR2

<400> SEQUENCE: 32
ggcatctcct ccaactccgg ctccgtgggc tacgccgact ccgtgaaggg c             51

<210> SEQ ID NO 33
<211> LENGTH: 60
<212> TYPE: DNA
<213> ORGANISM: Artificial Sequence
<220> FEATURE:
<223> OTHER INFORMATION: heavy chain F20-VH-CDR3

<400> SEQUENCE: 33
gacaagatct actacggctc cggctcctac gacttctact actactacgg catggacgtg   60

<210> SEQ ID NO 34
<211> LENGTH: 33
<212> TYPE: DNA
<213> ORGANISM: Artificial Sequence
<220> FEATURE:
<223> OTHER INFORMATION: light chain B03-VL-CDR1

<400> SEQUENCE: 34
caaggcgatt ctctgcgctc atattatgct tct                                33

<210> SEQ ID NO 35
<211> LENGTH: 21
<212> TYPE: DNA
<213> ORGANISM: Artificial Sequence
<220> FEATURE:
<223> OTHER INFORMATION: light chain B03-VL-CDR2

<400> SEQUENCE: 35
ggaaaaaaca accgaccatc t                                             21

<210> SEQ ID NO 36
<211> LENGTH: 39
<212> TYPE: DNA

```
<213> ORGANISM: Artificial Sequence
<220> FEATURE:
<223> OTHER INFORMATION: light chain B03-VL-CDR3

<400> SEQUENCE: 36
caatctcgag acaatatagg gaaccataga gttgttctg                              39

<210> SEQ ID NO 37
<211> LENGTH: 42
<212> TYPE: DNA
<213> ORGANISM: Artificial Sequence
<220> FEATURE:
<223> OTHER INFORMATION: light chain B08-VL-CDR1

<400> SEQUENCE: 37
acaggaacgt ctaatgatgt gggggcttac aatcgcgtca gt                          42

<210> SEQ ID NO 38
<211> LENGTH: 21
<212> TYPE: DNA
<213> ORGANISM: Artificial Sequence
<220> FEATURE:
<223> OTHER INFORMATION: light chain B08-VL-CDR2

<400> SEQUENCE: 38
ggcgtgtcta acaggcctag c                                                 21

<210> SEQ ID NO 39
<211> LENGTH: 36
<212> TYPE: DNA
<213> ORGANISM: Artificial Sequence
<220> FEATURE:
<223> OTHER INFORMATION: light chain B08-VL-CDR3

<400> SEQUENCE: 39
acaagctaca gtagcagtac cacatcatat gtcgtc                                 36

<210> SEQ ID NO 40
<211> LENGTH: 326
<212> TYPE: PRT
<213> ORGANISM: Artificial Sequence
<220> FEATURE:
<223> OTHER INFORMATION: Engineered human IgG4 heavy chain constant
      region

<400> SEQUENCE: 40
```

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

-continued

```
Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
                275                 280                 285

Lys Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 41
<211> LENGTH: 21
<212> TYPE: PRT
<213> ORGANISM: Artificial Sequence
<220> FEATURE:
<223> OTHER INFORMATION: region 1 comprised in MMP9 epitope

<400> SEQUENCE: 41

Ala Val Thr Pro Leu Thr Phe Thr Arg Val Tyr Ser Arg Asp Ala Asp
1               5                   10                  15

Ile Val Ile Gln Phe
            20

<210> SEQ ID NO 42
<211> LENGTH: 26
<212> TYPE: PRT
<213> ORGANISM: Artificial Sequence
<220> FEATURE:
<223> OTHER INFORMATION: region 2 comprised in MMP9 epitope

<400> SEQUENCE: 42

Ile Gln Gly Asp Ala His Phe Asp Asp Asp Glu Leu Trp Ser Leu Gly
1               5                   10                  15

Lys Gly Val Val Val Pro Thr Arg Phe Gly
            20                  25

<210> SEQ ID NO 43
<211> LENGTH: 22
<212> TYPE: PRT
<213> ORGANISM: Artificial Sequence
<220> FEATURE:
<223> OTHER INFORMATION: region 3 comprised in MMP9 epitope
```

```
<400> SEQUENCE: 43

Met Tyr Pro Met Tyr Arg Phe Thr Glu Gly Pro Pro Leu His Lys Asp
1               5                   10                  15

Asp Val Asn Gly Ile Arg
            20

<210> SEQ ID NO 44
<211> LENGTH: 441
<212> TYPE: PRT
<213> ORGANISM: Artificial Sequence
<220> FEATURE:
<223> OTHER INFORMATION: heavy chain of comparative antibody 1

<400> SEQUENCE: 44

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
        35                  40                  45

Gly Val Ile Trp Thr Gly Gly Thr Thr Asn Tyr Asn Ser Ala Leu Met
    50                  55                  60

Ser Arg Leu Ser Ile Ser Lys Asp Asp Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Arg Tyr Tyr Tyr Gly Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
```

```
                    325                 330                 335
Gln Pro Arg Glu Pro Gln Val Tyr Thr Leu Pro Pro Ser Gln Glu Glu
                340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
        370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly
            435                 440

<210> SEQ ID NO 45
<211> LENGTH: 214
<212> TYPE: PRT
<213> ORGANISM: Artificial Sequence
<220> FEATURE:
<223> OTHER INFORMATION: light chain of comparative antibody 1

<400> SEQUENCE: 45

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Arg Asn Thr
            20                  25                  30

Val Ala Trp Tyr Gln Gln Lys Thr Gly Gln Ser Pro Lys Leu Leu Ile
        35                  40                  45

Tyr Ser Ser Ser Tyr Arg Asn Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Phe Cys Gln Gln His Tyr Ile Thr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 46
<211> LENGTH: 454
<212> TYPE: PRT
```

<213> ORGANISM: Artificial Sequence
<220> FEATURE:
<223> OTHER INFORMATION: heavy chain of comparative antibody 2

<400> SEQUENCE: 46

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gln Met Val Trp Val Arg Gln Ala Pro Gly Lys Gly Leu Glu Trp Val
        35                  40                  45

Ser Val Ile Tyr Pro Ser Gly Gly Pro Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Glu Asp Tyr Tyr Asp Ser Ser Gly Pro Gly Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
```

```
                385                 390                 395                 400
Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 47
<211> LENGTH: 216
<212> TYPE: PRT
<213> ORGANISM: Artificial Sequence
<220> FEATURE:
<223> OTHER INFORMATION: light chain of comparative antibody 2

<400> SEQUENCE: 47

Gln Tyr Glu Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Leu Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 48
<211> LENGTH: 129
<212> TYPE: PRT
<213> ORGANISM: Artificial Sequence
<220> FEATURE:
<223> OTHER INFORMATION: heavy chain F20-VH-GL2

<400> SEQUENCE: 48

Glu Val Gln Leu Val Glu Ser Gly Gly Gly Leu Val Gln Pro Gly Arg
1               5                   10                  15
```

Ser Leu Arg Leu Ser Cys Ala Ala Ser Gly Phe Thr Phe Asp Asp Tyr
            20                  25                  30

Pro Met His Trp Val Arg Gln Ala Pro Gly Lys Gly Leu Glu Trp Val
        35                  40                  45

Ser Gly Ile Ser Ser Asn Ser Gly Ser Val Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 49
<211> LENGTH: 17
<212> TYPE: PRT
<213> ORGANISM: Artificial Sequence
<220> FEATURE:
<223> OTHER INFORMATION: heavy chain F20-VH-CDR2-V2

<400> SEQUENCE: 49

Gly Ile Ser Ser His Ser Gly Ser Val Gly Tyr Ala Asp Ser Val Lys
1               5                   10                  15

Gly

<210> SEQ ID NO 50
<211> LENGTH: 17
<212> TYPE: PRT
<213> ORGANISM: Artificial Sequence
<220> FEATURE:
<223> OTHER INFORMATION: heavy chain F20-VH-CDR2-V3

<400> SEQUENCE: 50

Gly Ile Ser Ser Lys Ser Gly Ser Val Gly Tyr Ala Asp Ser Val Lys
1               5                   10                  15

Gly

<210> SEQ ID NO 51
<211> LENGTH: 17
<212> TYPE: PRT
<213> ORGANISM: Artificial Sequence
<220> FEATURE:
<223> OTHER INFORMATION: heavy chain F20-VH-CDR2-V11

<400> SEQUENCE: 51

Gly Ile Ser Ser Asn Ser Gly Ser Val Gly Tyr Ala Asp Thr Val Lys
1               5                   10                  15

Gly

<210> SEQ ID NO 52
<211> LENGTH: 20
<212> TYPE: PRT
<213> ORGANISM: Artificial Sequence
<220> FEATURE:
<223> OTHER INFORMATION: heavy chain F20-VH-CDR3-V13

<400> SEQUENCE: 52

Asp Lys Ile Tyr Tyr Gly Ser Gly Ser Tyr Asp Phe Tyr Tyr Tyr Tyr

-continued

```
1               5                   10                  15

Gly Leu Asp Val
            20

<210> SEQ ID NO 53
<211> LENGTH: 129
<212> TYPE: PRT
<213> ORGANISM: Artificial Sequence
<220> FEATURE:
<223> OTHER INFORMATION: heavy chain F20-VH-GL1-V2

<400> SEQUENCE: 53

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Pro Met His Trp Val Arg Gln Ala Pro Gly Lys Gly Leu Glu Trp Val
        35                  40                  45

Ser Gly Ile Ser Ser His Ser Gly Ser Val Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 54
<211> LENGTH: 129
<212> TYPE: PRT
<213> ORGANISM: Artificial Sequence
<220> FEATURE:
<223> OTHER INFORMATION: heavy chain F20-VH-GL1-V3

<400> SEQUENCE: 54

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Pro Met His Trp Val Arg Gln Ala Pro Gly Lys Gly Leu Glu Trp Val
        35                  40                  45

Ser Gly Ile Ser Ser Lys Ser Gly Ser Val Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 55
```

<211> LENGTH: 129
<212> TYPE: PRT
<213> ORGANISM: Artificial Sequence
<220> FEATURE:
<223> OTHER INFORMATION: heavy chain F20-VH-GL1-V11

<400> SEQUENCE: 55

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
                20                  25                  30

Pro Met His Trp Val Arg Gln Ala Pro Gly Lys Gly Leu Glu Trp Val
            35                  40                  45

Ser Gly Ile Ser Ser Asn Ser Gly Ser Val Gly Tyr Ala Asp Thr Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
                100                 105                 110

Tyr Tyr Gly Met Asp Val Trp Gly Gln Gly Thr Thr Val Thr Val Ser
            115                 120                 125

Ser

<210> SEQ ID NO 56
<211> LENGTH: 129
<212> TYPE: PRT
<213> ORGANISM: Artificial Sequence
<220> FEATURE:
<223> OTHER INFORMATION: heavy chain F20-VH-GL1-V13

<400> SEQUENCE: 56

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
                20                  25                  30

Pro Met His Trp Val Arg Gln Ala Pro Gly Lys Gly Leu Glu Trp Val
            35                  40                  45

Ser Gly Ile Ser Ser Asn Ser Gly Ser Val Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
                100                 105                 110

Tyr Tyr Gly Leu Asp Val Trp Gly Gln Gly Thr Thr Val Thr Val Ser
            115                 120                 125

Ser

<210> SEQ ID NO 57
<211> LENGTH: 110
<212> TYPE: PRT
<213> ORGANISM: Artificial Sequence
<220> FEATURE:
<223> OTHER INFORMATION: light chain B03-VL-GL2

<400> SEQUENCE: 57

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Gln Ser Arg Asp Asn Ile Gly Asn His
                85                  90                  95

Arg Val Val Leu Phe Gly Gly Gly Thr Lys Leu Thr Val Leu
            100                 105                 110
```

<210> SEQ ID NO 58
<211> LENGTH: 112
<212> TYPE: PRT
<213> ORGANISM: Artificial Sequence
<220> FEATURE:
<223> OTHER INFORMATION: light chain B08-VL-GL1

<400> SEQUENCE: 58

```
Gln Ser Ala Leu Thr Gln Pro Arg Ser Val Ser Gly Ser Pro Gly Gln
1               5                   10                  15

Ser Ile Thr Ile Ser Cys Thr Gly Thr Ser Asn Asp Val Gly Ala Tyr
                20                  25                  30

Asn Arg Val Ser Trp Tyr Gln Gln His Pro Gly Lys Ala Pro Lys Leu
            35                  40                  45

Leu Ile Tyr Gly Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Phe Tyr Cys Thr Ser Tyr Ser Ser Ser
                85                  90                  95

Thr Thr Ser Tyr Val Val Phe Gly Gly Gly Thr Lys Val Thr Val Leu
            100                 105                 110
```

<210> SEQ ID NO 59
<211> LENGTH: 112
<212> TYPE: PRT
<213> ORGANISM: Artificial Sequence
<220> FEATURE:
<223> OTHER INFORMATION: light chain B08-VL-GL2

<400> SEQUENCE: 59

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ala Tyr
                20                  25                  30

Asn Arg Val Ser Trp Tyr Gln Gln His Pro Gly Lys Ala Pro Lys Leu
            35                  40                  45

Leu Ile Tyr Gly Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Phe Tyr Cys Thr Ser Tyr Ser Ser Ser
```

```
                        85                  90                  95
Thr Thr Ser Tyr Val Val Phe Gly Gly Gly Thr Lys Val Thr Val Leu
            100                 105                 110

<210> SEQ ID NO 60
<211> LENGTH: 112
<212> TYPE: PRT
<213> ORGANISM: Artificial Sequence
<220> FEATURE:
<223> OTHER INFORMATION: light chain B08-VL-GL3

<400> SEQUENCE: 60

Gln Ser Ala Leu Thr Gln Pro Arg Ser Val Ser Gly Ser Pro Gly Gln
1               5                   10                  15

Ser Ile Thr Ile Ser Cys Thr Gly Thr Ser Asn Asp Val Gly Ala Tyr
            20                  25                  30

Asn Arg Val Ser Trp Tyr Gln Gln His Pro Gly Lys Ala Pro Lys Leu
        35                  40                  45

Leu Ile Tyr Gly Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Thr Ser Tyr Ser Ser Ser
                85                  90                  95

Thr Thr Ser Tyr Val Val Phe Gly Gly Gly Thr Lys Val Thr Val Leu
            100                 105                 110

<210> SEQ ID NO 61
<211> LENGTH: 112
<212> TYPE: PRT
<213> ORGANISM: Artificial Sequence
<220> FEATURE:
<223> OTHER INFORMATION: light chain B08-VL-GL4

<400> SEQUENCE: 61

Gln Ser Ala Leu Thr Gln Pro Arg Ser Val Ser Gly Ser Pro Gly Gln
1               5                   10                  15

Ser Ile Thr Ile Ser Cys Thr Gly Thr Ser Asn Asp Val Gly Ala Tyr
            20                  25                  30

Asn Arg Val Ser Trp Tyr Gln Gln His Pro Gly Lys Ala Pro Lys Leu
        35                  40                  45

Met Ile Tyr Gly Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Phe Tyr Cys Thr Ser Tyr Ser Ser Ser
                85                  90                  95

Thr Thr Ser Tyr Val Val Phe Gly Gly Gly Thr Lys Val Thr Val Leu
            100                 105                 110

<210> SEQ ID NO 62
<211> LENGTH: 112
<212> TYPE: PRT
<213> ORGANISM: Artificial Sequence
<220> FEATURE:
<223> OTHER INFORMATION: light chain B08-VL-GL5

<400> SEQUENCE: 62

Gln Ser Ala Leu Thr Gln Pro Ala Ser Val Ser Gly Ser Pro Gly Gln
1               5                   10                  15
```

```
Ser Ile Thr Ile Ser Cys Thr Gly Thr Ser Asn Asp Val Gly Ala Tyr
            20                  25                  30

Asn Arg Val Ser Trp Tyr Gln Gln His Pro Gly Lys Ala Pro Lys Leu
        35                  40                  45

Leu Ile Tyr Gly Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Thr Ser Tyr Ser Ser Ser
                85                  90                  95

Thr Thr Ser Tyr Val Val Phe Gly Gly Gly Thr Lys Val Thr Val Leu
            100                 105                 110
```

<210> SEQ ID NO 63
<211> LENGTH: 112
<212> TYPE: PRT
<213> ORGANISM: Artificial Sequence
<220> FEATURE:
<223> OTHER INFORMATION: light chain B08-VL-GL7

<400> SEQUENCE: 63

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ala Tyr
            20                  25                  30

Asn Arg Val Ser Trp Tyr Gln Gln His Pro Gly Lys Ala Pro Lys Leu
        35                  40                  45

Met Ile Tyr Gly Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Thr Ser Tyr Ser Ser Ser
                85                  90                  95

Thr Thr Ser Tyr Val Val Phe Gly Gly Gly Thr Lys Val Thr Val Leu
            100                 105                 110
```

<210> SEQ ID NO 64
<211> LENGTH: 454
<212> TYPE: PRT
<213> ORGANISM: Artificial Sequence
<220> FEATURE:
<223> OTHER INFORMATION: heavy chain of comparative antibody 3

<400> SEQUENCE: 64

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Pro Met Trp Trp Val Arg Gln Ala Pro Gly Lys Gly Leu Glu Trp Val
        35                  40                  45

Ser Tyr Ile Val Pro Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ala Tyr Gly Asp Tyr Val Gly Trp Asn Gly Phe Asp
```

```
            100                 105                 110
Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
            195                 200                 205

Val Asn His Lys Pro Ser Asn Thr Lys Val Asp Lys Arg Val Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
            355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
            450

<210> SEQ ID NO 65
<211> LENGTH: 214
<212> TYPE: PRT
<213> ORGANISM: Artificial Sequence
<220> FEATURE:
<223> OTHER INFORMATION: light chain of comparative antibody 3

<400> SEQUENCE: 65

Asp Ile Gln Met Thr Gln Ser Pro Ala Thr Leu Ser Leu Ser Pro Gly
```

```
                1               5                  10                 15
            Glu Arg Ala Thr Leu Ser Cys Arg Ala Ser Gln Ser Ile Ser Ser Phe
                            20                  25                 30
            Leu Ala Trp Tyr Gln Gln Lys Pro Gly Gln Ala Pro Arg Leu Leu Ile
                            35                  40                 45
            Tyr Asp Ala Ser Tyr Arg Ala Thr Gly Ile Pro Ala Arg Phe Ser Gly
                            50                  55                 60
            Ser Gly Ser Gly Thr Asp Phe Thr Leu Thr Ile Ser Ser Leu Glu Pro
            65                          70                  75                 80
            Glu Asp Phe Ala Val Tyr Tyr Cys Gln Gln Arg Gly Asn Trp Pro Ile
                            85                  90                 95
            Thr Phe Gly Gln Gly Thr Arg Leu Glu Ile Lys Arg Thr Val Ala Ala
                            100                 105                110
            Pro Ser Val Phe Ile Phe Pro Pro Ser Asp Glu Gln Leu Lys Ser Gly
                            115                 120                125
            Thr Ala Ser Val Val Cys Leu Leu Asn Asn Phe Tyr Pro Arg Glu Ala
                            130                 135                140
            Lys Val Gln Trp Lys Val Asp Asn Ala Leu Gln Ser Gly Asn Ser Gln
            145                         150                 155                160
            Glu Ser Val Thr Glu Gln Asp Ser Lys Asp Ser Thr Tyr Ser Leu Ser
                            165                 170                175
            Ser Thr Leu Thr Leu Ser Lys Ala Asp Tyr Glu Lys His Lys Val Tyr
                            180                 185                190
            Ala Cys Glu Val Thr His Gln Gly Leu Ser Ser Pro Val Thr Lys Ser
                            195                 200                205
            Phe Asn Arg Gly Glu Cys
                            210

<210> SEQ ID NO 66
<211> LENGTH: 106
<212> TYPE: PRT
<213> ORGANISM: Artificial Sequence
<220> FEATURE:
<223> OTHER INFORMATION: engineered human IgG4 light chain constant
      region

<400> SEQUENCE: 66

Gly Gln Pro Lys Ala Ala Pro Ser Val Thr Leu Phe Pro Pro Ser Ser
            1               5                  10                 15
            Glu Glu Leu Gln Ala Asn Lys Ala Thr Leu Val Cys Leu Ile Ser Asp
                            20                  25                 30
            Phe Tyr Pro Gly Ala Val Thr Val Ala Trp Lys Ala Asp Ser Ser Pro
                            35                  40                 45
            Val Lys Ala Gly Val Glu Thr Thr Thr Pro Ser Lys Gln Ser Asn Asn
                50                          55                  60
            Lys Tyr Ala Ala Ser Ser Tyr Leu Ser Leu Thr Pro Glu Gln Trp Lys
            65                          70                  75                 80
            Ser His Arg Ser Tyr Ser Cys Gln Val Thr His Glu Gly Ser Thr Val
                            85                  90                 95
            Glu Lys Thr Val Ala Pro Thr Glu Cys Ser
                            100                 105

<210> SEQ ID NO 67
<211> LENGTH: 110
<212> TYPE: PRT
<213> ORGANISM: Artificial Sequence
<220> FEATURE:
```

<223> OTHER INFORMATION: light chain B03-VLc

<400> SEQUENCE: 67

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Val Ser Leu Thr Ile Thr Gly Ala Gln Ala Glu
65                  70                  75                  80

Asp Glu Ala Asp Tyr Tyr Cys Gln Ser Arg Asp Asn Ile Gly Asn His
                85                  90                  95

Arg Val Val Leu Phe Gly Gly Gly Thr Lys Val Thr Val Leu
            100                 105                 110

<210> SEQ ID NO 68
<211> LENGTH: 110
<212> TYPE: PRT
<213> ORGANISM: Artificial Sequence
<220> FEATURE:
<223> OTHER INFORMATION: light chain B03-VL-GL1c

<400> SEQUENCE: 68

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Val Ser Leu Thr Ile Thr Gly Ala Gln Ala Glu
65                  70                  75                  80

Asp Glu Ala Asp Tyr Tyr Cys Gln Ser Arg Asp Asn Ile Gly Asn His
                85                  90                  95

Arg Val Val Leu Phe Gly Gly Gly Thr Lys Leu Thr Val Leu
            100                 105                 110

<210> SEQ ID NO 69
<211> LENGTH: 112
<212> TYPE: PRT
<213> ORGANISM: Artificial Sequence
<220> FEATURE:
<223> OTHER INFORMATION: light chain B08-VLc

<400> SEQUENCE: 69

Gln Ser Ala Leu Thr Gln Pro Arg Ser Val Ser Gly Ser Pro Gly Gln
1               5                   10                  15

Ser Val Thr Ile Ser Cys Thr Gly Thr Ser Asn Asp Val Gly Ala Tyr
            20                  25                  30

Asn Arg Val Ser Trp Tyr Gln Gln His Pro Gly Lys Ala Pro Lys Leu
        35                  40                  45

Leu Ile Tyr Gly Val Ser Asn Arg Pro Ser Gly Val Ser Thr Arg Phe
    50                  55                  60

Ser Gly Ser Lys Ser Gly Asn Thr Ala Ser Leu Thr Ile Ser Gly Leu

```
                65                  70                  75                  80
Leu Ala Ala Asp Glu Ala Asp Phe Tyr Cys Thr Ser Tyr Ser Ser Ser
                    85                  90                  95

Thr Thr Ser Tyr Val Val Phe Gly Gly Gly Thr Lys Val Thr Val Leu
                100                 105                 110

<210> SEQ ID NO 70
<211> LENGTH: 112
<212> TYPE: PRT
<213> ORGANISM: Artificial Sequence
<220> FEATURE:
<223> OTHER INFORMATION: light chain B08-VL-GL6c

<400> SEQUENCE: 70

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ala Tyr
                20                  25                  30

Asn Arg Val Ser Trp Tyr Gln Gln His Pro Gly Lys Ala Pro Lys Leu
            35                  40                  45

Met Ile Tyr Gly Val Ser Asn Arg Pro Ser Gly Val Ser Asn Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Phe Tyr Cys Thr Ser Tyr Ser Ser Ser
                85                  90                  95

Thr Thr Ser Tyr Val Val Phe Gly Gly Gly Thr Lys Val Thr Val Leu
                100                 105                 110

<210> SEQ ID NO 71
<211> LENGTH: 455
<212> TYPE: PRT
<213> ORGANISM: Artificial Sequence
<220> FEATURE:
<223> OTHER INFORMATION: Amino acid sequence combining heavy chain
      variable region F20-VH-GL1-V1-V9 (SEQ ID NO: 17) and an IgG4
      heavy chain constant region (SEQ ID NO: 40)

<400> SEQUENCE: 71

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
                20                  25                  30

Pro Met His Trp Val Arg Gln Ala Pro Gly Lys Gly Leu Glu Trp Val
            35                  40                  45

Ser Gly Ile Ser Ser Gln Ser Gly Ser Val Gly Tyr Ala Glu Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
                100                 105                 110

Tyr Tyr Gly Met Asp Val Trp Gly Gln Gly Thr Thr Val Thr Val Ser
            115                 120                 125

Ser Ala Ser Thr Lys Gly Pro Ser Val Phe Pro Leu Ala Pro Cys Ser
        130                 135                 140

Arg Ser Thr Ser Glu Ser Thr Ala Ala Leu Gly Cys Leu Val Lys Asp
```

```
                145                 150                 155                 160
Tyr Phe Pro Glu Pro Val Thr Val Ser Trp Asn Ser Gly Ala Leu Thr
                    165                 170                 175

Ser Gly Val His Thr Phe Pro Ala Val Leu Gln Ser Ser Gly Leu Tyr
                180                 185                 190

Ser Leu Ser Ser Val Val Thr Val Pro Ser Ser Ser Leu Gly Thr Lys
            195                 200                 205

Thr Tyr Thr Cys Asn Val Asp His Lys Pro Ser Asn Thr Lys Val Asp
        210                 215                 220

Lys Arg Val Glu Ser Lys Tyr Gly Pro Pro Cys Pro Pro Cys Pro Ala
225                 230                 235                 240

Pro Glu Phe Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                    260                 265                 270

Val Asp Val Ser Gln Glu Asp Pro Glu Val Gln Phe Asn Trp Tyr Val
                275                 280                 285

Asp Gly Val Glu Val His Asn Ala Lys Thr Lys Pro Arg Glu Glu Gln
            290                 295                 300

Phe Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Gly
                    325                 330                 335

Leu Pro Ser Ser Ile Glu Lys Thr Ile Ser Lys Ala Lys Gly Gln Pro
                340                 345                 350

Arg Glu Pro Gln Val Tyr Thr Leu Pro Pro Ser Gln Glu Glu Met Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                    405                 410                 415

Ser Lys Leu Thr Val Asp Lys Ser Arg Trp Gln Glu Gly Asn Val Phe
                420                 425                 430

Ser Cys Ser Val Met His Glu Ala Leu His Asn His Tyr Thr Gln Lys
            435                 440                 445

Ser Leu Ser Leu Ser Leu Gly
    450                 455

<210> SEQ ID NO 72
<211> LENGTH: 455
<212> TYPE: PRT
<213> ORGANISM: Artificial Sequence
<220> FEATURE:
<223> OTHER INFORMATION: Amino acid sequence combining heavy chain
      variable region F20-VH-GL1-V1-V9-V14(SEQ ID NO: 18) and an IgG4
      heavy chain constant region (SEQ ID NO: 40)

<400> SEQUENCE: 72

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Pro Met His Trp Val Arg Gln Ala Pro Gly Lys Gly Leu Glu Trp Val
        35                  40                  45
```

```
Ser Gly Ile Ser Ser Gln Ser Gly Val Gly Tyr Ala Glu Ser Val
    50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Leu Tyr Tyr Cys
                 85                  90                  95
Ala Arg Asp Lys Ile Tyr Tyr Gly Ser Gly Ser Tyr Asp Phe Tyr Tyr
                100                 105                 110
Tyr Tyr Gly Ile Asp Val Trp Gly Gln Gly Thr Thr Val Thr Val Ser
            115                 120                 125
Ser Ala Ser Thr Lys Gly Pro Ser Val Phe Pro Leu Ala Pro Cys Ser
    130                 135                 140
Arg Ser Thr Ser Glu Ser Thr Ala Ala Leu Gly Cys Leu Val Lys Asp
145                 150                 155                 160
Tyr Phe Pro Glu Pro Val Thr Val Ser Trp Asn Ser Gly Ala Leu Thr
                165                 170                 175
Ser Gly Val His Thr Phe Pro Ala Val Leu Gln Ser Ser Gly Leu Tyr
            180                 185                 190
Ser Leu Ser Ser Val Val Thr Val Pro Ser Ser Ser Leu Gly Thr Lys
    195                 200                 205
Thr Tyr Thr Cys Asn Val Asp His Lys Pro Ser Asn Thr Lys Val Asp
210                 215                 220
Lys Arg Val Glu Ser Lys Tyr Gly Pro Pro Cys Pro Pro Cys Pro Ala
225                 230                 235                 240
Pro Glu Phe Leu Gly Gly Pro Ser Val Phe Leu Phe Pro Pro Lys Pro
                245                 250                 255
Lys Asp Thr Leu Met Ile Ser Arg Thr Pro Glu Val Thr Cys Val Val
            260                 265                 270
Val Asp Val Ser Gln Glu Asp Pro Glu Val Gln Phe Asn Trp Tyr Val
    275                 280                 285
Asp Gly Val Glu Val His Asn Ala Lys Thr Lys Pro Arg Glu Glu Gln
    290                 295                 300
Phe Asn Ser Thr Tyr Arg Val Val Ser Val Leu Thr Val Leu His Gln
305                 310                 315                 320
Asp Trp Leu Asn Gly Lys Glu Tyr Lys Cys Lys Val Ser Asn Lys Gly
                325                 330                 335
Leu Pro Ser Ser Ile Glu Lys Thr Ile Ser Lys Ala Lys Gly Gln Pro
            340                 345                 350
Arg Glu Pro Gln Val Tyr Thr Leu Pro Pro Ser Gln Glu Glu Met Thr
    355                 360                 365
Lys Asn Gln Val Ser Leu Thr Cys Leu Val Lys Gly Phe Tyr Pro Ser
    370                 375                 380
Asp Ile Ala Val Glu Trp Glu Ser Asn Gly Gln Pro Glu Asn Asn Tyr
385                 390                 395                 400
Lys Thr Thr Pro Pro Val Leu Asp Ser Asp Gly Ser Phe Phe Leu Tyr
                405                 410                 415
Ser Lys Leu Thr Val Asp Lys Ser Arg Trp Gln Glu Gly Asn Val Phe
            420                 425                 430
Ser Cys Ser Val Met His Glu Ala Leu His Asn His Tyr Thr Gln Lys
    435                 440                 445
Ser Leu Ser Leu Ser Leu Gly
    450                 455
```

<210> SEQ ID NO 73
<211> LENGTH: 455
<212> TYPE: PRT
<213> ORGANISM: Artificial Sequence
<220> FEATURE:
<223> OTHER INFORMATION: Amino acid sequence combining heavy chain variable region F20-VH-GL1-V4-V9 (SEQ ID NO: 19) and an IgG4 heavy chain constant region (SEQ ID NO: 40)

<400> SEQUENCE: 73

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Pro Met His Trp Val Arg Gln Ala Pro Gly Lys Gly Leu Glu Trp Val
        35                  40                  45

Ser Gly Ile Ser Ser Arg Ser Gly Ser Val Gly Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
            100                 105                 110

Tyr Tyr Gly Met Asp Val Trp Gly Gln Gly Thr Thr Val Thr Val Ser
        115                 120                 125

Ser Ala Ser Thr Lys Gly Pro Ser Val Phe Pro Leu Ala Pro Cys Ser
    130                 135                 140

Arg Ser Thr Ser Glu Ser Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Lys
        195                 200                 205

Thr Tyr Thr Cys Asn Val Asp His Lys Pro Ser Asn Thr Lys Val Asp
    210                 215                 220

Lys Arg Val Glu Ser Lys Tyr Gly Pro Pro Cys Pro Pro Cys Pro Ala
225                 230                 235                 240

Pro Glu Phe Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Glu Asp Pro Glu Val Gln Phe Asn Trp Tyr Val
        275                 280                 285

Asp Gly Val Glu Val His Asn Ala Lys Thr Lys Pro Arg Glu Glu Gln
    290                 295                 300

Phe Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Gly
                325                 330                 335

Leu Pro Ser Ser Ile Glu Lys Thr Ile Ser Lys Ala Lys Gly Gln Pro
            340                 345                 350

Arg Glu Pro Gln Val Tyr Thr Leu Pro Pro Ser Gln Glu Glu Met Thr
```

```
          355                 360                 365
Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Glu Gly Asn Val Phe
            420                 425                 430

Ser Cys Ser Val Met His Glu Ala Leu His Asn His Tyr Thr Gln Lys
        435                 440                 445

Ser Leu Ser Leu Ser Leu Gly
450                 455

<210> SEQ ID NO 74
<211> LENGTH: 455
<212> TYPE: PRT
<213> ORGANISM: Artificial Sequence
<220> FEATURE:
<223> OTHER INFORMATION: Amino acid sequence combining heavy chain
      variable region F20-VH-GL1-V4-V9-V14 (SEQ ID NO: 20) and an IgG4
      heavy chain constant region (SEQ ID NO: 40)

<400> SEQUENCE: 74

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Pro Met His Trp Val Arg Gln Ala Pro Gly Lys Gly Leu Glu Trp Val
        35                  40                  45

Ser Gly Ile Ser Ser Arg Ser Gly Ser Val Gly Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
            100                 105                 110

Tyr Tyr Gly Ile Asp Val Trp Gly Gln Gly Thr Thr Val Thr Val Ser
        115                 120                 125

Ser Ala Ser Thr Lys Gly Pro Ser Val Phe Pro Leu Ala Pro Cys Ser
    130                 135                 140

Arg Ser Thr Ser Glu Ser Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Lys
        195                 200                 205

Thr Tyr Thr Cys Asn Val Asp His Lys Pro Ser Asn Thr Lys Val Asp
    210                 215                 220

Lys Arg Val Glu Ser Lys Tyr Gly Pro Pro Cys Pro Pro Cys Pro Ala
225                 230                 235                 240

Pro Glu Phe Leu Gly Gly Pro Ser Val Phe Leu Phe Pro Pro Lys Pro
                245                 250                 255
```

-continued

```
Lys Asp Thr Leu Met Ile Ser Arg Thr Pro Glu Val Thr Cys Val Val
            260                 265                 270

Val Asp Val Ser Gln Glu Asp Pro Glu Val Gln Phe Asn Trp Tyr Val
        275                 280                 285

Asp Gly Val Glu Val His Asn Ala Lys Thr Lys Pro Arg Glu Glu Gln
290                 295                 300

Phe Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Gly
                325                 330                 335

Leu Pro Ser Ser Ile Glu Lys Thr Ile Ser Lys Ala Lys Gly Gln Pro
            340                 345                 350

Arg Glu Pro Gln Val Tyr Thr Leu Pro Pro Ser Gln Glu Glu Met Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Glu Gly Asn Val Phe
            420                 425                 430

Ser Cys Ser Val Met His Glu Ala Leu His Asn His Tyr Thr Gln Lys
        435                 440                 445

Ser Leu Ser Leu Ser Leu Gly
    450                 455

<210> SEQ ID NO 75
<211> LENGTH: 762
<212> TYPE: PRT
<213> ORGANISM: Macaca fascicularis

<400> SEQUENCE: 75

Met Leu Gly Leu Pro His Thr His Thr His Thr His Thr His Thr His
1               5                   10                  15

Thr His Thr Pro Cys Pro Leu Ser Gln His Leu Pro Val Lys Glu Gly
            20                  25                  30

Trp Gly His Arg Ser Ala Ser Leu Lys Pro Pro Gln Gln Gln Leu Gln
        35                  40                  45

Ser Asp Thr Ala Ala Leu Thr Met Ser Leu Trp Gln Pro Leu Val Leu
    50                  55                  60

Ala Leu Leu Val Leu Gly Cys Cys Cys Ala Ala Pro Arg Gln Arg Gln
65                  70                  75                  80

Ser Thr Leu Val Leu Phe Pro Gly Asp Leu Lys Thr Asn Leu Thr Asp
                85                  90                  95

Arg Gln Leu Ala Glu Asp Tyr Leu Tyr Arg Tyr Gly Tyr Thr Arg Val
            100                 105                 110

Ala Glu Met His Gly Asp Ser Lys Ser Leu Gly Pro Ala Leu Leu Leu
        115                 120                 125

Leu Gln Lys Gln Leu Ser Leu Pro Gln Thr Gly Glu Leu Asp Ser Ala
    130                 135                 140

Thr Leu Lys Ala Met Arg Thr Pro Arg Cys Gly Val Pro Asp Leu Gly
145                 150                 155                 160

Arg Phe Gln Thr Phe Glu Gly Asp Leu Lys Trp His His His Asn Ile
```

-continued

```
            165                 170                 175
Thr Tyr Trp Ile Gln Asn Tyr Ser Glu Asp Leu Pro Arg Ala Val Ile
            180                 185                 190
Glu Asp Ala Phe Ala Arg Ala Phe Ala Leu Trp Ser Ala Val Thr Pro
            195                 200                 205
Leu Thr Phe Thr Arg Val Tyr Ser Arg Asp Ala Asp Ile Val Ile Gln
            210                 215                 220
Phe Gly Val Ala Glu His Gly Asp Gly Tyr Pro Phe Asp Gly Lys Asp
225                 230                 235                 240
Gly Leu Leu Ala His Ala Phe Pro Pro Gly Pro Gly Ile Gln Gly Asp
                245                 250                 255
Ala His Phe Asp Asp Asp Glu Leu Trp Ser Leu Gly Lys Gly Val Val
            260                 265                 270
Val Pro Thr Lys Phe Gly Asn Ala Asp Gly Ala Ala Cys His Phe Pro
            275                 280                 285
Phe Thr Phe Glu Gly Arg Ser Tyr Ser Ala Cys Thr Thr Asp Gly Arg
            290                 295                 300
Ser Asp Gly Val Pro Trp Cys Ser Thr Thr Ala Asn Tyr Asp Thr Asp
305                 310                 315                 320
Arg Arg Phe Gly Phe Cys Pro Ser Glu Arg Leu Tyr Thr Gln Asp Gly
                325                 330                 335
Asn Ala Asp Gly Lys Pro Cys Gln Phe Pro Phe Ile Phe Gln Gly Gln
                340                 345                 350
Ser Tyr Ser Ala Cys Thr Thr Asp Gly Arg Ser Asp Gly Tyr Arg Trp
            355                 360                 365
Cys Ala Thr Thr Ala Asn Tyr Asp Gln Asp Lys Leu Tyr Gly Phe Cys
            370                 375                 380
Pro Thr Arg Ala Asp Ser Thr Val Ile Gly Gly Asn Ser Ala Gly Glu
385                 390                 395                 400
Leu Cys Val Phe Pro Phe Thr Phe Leu Gly Lys Glu Tyr Ser Thr Cys
                405                 410                 415
Thr Ser Glu Gly Arg Gly Asp Gly Arg Leu Trp Cys Ala Thr Thr Ser
                420                 425                 430
Asn Phe Asp Arg Asp Lys Lys Trp Gly Phe Cys Pro Asp Gln Gly Tyr
            435                 440                 445
Ser Leu Phe Leu Val Ala Ala His Glu Phe Gly His Ala Leu Gly Leu
            450                 455                 460
Asp His Thr Ser Val Pro Glu Ala Leu Met Tyr Pro Met Tyr Arg Phe
465                 470                 475                 480
Thr Glu Glu Pro Pro Leu His Lys Asp Asp Val Asn Gly Ile Gln Tyr
                485                 490                 495
Leu Tyr Gly Ser Arg Pro Glu Pro Glu Pro Arg Pro Pro Thr Thr Thr
                500                 505                 510
Thr Pro Gln Pro Thr Ala Pro Pro Thr Val Cys Pro Thr Gly Pro Pro
            515                 520                 525
Thr Val Arg Pro Ser Asp Arg Pro Thr Ala Gly Pro Thr Gly Pro Pro
            530                 535                 540
Ser Ala Gly Pro Thr Gly Pro Thr Ala Gly Pro Ser Thr Thr Thr
545                 550                 555                 560
Thr Val Pro Leu Asn Pro Val Asp Asp Ala Cys Asn Val Asn Ile Phe
                565                 570                 575
Asp Ala Ile Thr Glu Ile Gly Asn Gln Leu Tyr Leu Phe Lys Asp Gly
            580                 585                 590
```

```
Arg Tyr Trp Arg Phe Ser Glu Arg Arg Gly Ser Arg Leu Gln Gly Pro
            595                 600                 605

Phe Leu Ile Ala Asp Thr Trp Pro Ala Leu Pro Arg Lys Leu Asp Ser
    610                 615                 620

Ala Phe Glu Glu Pro Leu Ser Lys Lys Leu Phe Phe Ser Gly Arg
625                 630                 635                 640

Gln Val Trp Val Tyr Thr Gly Ser Ser Val Leu Gly Pro Arg Arg Leu
            645                 650                 655

Asp Lys Leu Gly Leu Gly Ala Asp Val Ala Gln Val Thr Gly Ala Leu
            660                 665                 670

Arg Arg Gly Ala Gly Lys Met Leu Leu Phe Ser Gly Arg Arg Phe Trp
            675                 680                 685

Arg Phe Asp Val Lys Ala Gln Met Val Asp Pro Arg Ser Ala Ser Glu
    690                 695                 700

Val Asp Arg Met Phe Pro Gly Val Pro Leu Asp Thr His Asp Val Phe
705                 710                 715                 720

Gln Tyr Gln Glu Lys Ala Tyr Phe Cys Gln Asp Arg Phe Tyr Trp Arg
            725                 730                 735

Val Ser Ser Gln Ser Gly Val Asn Gln Val Asp Gln Val Gly Tyr Val
            740                 745                 750

Thr Tyr Asp Ile Leu Gln Cys Pro Glu Asp
            755                 760

<210> SEQ ID NO 76
<211> LENGTH: 708
<212> TYPE: PRT
<213> ORGANISM: Rattus norvegicus

<400> SEQUENCE: 76

Met Ser Pro Trp Gln Pro Leu Leu Leu Val Leu Leu Ala Leu Gly Tyr
1               5                   10                  15

Ser Phe Ala Ala Pro His Gln Arg Gln Pro Thr Tyr Val Val Phe Pro
                20                  25                  30

Arg Asp Leu Lys Thr Ser Asn Leu Thr Asp Thr Gln Leu Ala Glu Asp
            35                  40                  45

Tyr Leu Tyr Arg Tyr Gly Tyr Thr Arg Ala Ala Gln Met Met Gly Glu
    50                  55                  60

Lys Gln Ser Leu Arg Pro Ala Leu Leu Met Leu Gln Lys Gln Leu Ser
65                  70                  75                  80

Leu Pro Gln Thr Gly Glu Leu Asp Ser Glu Thr Leu Lys Ala Ile Arg
                85                  90                  95

Ser Pro Arg Cys Gly Val Pro Asp Val Gly Lys Phe Gln Thr Phe Asp
            100                 105                 110

Gly Asp Leu Lys Trp His His His Asn Ile Thr Tyr Trp Ile Gln Ser
    115                 120                 125

Tyr Thr Glu Asp Leu Pro Arg Asp Val Ile Asp Ser Phe Ala Arg
130                 135                 140

Ala Phe Ala Val Trp Ser Ala Val Thr Pro Leu Thr Phe Thr Arg Val
145                 150                 155                 160

Tyr Gly Leu Glu Ala Asp Ile Val Ile Gln Phe Gly Val Ala Glu His
                165                 170                 175

Gly Asp Gly Tyr Pro Phe Asp Gly Lys Asp Gly Leu Leu Ala His Ala
            180                 185                 190

Phe Pro Pro Gly Pro Gly Ile Gln Gly Asp Ala His Phe Asp Asp Asp
```

```
            195                 200                 205
Glu Leu Trp Ser Leu Gly Lys Gly Ala Val Pro Thr Tyr Phe Gly
    210                 215                 220

Asn Ala Asn Gly Ala Pro Cys His Phe Pro Phe Thr Phe Glu Gly Arg
225                 230                 235                 240

Ser Tyr Leu Ser Cys Thr Thr Asp Gly Arg Asn Asp Gly Lys Pro Trp
                245                 250                 255

Cys Gly Thr Thr Ala Asp Tyr Asp Thr Asp Arg Lys Tyr Gly Phe Cys
                260                 265                 270

Pro Ser Glu Asn Leu Tyr Thr Glu His Gly Asn Gly Asp Gly Lys Pro
                275                 280                 285

Cys Val Phe Pro Phe Ile Phe Glu Gly His Ser Tyr Ser Ala Cys Thr
                290                 295                 300

Thr Lys Gly Arg Ser Asp Gly Tyr Arg Trp Cys Ala Thr Thr Ala Asn
305                 310                 315                 320

Tyr Asp Gln Asp Lys Ala Asp Gly Phe Cys Pro Thr Arg Ala Asp Val
                325                 330                 335

Thr Val Thr Gly Gly Asn Ser Ala Gly Glu Met Cys Val Phe Pro Phe
                340                 345                 350

Val Phe Leu Gly Lys Gln Tyr Ser Thr Cys Thr Ser Glu Gly Arg Ser
                355                 360                 365

Asp Gly Arg Leu Trp Cys Ala Thr Thr Ser Asn Phe Asp Ala Asp Lys
                370                 375                 380

Lys Trp Gly Phe Cys Pro Asp Gln Gly Tyr Ser Leu Phe Leu Val Ala
385                 390                 395                 400

Ala His Glu Phe Gly His Ala Leu Gly Leu Asp His Ser Ser Val Pro
                405                 410                 415

Glu Ala Leu Met Tyr Pro Met Tyr His Tyr His Glu Asp Ser Pro Leu
                420                 425                 430

His Glu Asp Asp Ile Lys Gly Ile His His Leu Tyr Gly Arg Gly Ser
                435                 440                 445

Lys Pro Asp Pro Arg Pro Pro Ala Thr Thr Ala Ala Glu Pro Gln Pro
                450                 455                 460

Thr Ala Pro Pro Thr Met Cys Ser Thr Ala Pro Met Ala Tyr Pro
465                 470                 475                 480

Thr Gly Gly Pro Thr Val Ala Pro Thr Gly Ala Pro Ser Pro Gly Pro
                485                 490                 495

Thr Gly Pro Pro Thr Ala Gly Pro Ser Glu Ala Pro Thr Glu Ser Ser
                500                 505                 510

Thr Pro Asp Asp Asn Pro Cys Asn Val Asp Val Phe Asp Ala Ile Ala
                515                 520                 525

Asp Ile Gln Gly Ala Leu His Phe Phe Lys Asp Gly Arg Tyr Trp Lys
                530                 535                 540

Phe Ser Asn His Gly Gly Asn Gln Leu Gln Gly Pro Phe Leu Ile Ala
545                 550                 555                 560

Arg Thr Trp Pro Ala Phe Pro Ser Lys Leu Asn Ser Ala Phe Glu Asp
                565                 570                 575

Pro Gln Pro Lys Lys Ile Phe Phe Phe Leu Trp Ala Gln Met Trp Val
                580                 585                 590

Tyr Thr Gly Gln Ser Val Leu Gly Pro Arg Ser Leu Asp Lys Leu Gly
                595                 600                 605

Leu Gly Ser Glu Val Thr Leu Val Thr Gly Leu Leu Pro Arg Arg Gly
                610                 615                 620
```

```
Gly Lys Ala Leu Leu Ile Ser Arg Glu Arg Ile Trp Lys Phe Asp Leu
625                 630                 635                 640

Lys Ser Gln Lys Val Asp Pro Gln Ser Val Thr Arg Leu Asp Asn Glu
            645                 650                 655

Phe Ser Gly Val Pro Trp Asn Ser His Asn Val Phe Gln Tyr Gln Asp
                660                 665                 670

Lys Ala Tyr Phe Cys His Asp Lys Tyr Phe Trp Arg Val Ser Phe His
            675                 680                 685

Asn Arg Val Asn Gln Val Asp His Val Ala Tyr Val Thr Tyr Asp Leu
            690                 695                 700

Leu Gln Cys Pro
705

<210> SEQ ID NO 77
<211> LENGTH: 730
<212> TYPE: PRT
<213> ORGANISM: Mus musculus

<400> SEQUENCE: 77

Met Ser Pro Trp Gln Pro Leu Leu Ala Leu Leu Ala Phe Gly Cys
1               5                   10                  15

Ser Ser Ala Ala Pro Tyr Gln Arg Gln Pro Thr Phe Val Val Phe Pro
            20                  25                  30

Lys Asp Leu Lys Thr Ser Asn Leu Thr Asp Thr Gln Leu Ala Glu Ala
            35                  40                  45

Tyr Leu Tyr Arg Tyr Gly Tyr Thr Arg Ala Ala Gln Met Met Gly Glu
50                  55                  60

Lys Gln Ser Leu Arg Pro Ala Leu Leu Met Leu Gln Lys Gln Leu Ser
65                  70                  75                  80

Leu Pro Gln Thr Gly Glu Leu Asp Ser Gln Thr Leu Lys Ala Ile Arg
                85                  90                  95

Thr Pro Arg Cys Gly Val Pro Asp Val Gly Arg Phe Gln Thr Phe Lys
            100                 105                 110

Gly Leu Lys Trp Asp His His Asn Ile Thr Tyr Trp Ile Gln Asn Tyr
            115                 120                 125

Ser Glu Asp Leu Pro Arg Asp Met Ile Asp Asp Ala Phe Ala Arg Ala
130                 135                 140

Phe Ala Val Trp Gly Glu Val Ala Pro Leu Thr Phe Thr Arg Val Tyr
145                 150                 155                 160

Gly Pro Glu Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Ala Gly Val Gln Gly Asp Ala His Phe Asp Asp Asp Glu
            195                 200                 205

Leu Trp Ser Leu Gly Lys Gly Val Val Ile Pro Thr Tyr Tyr Gly Asn
210                 215                 220

Ser Asn Gly Ala Pro Cys His Phe Pro Phe Thr Phe Glu Gly Arg Ser
225                 230                 235                 240

Tyr Ser Ala Cys Thr Thr Asp Gly Arg Asn Asp Gly Thr Pro Trp Cys
                245                 250                 255

Ser Thr Thr Ala Asp Tyr Asp Lys Asp Gly Lys Phe Gly Phe Cys Pro
            260                 265                 270

Ser Glu Arg Leu Tyr Thr Glu His Gly Asn Gly Glu Gly Lys Pro Cys
```

```
            275                 280                 285
Val Phe Pro Phe Ile Phe Glu Gly Arg Ser Tyr Ser Ala Cys Thr Thr
290                 295                 300
Lys Gly Arg Ser Asp Gly Tyr Arg Trp Cys Ala Thr Thr Ala Asn Tyr
305                 310                 315                 320
Asp Gln Asp Lys Leu Tyr Gly Phe Cys Pro Thr Arg Val Asp Ala Thr
                325                 330                 335
Val Val Gly Gly Asn Ser Ala Gly Glu Leu Cys Val Phe Pro Phe Val
            340                 345                 350
Phe Leu Gly Lys Gln Tyr Ser Ser Cys Thr Ser Asp Gly Arg Arg Asp
            355                 360                 365
Gly Arg Leu Trp Cys Ala Thr Thr Ser Asn Phe Asp Thr Asp Lys Lys
        370                 375                 380
Trp Gly Phe Cys Pro Asp Gln Gly Tyr Ser Leu Phe Leu Val Ala Ala
385                 390                 395                 400
His Glu Phe Gly His Ala Leu Gly Leu Asp His Ser Ser Val Pro Glu
                405                 410                 415
Ala Leu Met Tyr Pro Leu Tyr Ser Tyr Leu Glu Gly Phe Pro Leu Asn
            420                 425                 430
Lys Asp Asp Ile Asp Gly Ile Gln Tyr Leu Tyr Gly Arg Gly Ser Lys
            435                 440                 445
Pro Asp Pro Arg Pro Ala Thr Thr Thr Glu Pro Gln Pro Thr
        450                 455                 460
Ala Pro Pro Thr Met Cys Pro Thr Ile Pro Pro Thr Ala Tyr Pro Thr
465                 470                 475                 480
Val Gly Pro Thr Val Gly Pro Thr Gly Ala Pro Ser Pro Gly Pro Thr
                485                 490                 495
Ser Ser Pro Ser Pro Gly Pro Thr Gly Ala Pro Ser Pro Gly Pro Thr
            500                 505                 510
Ala Pro Pro Thr Ala Gly Ser Ser Glu Ala Ser Thr Glu Ser Leu Ser
            515                 520                 525
Pro Ala Asp Asn Pro Cys Asn Val Asp Val Phe Asp Ala Ile Ala Glu
        530                 535                 540
Ile Gln Gly Ala Leu His Phe Phe Lys Asp Gly Trp Tyr Trp Lys Phe
545                 550                 555                 560
Leu Asn His Arg Gly Ser Pro Leu Gln Gly Pro Phe Leu Thr Ala Arg
                565                 570                 575
Thr Trp Pro Ala Leu Pro Ala Thr Leu Asp Ser Ala Phe Glu Asp Pro
            580                 585                 590
Gln Thr Lys Arg Val Phe Phe Ser Gly Arg Gln Met Trp Val Tyr
            595                 600                 605
Thr Gly Lys Thr Val Leu Gly Pro Arg Ser Leu Asp Lys Leu Gly Leu
        610                 615                 620
Gly Pro Glu Val Thr His Val Ser Gly Leu Leu Pro Arg Arg Leu Gly
625                 630                 635                 640
Lys Ala Leu Leu Phe Ser Lys Gly Arg Val Trp Arg Phe Asp Leu Lys
                645                 650                 655
Ser Gln Lys Val Asp Pro Gln Ser Val Ile Arg Val Asp Lys Glu Phe
            660                 665                 670
Ser Gly Val Pro Trp Asn Ser His Asp Ile Phe Gln Tyr Gln Asp Lys
            675                 680                 685
Ala Tyr Phe Cys His Gly Lys Phe Phe Trp Arg Val Ser Phe Gln Asn
        690                 695                 700
```

```
Glu Val Asn Lys Val Asp His Glu Val Asn Gln Val Asp Asp Val Gly
705                 710                 715                 720

Tyr Val Thr Tyr Asp Leu Leu Gln Cys Pro
                725                 730

<210> SEQ ID NO 78
<211> LENGTH: 455
<212> TYPE: PRT
<213> ORGANISM: Artificial Sequence
<220> FEATURE:
<223> OTHER INFORMATION: Amino acid sequence combining heavy chain
      variable region F20-VH (SEQ ID NO: 11) and an IgG4 heavy chain
      constant region (SEQ ID NO: 40)

<400> SEQUENCE: 78

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
                20                  25                  30

Pro Met His Trp Val Arg Gln Ala Pro Gly Lys Gly Leu Glu Trp Val
            35                  40                  45

Ser Gly Ile Ser Ser Asn Ser Gly Ser Val Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Lys Ile Tyr Tyr Gly Ser Gly Ser Tyr Asp Phe Tyr Tyr
                100                 105                 110

Tyr Tyr Gly Met Asp Val Trp Gly Gln Gly Thr Thr Val Thr Val Ser
            115                 120                 125

Ser Ala Ser Thr Lys Gly Pro Ser Val Phe Pro Leu Ala Pro Cys Ser
        130                 135                 140

Arg Ser Thr Ser Glu Ser Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Lys
        195                 200                 205

Thr Tyr Thr Cys Asn Val Asp His Lys Pro Ser Asn Thr Lys Val Asp
210                 215                 220

Lys Arg Val Glu Ser Lys Tyr Gly Pro Pro Cys Pro Pro Cys Pro Ala
225                 230                 235                 240

Pro Glu Phe Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Glu Asp Pro Glu Val Gln Phe Asn Trp Tyr Val
        275                 280                 285

Asp Gly Val Glu Val His Asn Ala Lys Thr Lys Pro Arg Glu Glu Gln
    290                 295                 300

Phe Asn Ser Thr Tyr Arg Val Val Ser Val Leu Thr Val Leu His Gln
305                 310                 315                 320
```

```
Asp Trp Leu Asn Gly Lys Glu Tyr Lys Cys Lys Val Ser Asn Lys Gly
                325                 330                 335

Leu Pro Ser Ser Ile Glu Lys Thr Ile Ser Lys Ala Lys Gly Gln Pro
            340                 345                 350

Arg Glu Pro Gln Val Tyr Thr Leu Pro Pro Ser Gln Glu Glu Met Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Glu Gly Asn Val Phe
            420                 425                 430

Ser Cys Ser Val Met His Glu Ala Leu His Asn His Tyr Thr Gln Lys
        435                 440                 445

Ser Leu Ser Leu Ser Leu Gly
    450                 455

<210> SEQ ID NO 79
<211> LENGTH: 455
<212> TYPE: PRT
<213> ORGANISM: Artificial Sequence
<220> FEATURE:
<223> OTHER INFORMATION: Amino acid sequence combining heavy chain
      variable region F20-VH-GL1 (SEQ ID NO: 12) and an IgG4 heavy chain
      constant region (SEQ ID NO: 40)

<400> SEQUENCE: 79

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Pro Met His Trp Val Arg Gln Ala Pro Gly Lys Gly Leu Glu Trp Val
        35                  40                  45

Ser Gly Ile Ser Ser Asn Ser Gly Ser Val Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Ile Tyr Tyr Gly Ser Gly Ser Tyr Asp Phe Tyr Tyr
            100                 105                 110

Tyr Tyr Gly Met Asp Val Trp Gly Gln Gly Thr Thr Val Thr Val Ser
        115                 120                 125

Ser Ala Ser Thr Lys Gly Pro Ser Val Phe Pro Leu Ala Pro Cys Ser
    130                 135                 140

Arg Ser Thr Ser Glu Ser Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Lys
        195                 200                 205

Thr Tyr Thr Cys Asn Val Asp His Lys Pro Ser Asn Thr Lys Val Asp
```

```
                210                 215                 220
Lys Arg Val Glu Ser Lys Tyr Gly Pro Pro Cys Pro Pro Cys Pro Ala
225                 230                 235                 240

Pro Glu Phe Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser Gln Glu Asp Pro Glu Val Gln Phe Asn Trp Tyr Val
                275                 280                 285

Asp Gly Val Glu Val His Asn Ala Lys Thr Lys Pro Arg Glu Glu Gln
                290                 295                 300

Phe Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Gly
                325                 330                 335

Leu Pro Ser Ser Ile Glu Lys Thr Ile Ser Lys Ala Lys Gly Gln Pro
                340                 345                 350

Arg Glu Pro Gln Val Tyr Thr Leu Pro Pro Ser Gln Glu Glu Met Thr
                355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Glu Gly Asn Val Phe
                420                 425                 430

Ser Cys Ser Val Met His Glu Ala Leu His Asn His Tyr Thr Gln Lys
                435                 440                 445

Ser Leu Ser Leu Ser Leu Gly
                450                 455

<210> SEQ ID NO 80
<211> LENGTH: 216
<212> TYPE: PRT
<213> ORGANISM: Artificial Sequence
<220> FEATURE:
<223> OTHER INFORMATION: Amino acid sequence combining light chain
      variable region B03-VLc (SEQ ID NO: 67) and an IgG4 light chain
      constant region (SEQ ID NO: 66)

<400> SEQUENCE: 80

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Val Val Ile Tyr
                35                  40                  45

Gly Lys Asn Asn Arg Pro Ser Gly Ile Pro Asp Arg Phe Ser Gly Ser
                50                  55                  60

Ser Ser Gly Asn Thr Val Ser Leu Thr Ile Thr Gly Ala Gln Ala Glu
65                  70                  75                  80

Asp Glu Ala Asp Tyr Tyr Cys Gln Ser Arg Asp Asn Ile Gly Asn His
                85                  90                  95

Arg Val Val Leu Phe Gly Gly Gly Thr Lys Val Thr Val Leu Gly Gln
                100                 105                 110
```

```
Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215
```

<210> SEQ ID NO 81
<211> LENGTH: 216
<212> TYPE: PRT
<213> ORGANISM: Artificial Sequence
<220> FEATURE:
<223> OTHER INFORMATION: Amino acid sequence combining light chain
      variable region B03-VL-GL1c (SEQ ID NO: 68) and an IgG4 light
      chain constant region (SEQ ID NO: 66)

<400> SEQUENCE: 81

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Val Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Val Ser Leu Thr Ile Thr Gly Ala Gln Ala Glu
65                  70                  75                  80

Asp Glu Ala Asp Tyr Tyr Cys Gln Ser Arg Asp Asn Ile Gly Asn His
                85                  90                  95

Arg Val Val Leu Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215
```

<210> SEQ ID NO 82
<211> LENGTH: 218

```
<212> TYPE: PRT
<213> ORGANISM: Artificial Sequence
<220> FEATURE:
<223> OTHER INFORMATION: Amino acid sequence combining light chain
      variable region B08-VLc (SEQ ID NO: 69) and an IgG4 light chain
      constant region (SEQ ID NO: 66)

<400> SEQUENCE: 82
```

Gln Ser Ala Leu Thr Gln Pro Arg Ser Val Ser Gly Ser Pro Gly Gln
1               5                   10                  15

Ser Val Thr Ile Ser Cys Thr Gly Thr Ser Asn Asp Val Gly Ala Tyr
            20                  25                  30

Asn Arg Val Ser Trp Tyr Gln Gln His Pro Gly Lys Ala Pro Lys Leu
        35                  40                  45

Leu Ile Tyr Gly Val Ser Asn Arg Pro Ser Gly Val Ser Thr Arg Phe
    50                  55                  60

Ser Gly Ser Lys Ser Gly Asn Thr Ala Ser Leu Thr Ile Ser Gly Leu
65                  70                  75                  80

Leu Ala Ala Asp Glu Ala Asp Phe Tyr Cys Thr Ser Tyr Ser Ser Ser
                85                  90                  95

Thr Thr Ser Tyr Val Val Phe Gly Gly Gly Thr Lys Val Thr Val Leu
            100                 105                 110

Gly Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys Ser
    210                 215

```
<210> SEQ ID NO 83
<211> LENGTH: 218
<212> TYPE: PRT
<213> ORGANISM: Artificial Sequence
<220> FEATURE:
<223> OTHER INFORMATION: Amino acid sequence combining light chain
      variable region B08-VL-GL6c (SEQ ID NO: 70) and an IgG4 light
      chain constant region (SEQ ID NO: 66)

<400> SEQUENCE: 83
```

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ala Tyr
            20                  25                  30

Asn Arg Val Ser Trp Tyr Gln Gln His Pro Gly Lys Ala Pro Lys Leu
        35                  40                  45

Met Ile Tyr Gly Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Phe Tyr Cys Thr Ser Tyr Ser Ser Ser

```
                           85                      90                      95
Thr Thr Ser Tyr Val Val Phe Gly Gly Gly Thr Lys Val Thr Val Leu
            100                     105                     110

Gly Gln Pro Lys Ala Ala Pro Ser Val Thr Leu Phe Pro Pro Ser Ser
            115                     120                     125

Glu Glu Leu Gln Ala Asn Lys Ala Thr Leu Val Cys Leu Ile Ser Asp
            130                     135                     140

Phe Tyr Pro Gly Ala Val Thr Val Ala Trp Lys Ala Asp Ser Ser Pro
145                     150                     155                     160

Val Lys Ala Gly Val Glu Thr Thr Thr Pro Ser Lys Gln Ser Asn Asn
            165                     170                     175

Lys Tyr Ala Ala Ser Ser Tyr Leu Ser Leu Thr Pro Glu Gln Trp Lys
            180                     185                     190

Ser His Arg Ser Tyr Ser Cys Gln Val Thr His Glu Gly Ser Thr Val
            195                     200                     205

Glu Lys Thr Val Ala Pro Thr Glu Cys Ser
210                     215
```